US012612454B2

(12) United States Patent
Bergeron et al.

(10) Patent No.: US 12,612,454 B2
(45) Date of Patent: Apr. 28, 2026

(54) CANINE ANTIBODY VARIANTS

(71) Applicant: Zoetis Services LLC, Parsippany, NJ (US)

(72) Inventors: Lisa Marie Bergeron, Boulder, CO (US); Henry Luis Campos, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 458 days.

(21) Appl. No.: 18/246,716

(22) PCT Filed: Sep. 28, 2021

(86) PCT No.: PCT/US2021/052338
§ 371 (c)(1),
(2) Date: Mar. 27, 2023

(87) PCT Pub. No.: WO2022/067233
PCT Pub. Date: Mar. 31, 2022

(65) Prior Publication Data
US 2024/0010716 A1      Jan. 11, 2024

Related U.S. Application Data

(60) Provisional application No. 63/084,241, filed on Sep. 28, 2020.

(51) Int. Cl.
| | |
|---|---|
| *C07K 16/22* | (2006.01) |
| *A61K 39/00* | (2006.01) |
| *C07K 16/00* | (2006.01) |
| *C07K 16/18* | (2006.01) |

(52) U.S. Cl.
CPC ............. *C07K 16/22* (2013.01); *C07K 16/00* (2013.01); *C07K 16/18* (2013.01); *A61K 2039/505* (2013.01); *C07K 2317/20* (2013.01); *C07K 2317/52* (2013.01); *C07K 2317/524* (2013.01); *C07K 2317/526* (2013.01); *C07K 2317/72* (2013.01); *C07K 2317/92* (2013.01); *C07K 2317/94* (2013.01); *C07K 2319/00* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 5,585,089 | A | 12/1996 | Queen et al. |
| 5,698,762 | A | 12/1997 | Dauerman |
| 5,807,715 | A | 9/1998 | Morrison et al. |
| 6,284,471 | B1 | 9/2001 | Le et al. |

| | | | |
|---|---|---|---|
| 8,088,376 | B2 | 1/2012 | Chamberlain et al. |
| 8,394,925 | B2 | 3/2013 | Chamberlain et al. |
| 8,546,543 | B2 | 10/2013 | Lazar |
| 8,790,651 | B2 | 7/2014 | Bammert et al. |
| 9,206,253 | B2 | 12/2015 | Bammert et al. |
| 9,505,829 | B2 | 11/2016 | Lacy et al. |
| 9,617,334 | B2 | 4/2017 | Bergeron et al. |
| 9,803,023 | B2 | 10/2017 | Chamberlain et al. |
| 9,944,704 | B2 | 4/2018 | Morsey et al. |
| 9,951,128 | B2 | 4/2018 | Bergeron et al. |
| 10,093,725 | B2 | 10/2018 | Lacy et al. |
| 10,125,192 | B2 | 11/2018 | Lacy et al. |
| 10,336,818 | B2 | 7/2019 | Chamberlain et al. |
| 10,421,807 | B2 | 9/2019 | Gonzales et al. |
| 10,526,405 | B2 | 1/2020 | Mann et al. |
| 2003/0031671 | A1 | 2/2003 | Welt et al. |
| 2006/0067930 | A1 | 3/2006 | Adams et al. |
| 2020/0216536 | A1 | 7/2020 | Brondyk et al. |
| 2024/0010716 | A1 | 1/2024 | Bergeron et al. |

FOREIGN PATENT DOCUMENTS

| | | | |
|---|---|---|---|
| EP | 3892632 | A1 | 10/2021 |
| WO | 1986001533 | A1 | 3/1986 |
| WO | 2020082048 | A1 | 4/2020 |
| WO | 2020112781 | A1 | 6/2020 |
| WO | 2021212081 | A1 | 10/2021 |
| WO | 2021252455 | A1 | 12/2021 |

OTHER PUBLICATIONS

Badri H., et al., "Optimization of Radiation Dosing Schedules for Proneural Glioblastoma", Journal of Mathematical Biology, 2016, vol. 72, No. 5, pp. 1301-1336, 36 Pages, See the abstract.
Baylot V., et al., "TCTP Has a Crucial Role in the Different Stages of Prostate Cancer Malignant Progression", Results and Problems in Cell Differentiation, 2017, vol. 64, pp. 255-261, See the Abstract.
Bergeron L.M., et al., "Comparative Functional Characterization of Canine IgG Subclasses", Veterinary Immunology and Immunopathology, Jan. 15, 2014, vol. 157, No. 12, pp. 31-41, XP028801783.
Bird R.E., et al., Science, 1988, vol. 240, pp. 423-426.
Bowie J.U., et al., "Deciphering the Message in Protein Sequences: Tolerance to Amino Acid Substitutions," Science, 1990, vol. 247, pp. 1306-1310.
Cunningham B.C., et al., "High-Resolution Epitope Mapping of hGH-Receptor Interactions by Alanine-Scanning Mutagenesis", Science, Jun. 2, 1989, vol. 244, pp. 1081-1085.
De Vos A.M., et al., "Human Growth Hormone and Extracellular Domain of Its Receptor: Crystal Structure of the Complex", Science, 1992, vol. 255, pp. 306-312.
Deng R.. et al., "Pharmacokinetics of Humanized Monoclonal Anti-Tumor Necrosis Factor-Alpha Antibody and its Neonatal Fc Receptor Variants in Mice and Cynomolgus Monkeys", Drug Metabolism and Disposition, 2010, vol. 38, No. 4, pp. 600-605, See the Abstract.

(Continued)

*Primary Examiner* — Nora M Rooney
(74) *Attorney, Agent, or Firm* — Prakash Subbiah

(57) ABSTRACT

The disclosure relates generally to canine antibody variants and uses thereof. Specifically, the disclosure relates to mutations in the constant region of canine antibody for improving its half-life and other characters.

11 Claims, 20 Drawing Sheets

Specification includes a Sequence Listing.

(56) References Cited

OTHER PUBLICATIONS

Ellman., et al., Methods in Enzymology, 1991, vol. 202, pp. 301-336.

Gorman M.C., et al., "The Rous Sarcoma Virus Long Terminal Repeat is a Strong Promoter When Introduced into a Variety of Eukaryotic cells by DNA-mediated Transfection", Proceedings of the National Academy of Sciences, USA, 1982, vol. 79, pp. 6777-6781.

Grosschedl R., et al., "Cell-Type Specificity of Immunoglobulin Gene Expression is Regulated by at Least Three DNA Sequence Elements," Cell, Jul. 1985, vol. 41, pp. 885-897(13 Pages).

Guyer R.L., et al., "Immunoglobulin Binding by Mouse Intestinal Epithelial Cell Receptors", Journal of Immunology, vol. 117, No. 2, 1976, pp. 587-593.

International Preliminary Report on Patentability for International Application No. PCT/US2021/052338, dated Apr. 6, 2023, 7 Pages.

International Search Report and Written Opinion for International Application No. PCT/US2021/052338, dated Apr. 22, 2022, 12 Pages.

Izaki, Japanese Journal of Bacteriology, 1978, vol. 33, pp. 729-742.

John J.F., et al., "Plasmids as Epidemiologic Markers in Nosocomial Gram-Negative Bacilli: Experience at a University and Review of the Literature", Reviews of Infectious Diseases, 1986, vol. 8, No. 5, pp. 693-704.

Kabat E.A., et al., "Sequences of Proteins of Immunological Interest," Fifth Edition, Publich Health Service, National Institutes of Health, Bethesda, MD, NIH Publication No. 91-3242, 1991, 11 Pages.

Kendall, et al., Journal of Bacteriology, 1987, vol. 169, pp. 4177-4183.

Kim J-K., et al., "Localization of the Site of the Murine IgG1 Molecule that is Involved in Binding to the Murine Intestinal Fc Receptor," The European Journal of Immunology, 1994, vol. 24, pp. 2429-2434.

Lathe R., "Synthetic Oligonucleotide Probes Deduced from Amino Acid Sequence Data: Theoretical and Practical Considerations", Journal of Molecular Biology, vol. 183, 1985, pp. 1-12.

Newman R., et al., Biotechnology, 1993, vol. 10, pp. 1455-1460.

Okayama H., et al., "A cDNA Cloning Vector That Permits Expression of cDNA Inserts in Mammalian Cells", Molecular and Cellular Biology, Feb. 1983, vol. 3, No. 2, pp. 280-312.

Pearson W.R., et al., "Improved Tools for Biological Sequence Comparison", Proceedings of the National Academy of Sciences of the United States of America, Apr. 1988, vol. 85, pp. 2444-2448.

Pluckthunkerra, Methods in Enzymology, 1989, vol. 178, pp. 497-515.

Rattan S.I., et al., "Protein Synthesis, Posttranslational Modifications, and Aging", Annals of the New York Academy of Sciences, 1992, vol. 663, pp. 48-62.

Seifter S., et al., "Analysis for Protein Modifications and Nonprotein Cofactors", Methods in Enzymology, 1990, vol. 182, pp. 626-646.

Smith L.J., et al., "Human Interlukin 4 The Solution Structure of a Four-Helix Bundle Protein", Journal of Molecular Biology, 1992, vol. 224, pp. 899-904.

Weidle U.H., et al., "Reconstitution of Functionally Active Antibody Directed Against Creatine Kinase from Separately Expressed Heavy and Light Chains in Non-lymphoid Cells", Gene, 1987, vol. 51, pp. 21-29.

Whittle, et al., Protein Engineering, 1987, vol. 1, p. 499.

Figure 2A:
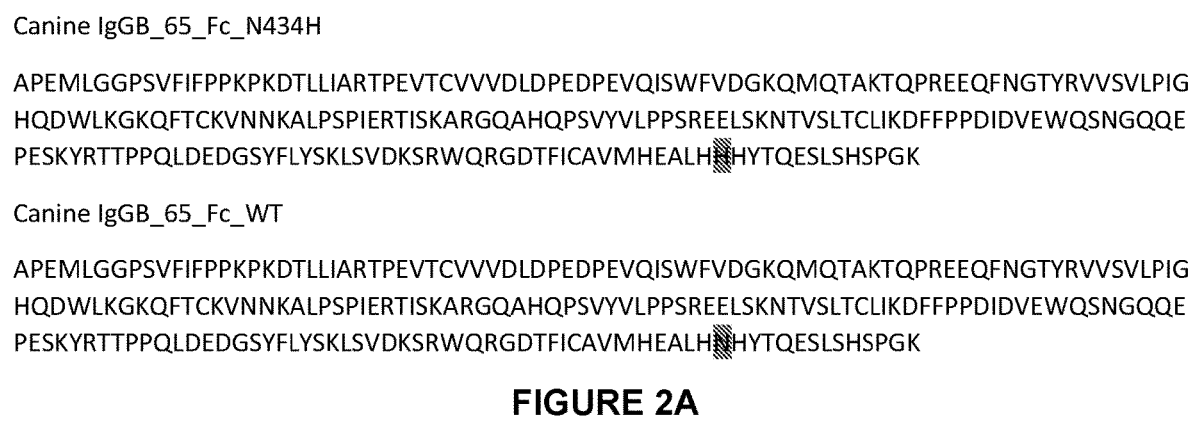

Canine IgGB_65_Fc_N434H

APEMLGGPSVFIFPPKPKDTLLIARTPEVTCVVVDLDPEDPEVQISWFVDGKQMQTAKTQPREEQFNGTYRVVSVLPIG
HQDWLKGKQFTCKVNNKALPSPIERTISKARGQAHQPSVYVLPPSREELSKNTVSLTCLIKDFFPPDIDVEWQSNGQQE
PESKYRTTPPQLDEDGSYFLYSKLSVDKSRWQRGDTFICAVMHEALH░HYTQESLSHSPGK

Canine IgGB_65_Fc_WT

APEMLGGPSVFIFPPKPKDTLLIARTPEVTCVVVDLDPEDPEVQISWFVDGKQMQTAKTQPREEQFNGTYRVVSVLPIG
HQDWLKGKQFTCKVNNKALPSPIERTISKARGQAHQPSVYVLPPSREELSKNTVSLTCLIKDFFPPDIDVEWQSNGQQE
PESKYRTTPPQLDEDGSYFLYSKLSVDKSRWQRGDTFICAVMHEALH░HYTQESLSHSPGK

FIGURE 2A red=CH1     violet=Hinge     Blue=CH2     Green=CH3

>Human IgG1_EU Index                                                                                                          1

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | K | G | P | S | V | F | P | L | A | P | S | S | K | S | T | S | G | G | T | A | A | L | G | C | L | V | K | D |

>Canine IgGA_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | T | A | P | S | V | F | P | L | A | P | S | C | G | S | T | S | G | S | T | V | A | L | A | C | L | V | S | G |

>Canine IgGB_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | T | A | P | S | V | F | P | L | A | P | S | C | G | S | T | S | G | S | T | V | A | L | A | C | L | V | S | G |

>Canine IgGC_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | T | A | P | S | V | F | P | L | A | P | S | C | G | S | Q | S | G | S | T | V | A | L | A | C | L | V | S | G |

>Canine IgGD_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | T | A | P | S | V | F | P | L | A | P | S | C | G | S | T | S | G | S | T | V | A | L | A | C | L | V | S | G |

>Human IgG1_EU Index                                                                                                          2

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | A | V | L | Q | S | S | G | L |

>Canine IgGA_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | S | L | T | S | G | V | H | T | F | P | S | V | L | Q | S | S | G | L |

>Canine IgGB_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | S | L | T | S | G | V | H | T | F | P | S | V | L | Q | S | S | G | L |

>Canine IgGC_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | I | P | E | P | V | T | V | S | W | N | S | V | S | L | T | S | G | V | H | T | F | P | S | V | L | Q | S | S | G | L |

>Canine IgGD_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | S | L | T | S | G | V | H | T | F | P | S | V | L | Q | S | S | G | L |

FIGURE 2B

>Human IgG1_EU Index                                                                                 3

| | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|---|
| Human IgG1 | Y | S | L | S | S | V | V | T | V | P | S | S | S | L | G | T | Q | T | Y | I | C | N | V | N | H | K | P | S | N | T | K |
| Canine IgGA | R | S | L | S | S | M | V | T | V | P | S | G | R | W | P | S | E | T | F | T | C | N | V | V | H | P | A | S | N | T | K |
| Canine IgGB | Y | S | L | S | S | M | V | T | V | P | S | S | R | W | P | S | E | T | F | T | C | N | V | A | H | P | A | S | K | T | K |
| Canine IgGC | Y | S | L | S | S | M | V | T | V | P | S | G | R | W | P | S | E | T | F | T | C | N | V | A | H | P | A | T | N | T | K |
| Canine IgGD | Y | S | L | S | S | T | V | T | V | P | S | S | R | W | P | S | E | T | F | T | C | N | V | V | H | P | A | S | N | T | K |

>Human IgG1_EU Index                                                                                 4

| | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|---|---|---|---|---|---|
| Human IgG1 | V | D | K | K | V | E | P | K | S | C | D | K | T | H | T | C | P | P | C | P | A | P | E | L | L | G | G | P | S | V | F |

>Canine IgGA_EU Index

| | 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|---|---|---|---|---|---|
| Canine IgGA | V | D | K | P | V | F | - | N | E | C | R | C | T | Q | T | - | P | P | C | P | V | S | E | P | I | G | G | P | Q | V | L |

>Canine IgGB_EU Index

| | 211 | 212 | 213 | 214 | 215 | 216 | 217 | 218 | | | | | 219 | 220 | 221 | 222 | 223 | 224 | 225 | 226 | 227 | 228 | 229 | 230 | 231 | 232 | 233 | 234 | 235 | 236 | 237 |
|---|---|---|---|---|---|---|---|---|---|---|---|---|---|---|---|---|---|---|---|---|---|---|---|---|---|---|---|---|---|---|---|---|
| Canine IgGB | V | D | K | P | V | - | P | R | S | F | N | G | R | V | P | R | P | P | Q | C | P | R | C | P | A | P | E | M | L | G | G |

>Canine IgGC_EU Index

| | 211 | 212 | 213 | 214 | 215 | 216 | 217 | 218 | 219 | 220 | 221 | 222 | 223 | 224 | 225 | 226 | 227 | 228 | 229 | 230 | 331 | 232 | | | 233 | 234 | 235 | 236 | 237 | 238 | 239 |
|---|---|---|---|---|---|---|---|---|---|---|---|---|---|---|---|---|---|---|---|---|---|---|---|---|---|---|---|---|---|---|---|
| Canine IgGC | V | D | K | P | V | - | A | R | E | C | E | C | K | C | N | C | N | N | C | P | C | P | | | G | C | G | L | L | G | Q | P | S |

>Canine IgGD_EU Index

| | 211 | 212 | 213 | 214 | 215 | 216 | 217 | 218 | 219 | 220 | 221 | 222 | 223 | 224 | 225 | 226 | | | 227 | 228 | 229 | 230 | 231 | 232 | 233 | 234 | 235 | 236 | 237 | 238 |
|---|---|---|---|---|---|---|---|---|---|---|---|---|---|---|---|---|---|---|---|---|---|---|---|---|---|---|---|---|---|---|---|
| Canine IgGD | V | D | K | P | V | P | K | E | S | - | - | - | - | - | T | C | | | K | C | I | S | P | C | P | Y | E | S | L | G | G | P |

FIGURE 2B (Contd.)

>Human IgG1_EU Index                                                                                                5

| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 |

>Canine IgGA_EU Index

| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 |

>Canine IgGB_EU Index

| 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 |

>Canine IgGC_EU Index

| 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 |

>Canine IgGD_EU Index

| 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 |

>Human IgG1_EU Index                                                                                                6

| 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 | 301 | 302 | 303 |

>Canine IgGA_EU Index

| 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 | 301 | 302 | 303 |

>Canine IgGB_EU Index

| 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 |

>Canine IgGC_EU Index

| 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 | 301 |

>Canine IgGD_EU Index

| 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 |

FIGURE 2B (Contd.)

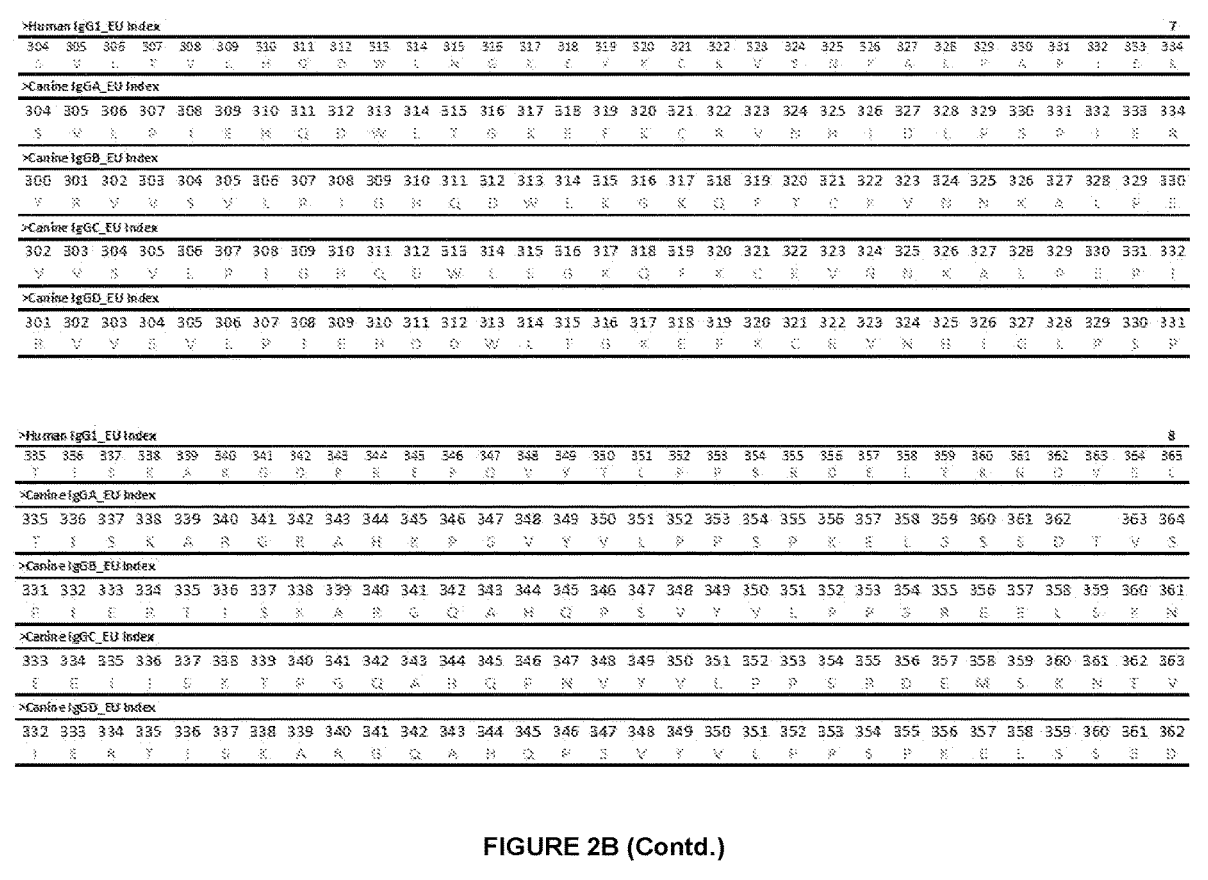

>Human IgG1_EU Index                                                                                                                    7

| 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 331 | 332 | 333 | 334 |
|---|---|---|---|---|---|---|---|---|---|---|---|---|---|---|---|---|---|---|---|---|---|---|---|---|---|---|---|---|---|---|

>Canine IgGA_EU Index

| 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 331 | 332 | 333 | 334 |
|---|---|---|---|---|---|---|---|---|---|---|---|---|---|---|---|---|---|---|---|---|---|---|---|---|---|---|---|---|---|---|---|

>Canine IgGB_EU Index

| 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|---|---|---|---|---|---|---|---|---|---|---|---|---|---|---|---|---|

>Canine IgGC_EU Index

| 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 331 | 332 |
|---|---|---|---|---|---|---|---|---|---|---|---|---|---|---|---|---|---|---|---|---|---|---|---|---|---|---|---|---|---|---|---|

>Canine IgGD_EU Index

| 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 331 |
|---|---|---|---|---|---|---|---|---|---|---|---|---|---|---|---|---|---|---|---|---|---|---|---|---|---|---|---|---|---|---|---|

>Human IgG1_EU Index                                                                                                                    8

| 335 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 360 | 361 | 362 | 363 | 364 | 365 |
|---|---|---|---|---|---|---|---|---|---|---|---|---|---|---|---|---|---|---|---|---|---|---|---|---|---|---|---|---|---|---|---|

>Canine IgGA_EU Index

| 335 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 360 | 361 | 362 | | 363 | 364 |
|---|---|---|---|---|---|---|---|---|---|---|---|---|---|---|---|---|---|---|---|---|---|---|---|---|---|---|---|---|---|---|---|

>Canine IgGB_EU Index

| 331 | 332 | 333 | 334 | 335 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|---|---|---|---|---|---|---|---|---|---|

>Canine IgGC_EU Index

| 333 | 334 | 335 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 360 | 361 | 362 | 363 |
|---|---|---|---|---|---|---|---|---|---|---|---|---|---|---|---|---|---|---|---|---|---|---|---|---|---|---|---|---|---|---|---|

>Canine IgGD_EU Index

| 332 | 333 | 334 | 335 | 336 | 337 | 338 | 339 | 340 | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|---|---|---|---|---|---|---|---|---|---|---|---|---|---|---|---|---|

FIGURE 2B (Contd.)

>Human IgG1_EU Index 9

| 366 | 367 | 368 | 369 | 370 | 371 | 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 |
|---|---|---|---|---|---|---|---|---|---|---|---|---|---|---|---|---|---|---|---|---|---|---|---|---|---|---|---|---|---|---|
| Y | C | L | V | K | G | F | Y | P | S | D | I | A | V | E | W | E | S | N | G | Q | P | E | N | N | Y | K | T | T | P | P |

>Canine IgGA_EU Index

| 365 | 366 | 367 | 368 | 369 | 370 | 371 | 372 | 373 | 374 | 375 | 376 | 377 | 378 | 379 | 380 | 381 | 382 | 383 | 384 | 385 | 386 | | 387 | 388 | 389 | 390 | 391 | 392 | 393 |
|---|---|---|---|---|---|---|---|---|---|---|---|---|---|---|---|---|---|---|---|---|---|---|---|---|---|---|---|---|---|
| | T | C | L | I | K | D | F | Y | P | P | D | I | D | V | E | W | Q | S | N | G | Q | | P | E | R | R | N | N | M |

>Canine IgGB_EU Index

| 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | | 387 | 388 | 389 | 390 |
|---|---|---|---|---|---|---|---|---|---|---|---|---|---|---|---|---|---|---|---|---|---|---|---|---|---|---|---|---|---|
| T | V | S | L | T | C | L | I | K | D | F | F | P | P | D | I | D | V | E | W | Q | S | N | G | Q | | P | E | S | K |

>Canine IgGC_EU Index

| 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | | 387 | 388 | 389 | 390 | 391 | 392 |
|---|---|---|---|---|---|---|---|---|---|---|---|---|---|---|---|---|---|---|---|---|---|---|---|---|---|---|---|---|---|
| T | L | T | C | L | V | K | D | F | F | P | P | E | I | D | V | E | W | Q | S | N | G | Q | | P | E | S | K | Y | R |

>Canine IgGD_EU Index

| | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | | 387 | 388 | 389 | 390 |
|---|---|---|---|---|---|---|---|---|---|---|---|---|---|---|---|---|---|---|---|---|---|---|---|---|---|---|---|---|---|---|
| T | V | T | L | T | C | L | I | K | D | F | F | P | P | E | I | D | V | E | W | Q | S | N | G | Q | | P | E | P | K |

>Human IgG1_EU Index 10

| 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 | 424 | 425 | 426 | 427 |
|---|---|---|---|---|---|---|---|---|---|---|---|---|---|---|---|---|---|---|---|---|---|---|---|---|---|---|---|---|---|---|---|
| V | L | D | S | D | G | S | F | F | L | Y | S | K | L | T | V | D | K | S | R | W | Q | Q | G | N | V | F | S | C | S | V |

>Canine IgGA_EU Index

| 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|---|---|---|---|---|---|---|---|---|---|
| T | P | P | Q | L | D | E | D | G | S | Y | F | L | Y | S | K | L | S | V | D | K | S | R | W | Q | Q | G | Q | P | F | T |

>Canine IgGB_EU Index

| 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|---|---|---|---|
| Y | R | T | T | P | P | Q | L | D | E | D | G | S | Y | F | L | Y | S | K | L | S | V | D | K | S | R | W | Q | R | G | D |

>Canine IgGC_EU Index

| 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 |
|---|---|---|---|---|---|---|---|---|---|---|---|---|---|---|---|---|---|---|---|---|---|---|---|---|---|---|---|---|---|---|---|
| M | T | P | P | Q | L | D | E | D | G | S | Y | F | L | Y | S | K | L | S | V | D | K | S | R | W | Q | R | G | D | T | F |

>Canine IgGD_EU Index

| 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|---|---|---|---|
| Y | H | T | T | A | P | Q | L | D | E | D | G | S | Y | F | L | Y | S | K | L | S | V | D | K | S | R | W | Q | Q | G | D |

FIGURE 2B (Contd.)

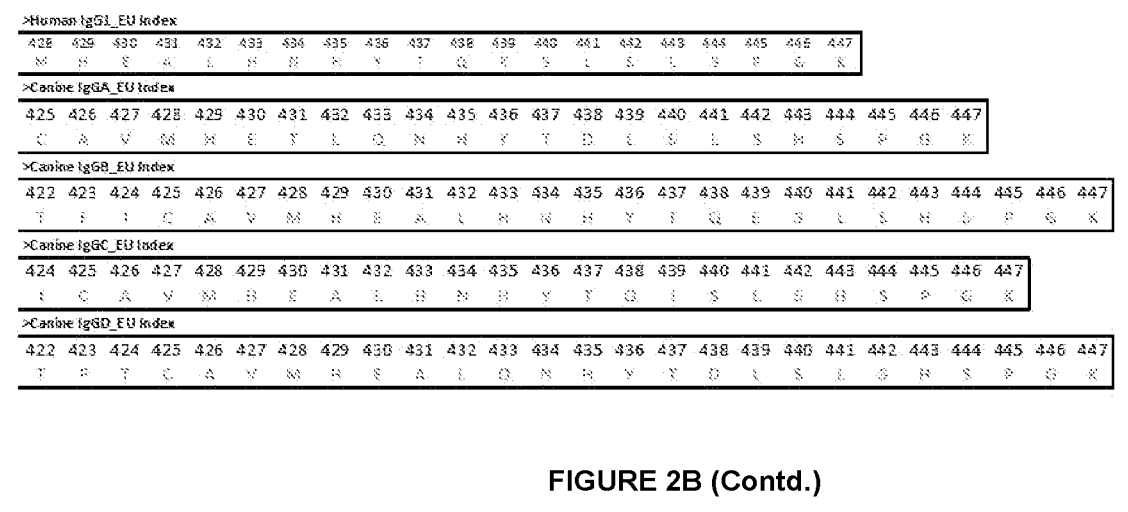

>Human IgG1_EU Index

| 428 | 429 | 430 | 431 | 432 | 433 | 434 | 435 | 436 | 437 | 438 | 439 | 440 | 441 | 442 | 443 | 444 | 445 | 446 | 447 |
|-----|-----|-----|-----|-----|-----|-----|-----|-----|-----|-----|-----|-----|-----|-----|-----|-----|-----|-----|-----|
| M | H | E | A | L | H | N | H | Y | T | Q | K | S | L | S | L | S | P | G | K |

>Canine IgGA_EU Index

| 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|-----|-----|-----|-----|-----|-----|-----|-----|-----|-----|-----|-----|-----|-----|-----|-----|-----|-----|-----|-----|-----|-----|-----|
| C | A | V | M | H | E | T | L | Q | N | H | Y | T | D | L | G | L | S | H | S | P | G | K |

>Canine IgGB_EU Index

| 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|-----|-----|-----|-----|-----|-----|-----|-----|-----|-----|-----|-----|-----|-----|-----|-----|-----|-----|-----|-----|-----|-----|-----|-----|-----|-----|-----|
| T | F | T | C | A | V | M | H | E | A | L | H | N | H | Y | T | Q | E | S | L | S | H | S | P | G | K |

>Canine IgGC_EU Index

| 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|-----|-----|-----|-----|-----|-----|-----|-----|-----|-----|-----|-----|-----|-----|-----|-----|-----|-----|-----|-----|-----|-----|-----|-----|-----|
| T | C | A | V | M | H | E | A | L | H | N | H | Y | T | Q | I | S | L | S | H | S | P | G | K |

>Canine IgGD_EU Index

| 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|-----|-----|-----|-----|-----|-----|-----|-----|-----|-----|-----|-----|-----|-----|-----|-----|-----|-----|-----|-----|-----|-----|-----|-----|-----|-----|-----|
| T | F | T | C | A | V | M | H | E | A | L | Q | N | H | Y | T | D | L | S | L | G | H | S | P | G | K |

FIGURE 2B (Contd.)

| Canine_IgGB_65_Constant CH2-CH3 WT |
|---|
| GCTCCAGAAATGCTGGGAGGACCAAGCGTGTTCATCTTTCCACCC AAGCCCAAAGACACACTGCTGATTGCTAGAACTCCCGAGGTGACC TGCGTGGTGGTGGACCTGGATCCAGAGGACCCCGAAGTGCAGATC TCCTGGTTCGTGGATGGGAAGCAGATGCAGACAGCCAAAACTCAG CCTCGGGAGGAACAGTTTAACGGAACCTATAGAGTGGTGTCTGTG CTGCCAATTGGACACCAGGACTGGCTGAAGGGCAAACAGTTTACA TGCAAGGTGAACAACAAGGCCCTGCCTAGTCCAATCGAGAGGACT ATTTCAAAAGCTAGGGGACAGGCTCATCAGCCTTCCGTGTATGTGC TGCCTCCATCCCGGGAGGAACTGTCTAAGAACACAGTGAGTCTGA CTTGTCTGATCAAAGATTTCTTTCCCCCTGACATTGATGTGGAGTG GCAGAGCAATGGGCAGCAGGAGCCAGAATCCAAGTACAGAACCA CACCACCCCAGCTGGACGAAGATGGCTCCTATTTCCTGTACAGTAA GCTGTCAGTGGACAAATCTAGGTGGCAGCGCGGGGATACCTTTAT CTGCGCCGTGATGCACGAGGCTCTGCACAATCATTACACACAAGA AAGTCTGTCACATAGCCCCGGCAAG |

FIGURE 2C

SEQUENCE LISTING

```
<160> NUMBER OF SEQ ID NOS: 120

<210> SEQ ID NO 1
<211> LENGTH: 335
<212> TYPE: PRT
<213> ORGANISM: Canis familiaris

<400> SEQUENCE: 1

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
```

```
            260                 265                 270
Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His His His Tyr Thr Gln Glu Ser Leu Ser His Ser Pro Gly Lys
                325                 330                 335

<210> SEQ ID NO 2
<211> LENGTH: 335
<212> TYPE: PRT
<213> ORGANISM: Canis familiaris

<400> SEQUENCE: 2

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
        130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
            165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
            245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300
```

-continued

```
Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335

<210> SEQ ID NO 3
<211> LENGTH: 1005
<212> TYPE: DNA
<213> ORGANISM: Canis familiaris

<400> SEQUENCE: 3
gccagcacca cagctccctc cgtgttcccc ctggctccta gctgcggctc tacctccggc      60
agcacagtgg ccctggcttg tctggtgtcc ggctacttcc ctgagccagt gaccgtgagc     120
tggaactccg gctccctgac ctccggagtg cacacatttc caagcgtgct gcagtcttcc     180
ggcctgtatt ctctgagctc tatggtgacc gtgccttcca gcaggtggcc atctgagaca     240
ttcacctgca acgtggccca tcccgcttcc aagacaaagg tggacaagcc cgtgcctaag     300
agggagaatg gaagggtgcc ccggccccct gattgcccta agtgtccagc tccagagatg     360
ctgggaggac catccgtgtt catctttcca cccaagccca aggataccct gctgatcgct     420
agaacccctg aggtgacatg cgtggtggtg gacctggatc cagaggaccc cgaggtgcag     480
atctcttggt tcgtggatgg caagcagatg cagaccgcca agacacagcc tagggaggag     540
cagtttaacg gcacctacag ggtggtgtcc gtgctgccaa tcggccacca ggactggctg     600
aagggcaagc agtttacctg caaggtgaac aataaggctc tgccttctcc aatcgagaga     660
acaatctcca aggccagggg ccaggctcat cagcctagcg tgtacgtgct gcctccatcc     720
agagaggagc tgagcaagaa caccgtgtct ctgacatgtc tgatcaagga tttctttccc     780
cctgacatcg atgtggagtg gcagagcaat ggccagcagg agccagagtc taagtatcgc     840
accacaccac cccagctgga cgaggatggc agctacttcc tgtatagcaa gctgtctgtg     900
gacaagtcta gatggcagcg cggcgatacc tttatctgtg ccgtgatgca cgaggcactg     960
cacaatcact acacccagga gagtctgagc cacagcccag gaaaa              1005

<210> SEQ ID NO 4
<211> LENGTH: 1005
<212> TYPE: DNA
<213> ORGANISM: Canis familiaris

<400> SEQUENCE: 4
gcctcaacaa ctgctcctag cgtgtttccc ctggccccta gctgcggaag tacctcaggc      60
agcacagtgg ccctggcttg tctggtgtct ggatatttcc ctgagccagt gaccgtgagt     120
tggaacagcg gctctctgac ctccggggtg cacacatttc catctgtgct gcagtctagt     180
ggcctgtact ccctgtcaag catggtgact gtgccttcct ctaggtggcc atcagaaact     240
ttcacctgca acgtggccca tcccgccagc aagaccaaag tggacaagcc cgtgcctaaa     300
agggagaatg gaagggtgcc aagaccacct gattgcccta agtgtccagc tccagaaatg     360
ctgggaggac caagcgtgtt catctttcca cccaagccca agacacact gctgattgct      420 agaactcccg aggtgacctg cgtggtggtg gacctggatc cagaggaccc cgaagtgcag     480
atctcctggt tcgtggatgg gaagcagatg cagacagcca aaactcagcc tcgggaggaa     540
cagtttaacg gaacctatag agtggtgtct gtgctgccaa ttggacacca ggactggctg     600
aagggcaaac agtttacatg caaggtgaac aacaaggccc tgcctagtcc aatcgagagg     660
actatttcaa aagctagggg acaggctcat cagccttccg tgtatgtgct gcctccatcc     720
```

```
cgggaggaac tgtctaagaa cacagtgagt ctgacttgtc tgatcaaaga tttctttccc        780
cctgacattg atgtggagtg gcagagcaat gggcagcagg agccagaatc caagtacaga        840
accacaccac cccagctgga cgaagatggc tcctatttcc tgtacagtaa gctgtcagtg        900
gacaaatcta ggtggcagcg cggggatacc tttatctgcg ccgtgatgca cgaggctctg        960
cacaatcatt acacacaaga aagtctgtca catagccccg gcaag                       1005
```

<210> SEQ ID NO 5
<211> LENGTH: 96
<212> TYPE: PRT
<213> ORGANISM: Canis familiaris

<400> SEQUENCE: 5

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95
```

<210> SEQ ID NO 6
<211> LENGTH: 20
<212> TYPE: PRT
<213> ORGANISM: Canis familiaris

<400> SEQUENCE: 6

```
Pro Val Pro Lys Arg Glu Asn Gly Arg Val Pro Arg Pro Pro Asp Cys
1               5                   10                  15

Pro Lys Cys Pro
            20
```

<210> SEQ ID NO 7
<211> LENGTH: 110
<212> TYPE: PRT
<213> ORGANISM: Canis familiaris

<400> SEQUENCE: 7

```
Ala Pro Glu Met Leu Gly Gly Pro Ser Val Phe Ile Phe Pro Pro Lys
1               5                   10                  15

Pro Lys Asp Thr Leu Leu Ile Ala Arg Thr Pro Glu Val Thr Cys Val
                20                  25                  30

Val Val Asp Leu Asp Pro Glu Asp Pro Glu Val Gln Ile Ser Trp Phe
        35                  40                  45

Val Asp Gly Lys Gln Met Gln Thr Ala Lys Thr Gln Pro Arg Glu Glu
    50                  55                  60

Gln Phe Asn Gly Thr Tyr Arg Val Val Ser Val Leu Pro Ile Gly His
65                  70                  75                  80

Gln Asp Trp Leu Lys Gly Lys Gln Phe Thr Cys Lys Val Asn Asn Lys
                85                  90                  95

Ala Leu Pro Ser Pro Ile Glu Arg Thr Ile Ser Lys Ala Arg
                100                 105                 110
```

-continued

<210> SEQ ID NO 8
<211> LENGTH: 109
<212> TYPE: PRT
<213> ORGANISM: Canis familiaris

<400> SEQUENCE: 8

Gly Gln Ala His Gln Pro Ser Val Tyr Val Leu Pro Pro Ser Arg Glu
1               5                   10                  15

Glu Leu Ser Lys Asn Thr Val Ser Leu Thr Cys Leu Ile Lys Asp Phe
            20                  25                  30

Phe Pro Pro Asp Ile Asp Val Glu Trp Gln Ser Asn Gly Gln Gln Glu
        35                  40                  45

Pro Glu Ser Lys Tyr Arg Thr Thr Pro Pro Gln Leu Asp Glu Asp Gly
    50                  55                  60

Ser Tyr Phe Leu Tyr Ser Lys Leu Ser Val Asp Lys Ser Arg Trp Gln
65                  70                  75                  80

Arg Gly Asp Thr Phe Ile Cys Ala Val Met His Glu Ala Leu His Asn
                85                  90                  95

His Tyr Thr Gln Glu Ser Leu Ser His Ser Pro Gly Lys
            100                 105

<210> SEQ ID NO 9
<211> LENGTH: 291
<212> TYPE: DNA
<213> ORGANISM: Canis familiaris

<400> SEQUENCE: 9
gcctcaacaa ctgctcctag cgtgtttccc ctggccccta gctgcggaag tacctcaggc      60
agcacagtgg ccctggcttg tctggtgtct ggatatttcc ctgagccagt gaccgtgagt     120
tggaacagcg gctctctgac ctccggggtg cacacatttc catctgtgct gcagtctagt     180
ggcctgtact ccctgtcaag catggtgact gtgccttcct ctaggtggcc atcagaaact     240
ttcacctgca acgtggccca tcccgccagc aagaccaaag tggacaagcc c              291

<210> SEQ ID NO 10
<211> LENGTH: 57
<212> TYPE: DNA
<213> ORGANISM: Canis familiaris

<400> SEQUENCE: 10
gtgcctaaaa gggagaatgg aagggtgcca agaccacctg attgccctaa gtgtcca         57

<210> SEQ ID NO 11
<211> LENGTH: 330
<212> TYPE: DNA
<213> ORGANISM: Canis familiaris

<400> SEQUENCE: 11
gctccagaaa tgctgggagg accaagcgtg ttcatctttc acccaagcc caaagacaca       60 ctgctgattg ctagaactcc cgaggtgacc tgcgtggtgg tggacctgga tccagaggac     120
cccgaagtgc agatctcctg gttcgtggat gggaagcaga tgcagacagc caaaactcag     180
cctcgggagg aacagtttaa cggaacctat agagtggtgt ctgtgctgcc aattggacac     240
caggactggc tgaagggcaa acagtttaca tgcaaggtga acaacaaggc cctgcctagt     300
ccaatcgaga ggactatttc aaaagctagg                                      330

<210> SEQ ID NO 12
<211> LENGTH: 327
<212> TYPE: DNA
<213> ORGANISM: Canis familiaris

<400> SEQUENCE: 12
ggacaggctc atcagccttc cgtgtatgtg ctgcctccat cccgggagga actgtctaag        60
aacacagtga gtctgacttg tctgatcaaa gatttctttc cccctgacat tgatgtggag       120
tggcagagca atgggcagca ggagccagaa tccaagtaca gaaccacacc accccagctg       180
gacgaagatg gctcctattt cctgtacagt aagctgtcag tggacaaatc taggtggcag       240
cgcggggata cctttatctg cgccgtgatg cacgaggctc tgcacaatca ttacacacaa       300
gaaagtctgt cacatagccc cggcaag                                           327

<210> SEQ ID NO 13
<211> LENGTH: 5
<212> TYPE: PRT
<213> ORGANISM: Mus musculus

<400> SEQUENCE: 13

Tyr Tyr Asp Ile Asn
1               5

<210> SEQ ID NO 14
<211> LENGTH: 5
<212> TYPE: PRT
<213> ORGANISM: Mus musculus

<400> SEQUENCE: 14

Asn Tyr Gly Met Ser
1               5

<210> SEQ ID NO 15
<211> LENGTH: 17
<212> TYPE: PRT
<213> ORGANISM: Mus musculus

<400> SEQUENCE: 15

Trp Ile Phe Pro Gly Asp Gly Gly Thr Lys Tyr Asn Glu Thr Phe Lys
1               5                   10                  15

Gly

<210> SEQ ID NO 16
<211> LENGTH: 17
<212> TYPE: PRT
<213> ORGANISM: Mus musculus

<400> SEQUENCE: 16

Thr Ile Ser Tyr Gly Gly Ser Tyr Thr Tyr Tyr Pro Asp Asn Ile Lys
1               5                   10                  15

Gly

<210> SEQ ID NO 17
<211> LENGTH: 14
<212> TYPE: PRT
<213> ORGANISM: Mus musculus

<400> SEQUENCE: 17

Ala Arg Gly Gly Thr Ser Val Ile Arg Asp Ala Met Asp Tyr
1               5                   10

-continued

```
<210> SEQ ID NO 18
<211> LENGTH: 11
<212> TYPE: PRT
<213> ORGANISM: Mus musculus

<400> SEQUENCE: 18

Val Arg Gly Tyr Gly Tyr Asp Thr Met Asp Tyr
1               5               10

<210> SEQ ID NO 19
<211> LENGTH: 15
<212> TYPE: PRT
<213> ORGANISM: Mus musculus

<400> SEQUENCE: 19

Arg Ala Ser Glu Ser Val Asp Asn Tyr Gly Ile Ser Phe Met His
1               5               10              15

<210> SEQ ID NO 20
<211> LENGTH: 15
<212> TYPE: PRT
<213> ORGANISM: Mus musculus

<400> SEQUENCE: 20

Lys Ala Ser Gln Ser Val Ser Phe Ala Gly Thr Gly Leu Met His
1               5               10              15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 7
<212> TYPE: PRT
<213> ORGANISM: Mus musculus

<400> SEQUENCE: 22

Arg Ala Ser Asn Leu Glu Ala
1               5

<210> SEQ ID NO 23
<211> LENGTH: 9
<212> TYPE: PRT
<213> ORGANISM: Mus musculus

<400> SEQUENCE: 23

Gln Gln Ser Asn Lys Asp Pro Leu Thr
1               5

<210> SEQ ID NO 24
<211> LENGTH: 9
<212> TYPE: PRT
<213> ORGANISM: Mus musculus

<400> SEQUENCE: 24

Gln Gln Ser Arg Glu Tyr Pro Trp Thr
1               5

<210> SEQ ID NO 25
<211> LENGTH: 111
```

```
<212> TYPE: PRT
<213> ORGANISM: Mus musculus

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Glu Leu Lys
            100                 105                 110

<210> SEQ ID NO 26
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 26

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 27
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 27

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Phe Gln Gln Lys Pro Gly Gln Ser Pro
        35                  40                  45

Gln Leu Leu Ile Tyr Arg Ala Ser Asn Leu Glu Ser Gly Val Pro Asp
```

-continued

```
            50              55              60

Arg Phe Ser Gly Ser Gly Ser Gly Thr Asp Phe Thr Leu Arg Ile Ser
65              70              75              80

Arg Val Glu Ala Asp Asp Ala Gly Val Tyr Tyr Cys Gln Gln Ser Asn
                85              90              95

Lys Asp Pro Leu Thr Phe Gly Ala Gly Thr Lys Leu Glu Ile Lys
            100             105             110

<210> SEQ ID NO 28
<211> LENGTH: 111
<212> TYPE: PRT
<213> ORGANISM: Mus musculus

<400> SEQUENCE: 28

Asp Ile Leu Leu Thr Gln Ser Pro Ala Ser Leu Ala Val Ser Leu Gly
1               5               10              15

Gln Arg Ala Ile Ile Ser Cys Lys Ala Ser Gln Ser Val Ser Phe Ala
                20              25              30

Gly Thr Gly Leu Met His Trp Tyr Gln Gln Lys Pro Gly Gln Gln Pro
            35              40              45

Lys Leu Leu Ile Tyr Arg Ala Ser Asn Leu Glu Ala Gly Val Pro Thr
    50              55              60

Arg Phe Ser Gly Ser Gly Ser Arg Thr Asp Phe Thr Leu Asn Ile His
65              70              75              80

Pro Val Glu Glu Glu Asp Ala Ala Thr Tyr Phe Cys Gln Gln Ser Arg
                85              90              95

Glu Tyr Pro Trp Thr Phe Gly Gly Gly Thr Lys Leu Glu Ile Lys
            100             105             110

<210> SEQ ID NO 29
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 29

Glu Ile Val Met Thr Gln Ser Pro Ala Ser Leu Ser Leu Ser Gln Glu
1               5               10              15

Glu Lys Val Thr Ile Thr Cys Lys Ala Ser Gln Ser Val Ser Phe Ala
                20              25              30

Gly Thr Gly Leu Met His Trp Tyr Gln Gln Lys Pro Gly Gln Ala Pro
            35              40              45

Lys Leu Leu Ile Tyr Arg Ala Ser Asn Leu Glu Ala Gly Val Pro Ser
    50              55              60

Arg Phe Ser Gly Ser Gly Ser Gly Thr Asp Phe Ser Phe Thr Ile Ser
65              70              75              80

Ser Leu Glu Pro Glu Asp Val Ala Val Tyr Tyr Cys Gln Gln Ser Arg
                85              90              95

Glu Tyr Pro Trp Thr Phe Gly Gln Gly Thr Lys Leu Glu Ile Lys
            100             105             110

<210> SEQ ID NO 30
<211> LENGTH: 121
<212> TYPE: PRT
<213> ORGANISM: Mus musculus

<400> SEQUENCE: 30
```

-continued

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Lys Tyr Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Gly Thr Lys Tyr Asn Glu Thr Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gly Gly Thr Ser Val Ile Arg Asp Ala Met Asp Tyr Trp Gly
            100                 105                 110

Gln Gly Thr Ser Val Thr Val Ser Ser
        115                 120
```

```
<210> SEQ ID NO 31
<211> LENGTH: 121
<212> TYPE: PRT
<213> ORGANISM: Artificial
<220> FEATURE:
<223> OTHER INFORMATION: caninized variable heavy chain mAb sequence,
      from Mus musculus and Canis

<400> SEQUENCE: 31
```

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Lys Tyr Tyr
            20                  25                  30

Asp Ile Asn Trp Val Arg Gln Ala Pro Gly Ala Gly Leu Asp Trp Met
        35                  40                  45

Gly Trp Ile Phe Pro Gly Asp Gly Gly Thr Lys Tyr Asn Glu Thr Phe
    50                  55                  60

Lys Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Gly Thr Ser Val Ile Arg Asp Ala Met Asp Tyr Trp Gly
            100                 105                 110

Gln Gly Thr Leu Val Thr Val Ser Ser
        115                 120
```

```
<210> SEQ ID NO 32
<211> LENGTH: 118
<212> TYPE: PRT
<213> ORGANISM: Mus musculus

<400> SEQUENCE: 32
```

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Ser Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Tyr Gly Gly Ser Tyr Thr Tyr Tyr Pro Asp Asn Ile
    50                  55                  60
```

```
Lys Gly Arg Phe Thr Ile Ser Arg Asp Asn Ala Lys Asn Thr Leu Tyr
65              70              75              80

Leu Gln Met Ser Ser Leu Lys Ser Glu Asp Thr Ala Met Tyr Tyr Cys
            85              90              95

Val Arg Gly Tyr Gly Tyr Asp Thr Met Asp Tyr Trp Gly Gln Gly Thr
        100             105             110

Ser Val Thr Val Ser Ser
    115

<210> SEQ ID NO 33
<211> LENGTH: 118
<212> TYPE: PRT
<213> ORGANISM: Artificial
<220> FEATURE:
<223> OTHER INFORMATION: caninized variable heavy chain mAb sequence,
     from Mus musculus and Canis

<400> SEQUENCE: 33

Glu Val Gln Leu Val Glu Ser Gly Gly Asp Leu Val Lys Pro Gly Gly
1               5               10              15

Ser Leu Arg Leu Ser Cys Val Ala Ser Gly Phe Thr Phe Ser Asn Tyr
            20              25              30

Gly Met Ser Trp Val Arg Gln Ala Pro Gly Lys Gly Leu Gln Trp Val
        35              40              45

Ala Thr Ile Ser Tyr Gly Gly Ser Tyr Thr Tyr Tyr Pro Asp Asn Ile
    50              55              60

Lys Gly Arg Phe Thr Ile Ser Arg Asp Asn Ala Lys Asn Thr Leu Tyr
65              70              75              80

Leu Gln Met Asn Ser Leu Arg Ala Glu Asp Thr Ala Met Tyr Tyr Cys
            85              90              95

Val Arg Gly Tyr Gly Tyr Asp Thr Met Asp Tyr Trp Gly Gln Gly Thr
        100             105             110

Leu Val Thr Val Ser Ser
    115

<210> SEQ ID NO 34
<211> LENGTH: 159
<212> TYPE: PRT
<213> ORGANISM: Canis familiaris

<400> SEQUENCE: 34

Met Leu Ser His Thr Gly Pro Ser Arg Phe Ala Leu Phe Leu Leu Cys
1               5               10              15

Ser Met Glu Thr Leu Leu Ser Ser His Met Ala Pro Thr His Gln Leu
            20              25              30

Pro Pro Ser Asp Val Arg Lys Ile Ile Leu Glu Leu Gln Pro Leu Ser
        35              40              45

Arg Gly Leu Leu Glu Asp Tyr Gln Lys Lys Glu Thr Gly Val Pro Glu
    50              55              60

Ser Asn Arg Thr Leu Leu Leu Cys Leu Thr Ser Asp Ser Gln Pro Pro
65              70              75              80

Arg Leu Asn Ser Ser Ala Ile Leu Pro Tyr Phe Arg Ala Ile Arg Pro
            85              90              95

Leu Ser Asp Lys Asn Ile Ile Asp Lys Ile Ile Glu Gln Leu Asp Lys
            100             105             110

Leu Lys Phe Gln His Glu Pro Glu Thr Glu Ile Ser Val Pro Ala Asp
            115             120             125
```

-continued

Thr Phe Glu Cys Lys Ser Phe Ile Leu Thr Ile Leu Gln Gln Phe Ser
    130                 135                 140

Ala Cys Leu Glu Ser Val Phe Lys Ser Leu Asn Ser Gly Pro Gln
145                 150                 155

<210> SEQ ID NO 35
<211> LENGTH: 477
<212> TYPE: DNA
<213> ORGANISM: Canis familiaris

<400> SEQUENCE: 35
atgctctccc acacaggacc atccaggttt gccctgttcc tgctctgctc tatggaaacc        60
ttgctgtcct cccatatggc acccacccat cagctaccac caagtgatgt acgaaaaatc       120
atcttggaat tacagccctt gtcgaggga cttttggaag actatcagaa gaaagagaca        180 gggtgccag aatccaaccg taccttgctg ctgtgtctca cctctgattc ccaaccacca        240
cgcctcaaca gctcagccat cttgccttat ttcagggcaa tcagaccatt atcagataag        300
aacattattg ataaaatcat agaacagctt gacaaactca aatttcaaca tgaaccagaa        360
acagaaattt ctgtgcctgc agatacttttt gaatgtaaaa gcttcatctt gacgatttta       420
cagcagttct cggcgtgcct ggaaagtgtg tttaagtcac taaactctgg acctcag          477

<210> SEQ ID NO 36
<211> LENGTH: 333
<212> TYPE: DNA
<213> ORGANISM: Mus musculus

<400> SEQUENCE: 36
gacattgtgc tgacccaatc tccagcttct ttggctgtgt ctctagggca gagggccacc        60
atctcctgca gagccagcga aagtgttgat aattatggca ttagtttat gcactggtac        120 cagcagaaac caggacagcc acccaaactc ctcatctatc gtgcatccaa cctagaatct        180
gggatccctg ccaggttcag tggcagtggg tctaggacag acttcaccct caccattaat        240
cctgtggaga ctgatgatgt tgcaacctat tactgtcagc aaagtaataa ggatccgctc        300
acgttcggtg ctgggaccaa gctggagctg aaa                                    333

<210> SEQ ID NO 37
<211> LENGTH: 363
<212> TYPE: DNA
<213> ORGANISM: Mus musculus

<400> SEQUENCE: 37
caggttcagc tgcagcagtc tggagctgaa ctggtaaagc ctggggcttc agtgaagttg        60
tcctgcaagg cttctggcta caccttcaaa tactatgata taaactgggt gaggcagagg       120
cctgaacagg gacttgagtg gattggatgg attttttcctg gagatggtgg tactaagtac      180
aatgagacgt tcaagggcaa ggccacactg actacagaca atcctccag cacagcctac        240 atgcagctca gcaggctgac atctgaggac tctgctgtct atttctgtgc aagaggggggg      300 acttcggtga taagggatgc tatggactac tggggtcaag gaacctcagt caccgtctcc       360
tca                                                                     363

<210> SEQ ID NO 38
<211> LENGTH: 333
<212> TYPE: DNA
<213> ORGANISM: Mus musculus

```
<400> SEQUENCE: 38
gacattttgc tgacccaatc tccagcttct ttggctgtgt ctctagggca gagggccatc        60
atctcctgca aggccagcca aagtgtcagt tttgctggta ctggtttaat gcactggtac       120
caacagaaac caggacagca acccaaactc ctcatctatc gtgcatccaa cctagaagct       180
ggggttccta ccaggtttag tggcagtggg tctaggacag acttcaccct caatatccat       240
cctgtggagg aggaggatgc tgcaacctat ttctgtcagc aaagcaggga atatccgtgg       300
acgttcggtg gaggcaccaa gctggaaatc aaa                                    333

<210> SEQ ID NO 39
<211> LENGTH: 353
<212> TYPE: DNA
<213> ORGANISM: Mus musculus

<400> SEQUENCE: 39
gaggtgcagt tggtggagtc tggggggagac ttagtgaagc ctggagggtc cctgaaactc       60
tcctgtgcag cctctggatt ctctttcagt aactatggca tgtcttgggt tcgccagact      120
ccagacaaga ggctggagtg ggtcgcaacc attagttatg gtggtagtta cacctactat      180
ccagacaata taaaggggcg attcaccatc tccagagaca atgccaagaa caccctgtac      240
ctgcaaatga gcagtctgaa gtctgaggac acagccatgt attactgtgt aaggggggtat      300 ggttacgata ctatggacta ctggggtcaa ggaacctcag tcaccgtctc gag             353

<210> SEQ ID NO 40
<211> LENGTH: 331
<212> TYPE: PRT
<213> ORGANISM: Canis familiaris

<400> SEQUENCE: 40

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Phe Asn Glu Cys Arg Cys Thr Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
    130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Ser Arg Glu Gln Gln
                165                 170                 175

Phe Asn Gly Thr Tyr Arg Val Val Ser Val Leu Pro Ile Glu His Gln
                180                 185                 190

Asp Trp Leu Thr Gly Lys Glu Phe Lys Cys Arg Val Asn His Ile Asp
```

-continued

```
            195              200              205
Leu Pro Ser Pro Ile Glu Arg Thr Ile Ser Lys Ala Arg Gly Arg Ala
    210              215              220

His Lys Pro Ser Val Tyr Val Leu Pro Pro Ser Pro Lys Glu Leu Ser
225              230              235              240

Ser Ser Asp Thr Val Ser Ile Thr Cys Leu Ile Lys Asp Phe Tyr Pro
            245              250              255

Pro Asp Ile Asp Val Glu Trp Gln Ser Asn Gly Gln Gln Glu Pro Glu
            260              265              270

Arg Lys His Arg Met Thr Pro Pro Gln Leu Asp Glu Asp Gly Ser Tyr
            275              280              285

Phe Leu Tyr Ser Lys Leu Ser Val Asp Lys Ser Arg Trp Gln Gln Gly
    290              295              300

Asp Pro Phe Thr Cys Ala Val Met His Glu Thr Leu Gln Asn His Tyr
305              310              315              320

Thr Asp Leu Ser Leu Ser His Ser Pro Gly Lys
            325              330
```

```
<210> SEQ ID NO 41
<211> LENGTH: 993
<212> TYPE: DNA
<213> ORGANISM: Canis familiaris

<400> SEQUENCE: 41
gcctccacca cggcgccctc ggttttccca ctggcccccca gctgcgggtc cacttccggc       60
tccacggtgg ccctggcctg cctggtgtca ggctacttcc ccgagcctgt aactgtgtcc      120
tggaactccg gctccttgac cagcggtgtg cacaccttcc cgtccgtcct gcagtcctca      180
gggcttcact ccctcagcag catggtgaca gtgccctcca gcaggtggcc cagcgagacc      240
ttcacctgca acgtggtcca cccagccagc aacactaaag tagacaagcc agtgttcaat      300
gaatgcagat gcactgatac accccccatgc ccagtccctg aacctctggg agggccttcg      360
gtcctcatct ttcccccgaa acccaaggac atcctcagga ttacccgaac acccgaggtc      420
acctgtgtgg tgttagatct gggccgtgag gaccctgagg tgcagatcag ctggttcgtg      480
gatggtaagg aggtgcacac agccaagacc cagtctcgtg agcagcagtt caacggcacc      540
taccgtgtgg tcagcgtcct ccccattgag caccaggact ggctcacagg gaaggagttc      600
aagtgcagag tcaaccacat agacctcccg tctcccatcg agaggaccat ctctaaggcc      660
agagggaggg cccataagcc cagtgtgtat gtcctgccgc catccccaaa ggagttgtca      720
tccagtgaca cagtcagcat cacctgcctg ataaaagact ctacccacc tgacattgat      780 gtggagtggc agagcaatgg acagcaggag cccgagagga gcaccgcat gaccccgccc      840 cagctggacg aggacgggtc ctacttcctg tacagcaagc tctctgtgga caagagccgc      900
tggcagcagg agacccctt cacatgtgcg gtgatgcatg aaactctaca gaaccactac      960
acagatctat ccctctccca ttctccgggt aaa                                   993
```

```
<210> SEQ ID NO 42
<211> LENGTH: 335
<212> TYPE: PRT
<213> ORGANISM: Canis familiaris

<400> SEQUENCE: 42
```

```
Ala Ser Thr Thr Ala Pro Ser Val Phe Pro Leu Ala Pro Ser Cys Gly
1                5                10               15
```

```
Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
            50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                    85                  90                  95

Pro Val Pro Lys Arg Glu Asn Gly Arg Val Pro Arg Pro Pro Asp Cys
                100                 105                 110

Pro Lys Cys Pro Ala Pro Glu Met Leu Gly Gly Pro Ser Val Phe Ile
                115                 120                 125

Phe Pro Pro Lys Pro Lys Asp Thr Leu Leu Ile Ala Arg Thr Pro Glu
            130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
                180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
            210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
                260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
            290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

<210> SEQ ID NO 43
<211> LENGTH: 1005
<212> TYPE: DNA
<213> ORGANISM: Canis familiaris

<400> SEQUENCE: 43

```
gcctcaacaa ctgctcctag cgtgtttccc ctggcccta gctgcggaag tacctcaggc        60
agcacagtgg ccctggcttg tctggtgtct ggatatttcc ctgagccagt gaccgtgagt       120
tggaacagcg gctctctgac ctccggggtg cacacatttc catctgtgct gcagtctagt       180
ggcctgtact ccctgtcaag catggtgact gtgccttcct ctaggtggcc atcagaaact       240
ttcacctgca acgtggccca tcccgccagc aagaccaaag tggacaagcc cgtgcctaaa       300
agggagaatg gaagggtgcc aagaccacct gattgcccta gtgtccagc tccagaaatg        360
```

```
ctgggaggac caagcgtgtt catctttcca cccaagccca aagacacact gctgattgct      420
agaactcccg aggtgacctg cgtggtggtg gacctggatc cagaggaccc cgaagtgcag      480
atctcctggt tcgtggatgg gaagcagatg cagacagcca aaactcagcc tcgggaggaa      540
cagtttaacg gaacctatag agtggtgtct gtgctgccaa ttggacacca ggactggctg      600
aagggcaaac agtttacatg caaggtgaac aacaaggccc tgcctagtcc aatcgagagg      660
actatttcaa aagctagggg acaggctcat cagccttccg tgtatgtgct gcctccatcc      720
cgggaggaac tgtctaagaa cacagtgagt ctgacttgtc tgatcaaaga tttctttccc      780
cctgacattg atgtggagtg gcagagcaat gggcagcagg agccagaatc caagtacaga      840
accacaccac cccagctgga cgaagatggc tcctatttcc tgtacagtaa gctgtcagtg      900
gacaaatcta ggtggcagcg cggggatacc tttatctgcg ccgtgatgca cgaggctctg      960
cacaatcatt acacacaaga aagtctgtca catagccccg gcaag                     1005
```

<210> SEQ ID NO 44
<211> LENGTH: 106
<212> TYPE: PRT
<213> ORGANISM: Canis familiaris

<400> SEQUENCE: 44

```
Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Gln Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105
```

<210> SEQ ID NO 45
<211> LENGTH: 318
<212> TYPE: DNA
<213> ORGANISM: Canis familiaris

<400> SEQUENCE: 45

```
aggaacgacg cccagcctgc tgtgtatctg tttcagccct cccctgatca gctgcacact       60
ggctctgcta gtgtggtgtg tctgctgaac agcttctacc caaaggatat caatgtgaag      120
tggaaagtgg acggcgtgat ccaggatact gggattcagg agtccgtgac cgaacaggac      180
aaagattcaa catatagcct gagctccact ctgaccatgt ctagtaccga gtacctgagc      240
cacgaactgt attcctgcga gatcactcat aagtccctgc cctctaccct gatcaagagc      300
ttccagagat cagagtgt                                                    318
```

<210> SEQ ID NO 46
<211> LENGTH: 333
<212> TYPE: DNA
<213> ORGANISM: Artificial
<220> FEATURE:
<223> OTHER INFORMATION: nucleotide sequence encoding a caninized -continued variable light chain mAb sequence, from Mus musculus and Canis

<400> SEQUENCE: 46
gagatcgtga tgacccagag ccccgccagc ctgagcctga gccaggaaga gaaagtcacc      60
atcacatgca aggccagcca gagcgtgtcc ttcgccggca caggcctgat gcactggtat     120
cagcagaagc ccggccaggc ccccaagctg ctgatctacc gggccagcaa cctggaagcc     180
ggcgtgccaa gcagattcag cggcagcggc tccggcaccg acttcagctt caccatcagc     240
agcctcgaac ccgaggacgt ggccgtgtac tactgccagc agagcagaga gtacccctgg     300
accttcggcc agggtaccaa gctggagatc aag                                  333

<210> SEQ ID NO 47
<211> LENGTH: 354
<212> TYPE: DNA
<213> ORGANISM: Artificial
<220> FEATURE:
<223> OTHER INFORMATION: nucleotide sequence encoding a caninized
      variable heavy chain mAb sequence, from Mus musculus and Canis

<400> SEQUENCE: 47
gaggtgcagc tggtggaatc tggcggcgac ctggtcaagc ctggcggcag cctgagactg      60
agctgtgtgg ccagcggctt caccttcagc aactacggca tgagctgggt ccgacaggcc     120
cctggcaagg gactgcagtg ggtggccacc atcagctacg gcggcagcta cacctactac     180
cccgacaaca tcaagggccg gttcaccatc agccgggaca cgccaagaa caccctgtac      240 ctgcagatga cagcctgcg ggccgaggac accgccatgt actactgcgt gcggggctac      300
ggctacgaca caatggacta ctggggccag ggcacccctcg tgaccgtctc gagc           354

<210> SEQ ID NO 48
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 48
gatatagtga tgacacaaac tcctctcagt ctttccgtat caccgggaga accggcttcc      60
atttcctgtc gggcctcaga gtctgtggac aactacggga tatccttcat gcactggtat     120
cagcagaaac ccggccagcc ccctaaactc cttatttaca gggccagtaa tctggaaagc     180
ggtgtgcccg atcgatttag cggttccggg agcggcacag atttcaccct gcgaatctct     240
agagttgaag cggatgatgc aggagtatat tactgccagc aatccaataa ggatccccttt   300 acattcggcg cgggtaccaa gctggagatc aag                                  333

<210> SEQ ID NO 49
<211> LENGTH: 363
<212> TYPE: DNA
<213> ORGANISM: Artificial
<220> FEATURE:
<223> OTHER INFORMATION: nucleotide sequence encoding a caninized
      variable heavy chain mAb sequence, from Mus musculus and Canis

<400> SEQUENCE: 49
gaggtgcagc tggtgcagtc tggcgccgaa gtgaagaaac ctggcgccag cgtgaaggtg      60
tcctgcaaga ccagcggcta caccttcaag tactacgaca tcaactgggt ccgacaggcc     120
cctggcgccg gactggattg gatgggctgg atcttccccg gcgacggcgg caccaagtac     180

-continued

```
aacgagacat tcaagggcag agtgaccctg accgccgaca ccagcaccag caccgcctac        240
atggaactga gcagcctgag agccggcgat atcgctgtgt actactgcgc cagaggcggc        300
accagcgtga tccgggacgc tatggactac tggggccagg gcaccctcgt gaccgtctcg        360
agc                                                                     363

<210> SEQ ID NO 50
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 50
gacattgtta tgactcagac gcccctgagc ctgagcgtct cccccggcga gcccgctagt         60
attagttgcc gggcatccga gtcagtggac aattatggca tcagctttat gcattggttt        120
cagcagaaac caggtcagtc ccctcaactc ctgatttaca gagcttccaa tctggaatca        180
ggcgttcctg acagatttag cggatcaggc tccgggacag atttcaccct cgcgcatcagt        240 cgcgtggaag ccgatgacgc aggcgtctat tattgtcaac agtccaacaa ggatccccctt        300 acattcggag ccggtaccaa gctggagatc aag                                     333

<210> SEQ ID NO 51
<211> LENGTH: 111
<212> TYPE: PRT
<213> ORGANISM: Artificial
<220> FEATURE:
<223> OTHER INFORMATION: caninized variable light chain mAb sequence,
      from Mus musculus and Canis

<400> SEQUENCE: 51

Asp Ile Val Met Thr Gln Thr Pro Leu Ser Leu Ser Val Ser Pro Gly
1               5                   10                  15

Glu Pro Ala Ser Ile Ser Cys Arg Ala Ser Glu Ser Val Asp Asn Tyr
            20                  25                  30

Gly Ile Ser Phe Met His Trp Phe Gln Gln Lys Pro Gly Gln Ser Pro
        35                  40                  45

Gln Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln Gln Ser Asn
                85                  90                  95

Lys Asp Pro Leu Thr Phe Gly Ala Gly Thr Lys Leu Glu Ile Lys
            100                 105                 110

<210> SEQ ID NO 52
<211> LENGTH: 333
<212> TYPE: DNA
<213> ORGANISM: Artificial
<220> FEATURE:
<223> OTHER INFORMATION: nucleotide sequence encoding a caninized
      variable light chain mAb sequence, from Mus musculus and Canis

<400> SEQUENCE: 52
gacatcgtga tgacccagac ccccctgagc ctgagcgtgt ccctggcga gcctgccagc          60 atcagctgca gagccagcga gagcgtggac aactacggca tcagcttcat gcactggttc        120
cagcagaagc ccggccagag cccccagcgg ctgatctaca gagccagcaa cctggaaagc        180
```

-continued

```
ggcgtgcccg atcggtttag cggctctggc agcggcaccg acttcaccct gcggatctct      240
cgggtggaag ccgatgacgc cggagtgtac tactgccagc agagcaacaa ggaccccctg      300
acctttggcg ccggtaccaa gctggagatc aag                                   333
```

```
<210> SEQ ID NO 53
<211> LENGTH: 148
<212> TYPE: PRT
<213> ORGANISM: Artificial
<220> FEATURE:
<223> OTHER INFORMATION: canine IL-31 full length protein encoded by
      codon-optimized nucleotide sequence

<400> SEQUENCE: 53

Met Arg Gly Ser His His His His His His Gly Ser Ser His Met Ala
1               5                   10                  15

Pro Thr His Gln Leu Pro Pro Ser Asp Val Arg Lys Ile Ile Leu Glu
            20                  25                  30

Leu Gln Pro Leu Ser Arg Gly Leu Leu Glu Asp Tyr Gln Lys Lys Glu
        35                  40                  45

Thr Gly Val Pro Glu Ser Asn Arg Thr Leu Leu Leu Cys Leu Thr Ser
    50                  55                  60

Asp Ser Gln Pro Pro Arg Leu Asn Ser Ser Ala Ile Leu Pro Tyr Phe
65                  70                  75                  80

Arg Ala Ile Arg Pro Leu Ser Asp Lys Asn Ile Ile Asp Lys Ile Ile
                85                  90                  95

Glu Gln Leu Asp Lys Leu Lys Phe Gln His Glu Pro Glu Thr Glu Ile
            100                 105                 110

Ser Val Pro Ala Asp Thr Phe Glu Cys Lys Ser Phe Ile Leu Thr Ile
        115                 120                 125

Leu Gln Gln Phe Ser Ala Cys Leu Glu Ser Val Phe Lys Ser Leu Asn
    130                 135                 140

Ser Gly Pro Gln
145
```

```
<210> SEQ ID NO 54
<211> LENGTH: 444
<212> TYPE: DNA
<213> ORGANISM: Artificial
<220> FEATURE:
<223> OTHER INFORMATION: codon-optimized nucleotide sequence encoding
      canine IL-31 full-length protein

<400> SEQUENCE: 54
atgagaggat cccatcacca tcaccaccac ggctcatctc atatggctcc tactcaccaa       60
ttaccaccct ccgatgtccg taaaattatt ctcgaattac aacctttatc ccgcggtctg      120
ctcgaagatt accaaaaaaa agaaacaggc gtcccagaaa gcaaccgtac attactcctt      180
tgccttacct ccgattccca accacctcgt cttaactcat cagccattct cccttatttc      240
cgtgccattc gccctctttc tgataaaaat attattgaca aaattattga caactcgac       300 aaattaaaat tccaacacga acccgaaacc gaaatctccg tacctgccga taccttttgaa     360 tgcaaatcct ttatcctcac tattttacaa caattctccg catgtctcga atccgtcttc      420
aaatctctca attccggtcc acag                                             444
```

```
<210> SEQ ID NO 55
<211> LENGTH: 375
<212> TYPE: DNA
```

-continued

<213> ORGANISM: Artificial Sequence
<220> FEATURE:
<223> OTHER INFORMATION: ZTS-841 Heavy Chain Variable Region

<400> SEQUENCE: 55
gaggtgcagc tggtggagtc tgggggagat ttggtgaagc ctggggggtc cttgagactg      60
tcctgtgtgg cctctggatt caccttcagt agccacggca tgcactgggt ccgtcagtct     120
ccagggaagg gactgcagtg ggtcgcagtt attaacagcg gtggaagtag cacatactac     180
acagacgctg tgaagggccg attcaccatc tccagagaca cgccaagaa cacagtgtat      240 ctacagatga acagcctgag agccgaggac acggccatgt attactgtgc aaaggagtcc     300 gtcgggggt gggagcaact ggtcggacct cattttgact actggggcca gggaaccctg      360
gtcatcgtct cgagc                                                      375

<210> SEQ ID NO 56
<211> LENGTH: 125
<212> TYPE: PRT
<213> ORGANISM: Artificial Sequence
<220> FEATURE:
<223> OTHER INFORMATION: ZTS-841 Heavy Chain Variable Region

<400> SEQUENCE: 56

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Ser His
            20                  25                  30

Gly Met His Trp Val Arg Gln Ser Pro Gly Lys Gly Leu Gln Trp Val
        35                  40                  45

Ala Val Ile Asn Ser Gly Gly Ser Ser Thr Tyr Tyr Thr Asp Ala Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Met Tyr Tyr Cys
                85                  90                  95

Ala Lys Glu Ser Val Gly Gly Trp Glu Gln Leu Val Gly Pro His Phe
            100                 105                 110

Asp Tyr Trp Gly Gln Gly Thr Leu Val Ile Val Ser Ser
        115                 120                 125

<210> SEQ ID NO 57
<211> LENGTH: 8
<212> TYPE: PRT
<213> ORGANISM: Canis familiaris

<400> SEQUENCE: 57

Gly Phe Thr Phe Ser Ser His Gly
1               5

<210> SEQ ID NO 58
<211> LENGTH: 8
<212> TYPE: PRT
<213> ORGANISM: Canis familiaris

<400> SEQUENCE: 58

Ile Asn Ser Gly Gly Ser Ser Thr
1               5

<210> SEQ ID NO 59
<211> LENGTH: 18

<212> TYPE: PRT
<213> ORGANISM: Canis familiaris

<400> SEQUENCE: 59

Ala Lys Glu Ser Val Gly Gly Trp Glu Gln Leu Val Gly Pro His Phe
1               5                   10                  15

Asp Tyr

<210> SEQ ID NO 60
<211> LENGTH: 330
<212> TYPE: DNA
<213> ORGANISM: Artificial Sequence
<220> FEATURE:
<223> OTHER INFORMATION: ZTS-841 Light Chain Variable Region

<400> SEQUENCE: 60
cagtctgtgc tgactcagcc gacctcagtg tcagggtccc ttggccagag ggtcaccatc        60
tcctgctctg gaagcacgaa caacatcggt attcttggtg cgagctggta ccaactgttc       120
ccaggaaagg cccctaaact cctcgtgtac ggtaatggga atcgaccgtc aggggtccct       180
gaccggtttt ccggcgccga ctctggcgac tcagtcaccc tgaccatcac tgggcttcag       240
gctgaggacg aggctgatta ttactgccag tcctttgata ccacgcttgg tgctcatgtg       300
ttcggcggag gcacccacct gaccgtcctt                                        330

<210> SEQ ID NO 61
<211> LENGTH: 110
<212> TYPE: PRT
<213> ORGANISM: Artificial Sequence
<220> FEATURE:
<223> OTHER INFORMATION: ZTS-841 Light Chain Variable Region

<400> SEQUENCE: 61

Gln Ser Val Leu Thr Gln Pro Thr Ser Val Ser Gly Ser Leu Gly Gln
1               5                   10                  15

Arg Val Thr Ile Ser Cys Ser Gly Ser Thr Asn Asn Ile Gly Ile Leu
                20                  25                  30

Gly Ala Ser Trp Tyr Gln Leu Phe Pro Gly Lys Ala Pro Lys Leu Leu
        35                  40                  45

Val Tyr Gly Asn Gly Asn Arg Pro Ser Gly Val Pro Asp Arg Phe Ser
    50                  55                  60

Gly Ala Asp Ser Gly Asp Ser Val Thr Leu Thr Ile Thr Gly Leu Gln
65                  70                  75                  80

Ala Glu Asp Glu Ala Asp Tyr Tyr Cys Gln Ser Phe Asp Thr Thr Leu
                85                  90                  95

Gly Ala His Val Phe Gly Gly Gly Thr His Leu Thr Val Leu
            100                 105                 110

<210> SEQ ID NO 62
<211> LENGTH: 8
<212> TYPE: PRT
<213> ORGANISM: Canis familiaris

<400> SEQUENCE: 62

Thr Asn Asn Ile Gly Ile Leu Gly
1               5

<210> SEQ ID NO 63
<211> LENGTH: 4
<212> TYPE: PRT
<213> ORGANISM: Canis familiaris -continued

<400> SEQUENCE: 63

Gly Asn Gly Asn
1

<210> SEQ ID NO 64
<211> LENGTH: 11
<212> TYPE: PRT
<213> ORGANISM: Canis familiaris

<400> SEQUENCE: 64

Gln Ser Phe Asp Thr Thr Leu Gly Ala His Val
1               5                   10

<210> SEQ ID NO 65
<211> LENGTH: 109
<212> TYPE: PRT
<213> ORGANISM: Canis familiaris

<400> SEQUENCE: 65

Gly Gln Ala His Gln Pro Ser Val Tyr Val Leu Pro Pro Ser Arg Glu
1               5                   10                  15

Glu Leu Ser Lys Asn Thr Val Ser Leu Thr Cys Leu Ile Lys Asp Phe
            20                  25                  30

Phe Pro Pro Asp Ile Asp Val Glu Trp Gln Ser Asn Gly Gln Gln Glu
        35                  40                  45

Pro Glu Ser Lys Tyr Arg Thr Thr Pro Pro Gln Leu Asp Glu Asp Gly
    50                  55                  60

Ser Tyr Phe Leu Tyr Ser Lys Leu Ser Val Asp Lys Ser Arg Trp Gln
65                  70                  75                  80

Arg Gly Asp Thr Phe Ile Cys Ala Val Met His Glu Ala Leu His His
                85                  90                  95

His Tyr Thr Gln Glu Ser Leu Ser His Ser Pro Gly Lys
            100                 105

<210> SEQ ID NO 66
<211> LENGTH: 11
<212> TYPE: PRT
<213> ORGANISM: Canis familiaris

<400> SEQUENCE: 66

His Glu Ala Leu His His His Tyr Thr Gln Glu
1               5                   10

<210> SEQ ID NO 67
<211> LENGTH: 657
<212> TYPE: DNA
<213> ORGANISM: Artificial Sequence
<220> FEATURE:
<223> OTHER INFORMATION: ZTS-00008183 Light Chain

<400> SEQUENCE: 67
gagatcgtga tgacccagag ccccgccagc ctgagcctga gccaggaaga gaaagtcacc      60
atcacatgca aggccagcca gagcgtgtcc ttcgccggca caggcctgat gcactggtat     120
cagcagaagc ccggccaggc ccccaagctg ctgatctacc gggccagcaa cctggaagcc     180
ggcgtgccaa gcagattcag cggcagcggc tccggcaccg acttcagctt caccatcagc     240
agcctcgaac ccgaggacgt ggccgtgtac tactgccagc agagcagaga gtacccctgg     300
accttcggcc agggtaccaa gctggaaatc aagcggaacg acgcccagcc cgccgtgtac     360

-continued

```
ctgttccagc ccagccccga tcagctgcac accggcagcg cttcagtcgt ctgcctgctg      420
aacagcttct accccaagga catcaacgtg aagtggaagg tggacggcgt gatccaggac      480
accggcatcc aggaaagcgt caccgagcag gacaaggaca gcacctacag cctgagcagc      540
accctgacca tgtccagcac cgagtacctg agccacgagc tgtatagctg cgagatcacc      600
cacaagagcc tgcctagcac cctgatcaag agcttccagc ggagcgagtg ctagtag        657
```

```
<210> SEQ ID NO 68
<211> LENGTH: 217
<212> TYPE: PRT
<213> ORGANISM: Artificial Sequence
<220> FEATURE:
<223> OTHER INFORMATION: ZTS-00008183 Light Chain

<400> SEQUENCE: 68

Glu Ile Val Met Thr Gln Ser Pro Ala Ser Leu Ser Leu Ser Gln Glu
1               5                   10                  15

Glu Lys Val Thr Ile Thr Cys Lys Ala Ser Gln Ser Val Ser Phe Ala
            20                  25                  30

Gly Thr Gly Leu Met His Trp Tyr Gln Gln Lys Pro Gly Gln Ala Pro
        35                  40                  45

Lys Leu Leu Ile Tyr Arg Ala Ser Asn Leu Glu Ala Gly Val Pro Ser
    50                  55                  60

Arg Phe Ser Gly Ser Gly Ser Gly Thr Asp Phe Ser Phe Thr Ile Ser
65                  70                  75                  80

Ser Leu Glu Pro Glu Asp Val Ala Val Tyr Tyr Cys Gln Gln Ser Arg
                85                  90                  95

Glu Tyr Pro Trp Thr Phe Gly Gln Gly Thr Lys Leu Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
            195                 200                 205

Ile Lys Ser Phe Gln Arg Ser Glu Cys
        210                 215
```

```
<210> SEQ ID NO 69
<211> LENGTH: 1365
<212> TYPE: DNA
<213> ORGANISM: Artificial Sequence
<220> FEATURE:
<223> OTHER INFORMATION: ZTS-00008183 Heavy Chain

<400> SEQUENCE: 69
gaggtgcagc tggtggaatc tggcggcgac ctggtcaagc ctggcggcag cctgagactg       60
agctgtgtgg ccagcggctt caccttcagc aactacggca tgagctgggt ccgacaggcc      120
cctggcaagg gactgcagtg ggtggccacc atcagctacg cggcagcta cacctactac      180 cccgacaaca tcaagggccg gttcaccatc agccgggaca acgccaagaa cacctgtac      240
```

-continued

```
ctgcagatga acagcctgcg ggccgaggac accgccatgt actactgcgt gcggggctac        300
ggctacgaca caatggacta ctggggccag ggcaccctcg tgaccgtctc gagcgcctca        360
acaactgctc ctagcgtgtt tcccctggcc cctagctgcg gaagtacctc aggcagcaca        420
gtggccctgg cttgtctggt gtctggatat ttccctgagc cagtgaccgt gagttggaac        480
agcggctctc tgacctccgg ggtgcacaca tttccatctg tgctgcagtc tagtggcctg        540
tactccctgt caagcatggt gactgtgcct tcctctaggt ggccatcaga aactttcacc        600
tgcaacgtgg cccatcccgc cagcaagacc aaagtggaca gcccgtgcc taaaagggag         660 aatggaaggg tgccaagacc acctgattgc cctaagtgtc cagctccaga atgctgggga        720
ggaccaagcg tgttcatctt tccacccaag cccaaagaca cactgctgat tgctagaact        780
cccgaggtga cctgcgtggt ggtggacctg gatccagagg accccgaagt gcagatctcc        840
tggttcgtgg atgggaagca gatgcagaca gccaaaactc agcctcggga ggaacagttt        900
aacggaacct atagagtggt gtctgtgctg ccaattggac accaggactg gctgaagggc        960
aaacagttta catgcaaggt gaacaacaag gccctgccta gtccaatcga gaggactatt       1020
tcaaaagcta ggggacaggc tcatcagcct tccgtgtatg tgctgcctcc atcccgggag       1080
gaactgtcta gaacacagt gagtctgact tgtctgatca agatttctt tccccctgac         1140 attgatgtgg agtggcagag caatgggcag caggagccag aatccaagta cagaaccaca       1200
ccaccccagc tggacgaaga tggctcctat ttcctgtaca gtaagctgtc agtggacaaa       1260
tctaggtggc agcgcgggga tacctttatc tgcgccgtga tgcacgaggc tctgcaccat       1320
cattacacac aagaaagtct gtcacatagc cccggcaagt agtag                       1365
```

```
<210> SEQ ID NO 70
<211> LENGTH: 453
<212> TYPE: PRT
<213> ORGANISM: Artificial Sequence
<220> FEATURE:
<223> OTHER INFORMATION: ZTS-00008183 Heavy Chain

<400> SEQUENCE: 70

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asn Tyr
            20                  25                  30

Gly Met Ser Trp Val Arg Gln Ala Pro Gly Lys Gly Leu Gln Trp Val
        35                  40                  45

Ala Thr Ile Ser Tyr Gly Gly Ser Tyr Thr Tyr Tyr Pro Asp Asn Ile
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Val Arg Gly Tyr Gly Tyr Asp Thr Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160
```

-continued

```
Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
            245                 250                 255

Ile Ala Arg Thr Pro Glu Val Thr Cys Val Val Val Asp Leu Asp Pro
        260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
            325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
            405                 410                 415

Ser Val Asp Lys Ser Arg Trp Gln Arg Gly Asp Thr Phe Ile Cys Ala
            420                 425                 430

Val Met His Glu Ala Leu His His His Tyr Thr Gln Glu Ser Leu Ser
            435                 440                 445

His Ser Pro Gly Lys
        450

<210> SEQ ID NO 71
<211> LENGTH: 5
<212> TYPE: PRT
<213> ORGANISM: Mus musculus

<400> SEQUENCE: 71

Ser Ser Trp Met Asn
1               5

<210> SEQ ID NO 72
<211> LENGTH: 17
<212> TYPE: PRT
<213> ORGANISM: Mus musculus

<400> SEQUENCE: 72

Gln Ile Tyr Pro Gly Asp Gly Asp Thr Asn Tyr Asn Gly Lys Phe Lys
1               5                   10                  15
```

-continued

```
Gly

<210> SEQ ID NO 73
<211> LENGTH: 10
<212> TYPE: PRT
<213> ORGANISM: Mus musculus

<400> SEQUENCE: 73

Ala Arg His Tyr Asp Gly Ser Thr Asp Tyr
1               5               10

<210> SEQ ID NO 74
<211> LENGTH: 11
<212> TYPE: PRT
<213> ORGANISM: Mus musculus

<400> SEQUENCE: 74

Arg Ala Ser Glu Asn Ile Tyr Ser Asn Leu Ala
1               5               10

<210> SEQ ID NO 75
<211> LENGTH: 7
<212> TYPE: PRT
<213> ORGANISM: Mus musculus

<400> SEQUENCE: 75

Ala Ala Thr Asn Leu Ala Asp
1               5

<210> SEQ ID NO 76
<211> LENGTH: 9
<212> TYPE: PRT
<213> ORGANISM: Mus musculus

<400> SEQUENCE: 76

Gln His Phe Trp Gly Thr Pro Tyr Thr
1               5

<210> SEQ ID NO 77
<211> LENGTH: 117
<212> TYPE: PRT
<213> ORGANISM: Artificial Sequence
<220> FEATURE:
<223> OTHER INFORMATION: Caninized Sequence - Variable Heavy Region
      Engineered to Have Sequences from Mus musculus and Canis

<400> SEQUENCE: 77

Glu Val Gln Leu Val Gln Ser Gly Ala Glu Val Lys Lys Pro Gly Ala
1               5               10              15

Ser Val Lys Val Ser Cys Lys Thr Ser Gly Tyr Thr Phe Ile Ser Ser
            20              25              30

Trp Met Asn Trp Val Arg Gln Ala Pro Gly Ala Gly Leu Asp Trp Met
        35              40              45

Gly Gln Ile Tyr Pro Gly Asp Gly Asp Thr Asn Tyr Asn Gly Lys Phe
    50              55              60

Lys Gly Arg Val Thr Leu Thr Ala Asp Thr Ser Thr Ser Thr Ala Tyr
65              70              75              80

Met Glu Leu Ser Ser Leu Arg Ala Gly Asp Ile Ala Val Tyr Tyr Cys
            85              90              95

Ala Arg His Tyr Asp Gly Ser Thr Asp Tyr Trp Gly Gln Gly Thr Leu
            100             105             110

Val Thr Val Ser Ser
```

-continued

115

```
<210> SEQ ID NO 78
<211> LENGTH: 351
<212> TYPE: DNA
<213> ORGANISM: Artificial Sequence
<220> FEATURE:
<223> OTHER INFORMATION: Caninized Sequence - Variable Heavy Region
      Engineered to Have Sequences from Mus musculus and Canis

<400> SEQUENCE: 78
gaggtgcagc tggtgcagtc cggagctgag gtgaagaagc caggagcttc cgtgaaggtg      60
agctgcaaga catctggcta caccttcatc tccagctgga tgaactgggt gagacaggct     120
ccaggagctg gcctggactg gatgggccag atctaccctg gcgacggcga tacaaactat     180
aatggcaagt taagggaag ggtgaccctg acagctgaca ccagcacatc taccgcttac     240
atggagctgt cttccctgag ggccggcgat atcgccgtgt actattgtgc ccggcactat     300
gacggctcca ccgattactg gggccagggc acactggtga ccgtctcgag c             351

<210> SEQ ID NO 79
<211> LENGTH: 103
<212> TYPE: PRT
<213> ORGANISM: Artificial Sequence
<220> FEATURE:
<223> OTHER INFORMATION: Caninized Sequence - Variable Light Region
      Engineered to Have Sequences from Mus musculus and Canis

<400> SEQUENCE: 79

Glu Ile Val Met Thr Gln Ser Pro Ala Ser Leu Ser Leu Ser Gln Gly
1               5                   10                  15

Glu Lys Val Thr Ile Thr Cys Arg Ala Ser Glu Asn Ile Tyr Ser Asn
            20                  25                  30

Leu Ala Trp Tyr Gln Gln Arg Pro Gly Gln Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Ser Leu Thr Ile Ser Ser Leu Glu Pro
65                  70                  75                  80

Glu Asp Val Ala Val Tyr Tyr Cys Gln His Phe Trp Gly Thr Pro Tyr
                85                  90                  95

Thr Phe Gly Gln Gly Thr Lys
            100

<210> SEQ ID NO 80
<211> LENGTH: 306
<212> TYPE: DNA
<213> ORGANISM: Artificial Sequence
<220> FEATURE:
<223> OTHER INFORMATION: Caninized Sequence - Variable Light Region
      Engineered to Have Sequences from Mus musculus and Canis

<400> SEQUENCE: 80
gagatcgtga tgacccagtc ccctgcttct ctgtccctga gccagggcga aaaggtgacc      60
atcacatgca gggcctctga aaacatctac tccaatctgg cttggtatca gcagcggccc     120
ggacaggctc ctaagctgct gatctacgcc gctacaaacc tggctgacgg cgtgccaagc     180
aggttctctg atccggaag cggcaccgac ttttctctga caatctccag cctggagcca     240
gaggatgtgg ccgtgtacta ttgtcagcac ttctggggca cccctatac atttggccag     300 ggtacc                                                                306
```

-continued

```
<210> SEQ ID NO 81
<211> LENGTH: 7
<212> TYPE: PRT
<213> ORGANISM: Homo sapiens

<400> SEQUENCE: 81

Phe Ser Ser Tyr Gly Met His
1               5

<210> SEQ ID NO 82
<211> LENGTH: 11
<212> TYPE: PRT
<213> ORGANISM: Homo sapiens

<400> SEQUENCE: 82

Val Ile Ser Tyr Asp Gly Ser Ile Lys Tyr Tyr
1               5                   10

<210> SEQ ID NO 83
<211> LENGTH: 14
<212> TYPE: PRT
<213> ORGANISM: Homo sapiens

<400> SEQUENCE: 83

Thr Gly Glu Tyr Ser Gly Tyr Asp Thr Asp Pro Gln Tyr Ser
1               5                   10

<210> SEQ ID NO 84
<211> LENGTH: 11
<212> TYPE: PRT
<213> ORGANISM: Homo sapiens

<400> SEQUENCE: 84

Arg Ala Ser Gln Gly Ile Gly Asp Asp Leu Gly
1               5                   10

<210> SEQ ID NO 85
<211> LENGTH: 7
<212> TYPE: PRT
<213> ORGANISM: Homo sapiens

<400> SEQUENCE: 85

Gly Thr Ser Thr Leu Gln Ser
1               5

<210> SEQ ID NO 86
<211> LENGTH: 9
<212> TYPE: PRT
<213> ORGANISM: Homo sapiens

<400> SEQUENCE: 86

Leu Gln Asp Ser Asn Tyr Pro Leu Thr
1               5

<210> SEQ ID NO 87
<211> LENGTH: 123
<212> TYPE: PRT
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 87

Glu Val Gln Leu Val Glu Ser Gly Gly Asp Leu Val Lys Pro Gly Gly
```

-continued

```
1                 5                 10                15

Ser Leu Arg Leu Ser Cys Val Ala Ser Gly Phe Thr Phe Ser Ser Tyr
            20                25                30

Gly Met His Trp Val Arg Gln Ala Pro Gly Lys Gly Leu Gln Trp Val
            35                40                45

Ala Val Ile Ser Tyr Asp Gly Ser Ile Lys Tyr Tyr Ala Asp Ala Val
       50                55                60

Lys Gly Arg Phe Thr Ile Ser Arg Asp Asn Ala Lys Asn Thr Leu Tyr
65                70                75                80

Leu Gln Met Asn Ser Leu Arg Ala Glu Asp Thr Ala Val Tyr Tyr Cys
                 85                90                95

Ala Arg Thr Gly Glu Tyr Ser Gly Tyr Asp Thr Asp Pro Gln Tyr Ser
                100               105               110

Trp Gly Gln Gly Thr Thr Val Thr Val Ser Ser
            115               120
```

<210> SEQ ID NO 88
<211> LENGTH: 369
<212> TYPE: DNA
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 88

```
gaagtgcagc tggtggaatc tggcggcgac ctcgtgaagc ctggcggctc tctgagactg        60
tcctgtgtgg cctccggctt caccttctcc agctacggca tgcactgggt gcgacaggcc       120
cctggaaaag gcctgcagtg ggtggccgtg atctcctacg acggctccat caagtactac       180
gccgacgccg tgaagggccg gttcaccatc agcagagaca cgccaagaa caccctgtac        240 ctgcagatga actccctgcg ggccgaggac accgccgtgt actactgtgc tagaaccggc       300
gagtactccg gctacgatac cgacccccag tactcttggg gccagggcac cacagtgacc       360
gtctcgagc                                                               369
```

<210> SEQ ID NO 89
<211> LENGTH: 103
<212> TYPE: PRT
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 89

```
Glu Ile Val Met Thr Gln Ser Pro Ala Ser Leu Ser Leu Ser Gln Glu
1                 5                 10                15

Glu Lys Val Thr Ile Thr Cys Arg Ala Ser Gln Gly Ile Gly Asp Asp
            20                25                30

Leu Gly Trp Tyr Gln Gln Lys Pro Gly Gln Ala Pro Lys Leu Leu Ile
            35                40                45

Tyr Gly Thr Ser Thr Leu Gln Ser Gly Val Pro Ser Arg Phe Ser Gly
       50                55                60

Ser Gly Ser Gly Thr Asp Phe Ser Phe Thr Ile Ser Ser Leu Glu Pro
65                70                75                80

Glu Asp Val Ala Val Tyr Tyr Cys Leu Gln Asp Ser Asn Tyr Pro Leu
                 85                90                95

Thr Phe Gly Ala Gly Thr Lys
                100
```

```
<210> SEQ ID NO 90
<211> LENGTH: 309
<212> TYPE: DNA
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 90
gaaattgtga tgacccagag cccggcgagc ctgagcctga gccaggaaga aaaagtgacc        60
attacctgcc gcgcgagcca gggcattggc gatgatctgg gctggtatca gcagaaaccg       120
ggccaggcgc cgaaactgct gatttatggc accagcaccc tgcagagcgg cgtgccgagc       180
cgctttagcg gcagcggcag cggcaccgat tttagcttta ccattagcag cctggaaccg       240
gaagatgtgg cggtgtatta ttgcctgcag gatagcaact atccgctgac ctttggcgcg       300
ggcaccaaa                                                               309

<210> SEQ ID NO 91
<211> LENGTH: 7
<212> TYPE: PRT
<213> ORGANISM: Mus musculus

<400> SEQUENCE: 91

Gly Tyr Ile Phe Ile Thr Tyr
1               5

<210> SEQ ID NO 92
<211> LENGTH: 6
<212> TYPE: PRT
<213> ORGANISM: Mus musculus

<400> SEQUENCE: 92

Phe Pro Ala Ser Gly Ser
1               5

<210> SEQ ID NO 93
<211> LENGTH: 12
<212> TYPE: PRT
<213> ORGANISM: Mus musculus

<400> SEQUENCE: 93

Gly Asp Gly Asn Tyr Ala Leu Asp Ala Met Asp Tyr
1               5                   10

<210> SEQ ID NO 94
<211> LENGTH: 15
<212> TYPE: PRT
<213> ORGANISM: Mus musculus

<400> SEQUENCE: 94

Arg Ala Ser Glu Ser Val Asp Ser Tyr Gly Asn Ser Phe Met His
1               5                   10                  15

<210> SEQ ID NO 95
<211> LENGTH: 7
<212> TYPE: PRT
<213> ORGANISM: Mus musculus

<400> SEQUENCE: 95

Leu Ala Ser Asn Leu Glu Ser
1               5
```

<210> SEQ ID NO 96
<211> LENGTH: 9
<212> TYPE: PRT
<213> ORGANISM: Mus musculus

<400> SEQUENCE: 96

Gln Gln Asn Asn Glu Asp Pro Leu Thr
1               5

<210> SEQ ID NO 97
<211> LENGTH: 118
<212> TYPE: PRT
<213> ORGANISM: Artificial Sequence
<220> FEATURE:
<223> OTHER INFORMATION: Caninized Sequence - Variable Heavy Region
      Engineered to Have Sequences from Mus musculus and Canis

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Thr Tyr
            20                  25                  30

Trp Met Asn Trp Val Arg Gln Ala Pro Gly Ala Gly Leu Asp Trp Met
        35                  40                  45

Gly Gln Ile Phe Pro Ala Ser Gly Ser Thr Asn Tyr Asn Glu Met Phe
    50                  55                  60

Glu Gly Arg Val Thr Leu Thr Ala Asp Thr Ser Thr Ser Thr Ala Tyr
65                  70                  75                  80

Met Glu Leu Ser Ser Leu Arg Ala Gly Asp Ile Ala Val Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Leu Val Thr
        115

<210> SEQ ID NO 98
<211> LENGTH: 354
<212> TYPE: DNA
<213> ORGANISM: Artificial Sequence
<220> FEATURE:
<223> OTHER INFORMATION: Caninized Sequence - Variable Heavy Region
      Engineered to Have Sequences from Mus musculus and Canis

<400> SEQUENCE: 98
gaggtgcagt tggttcagtc cggcgccgag gtgaagaagc ccggggcctc tgtaaaggtc      60
agctgcaaga ctagcggata tacatttatc acatactgga tgaactgggt ccgacaagcc     120
cctggtgccg gcctggattg gatgggccag atcttcccag caagcggatc taccaattac     180
aatgagatgt tcgagggtag ggtgaccctc acagctgata ccagtacttc aactgcatac     240
atggaactga gttccctgag agcaggcgac atcgcagttt actattgtgc ccgaggcgac     300
ggcaattatg cactggatgc tatggactac tggggtcagg gaaccctggt gaca           354

<210> SEQ ID NO 99
<211> LENGTH: 104
<212> TYPE: PRT
<213> ORGANISM: Artificial Sequence
<220> FEATURE:
<223> OTHER INFORMATION: Caninized Sequence - Variable Light Region
      Engineered to Have Sequences from Mus musculus and Canis

<400> SEQUENCE: 99

-continued

```
Asp Ile Val Met Thr Gln Thr Pro Pro Ser Leu Ser Val Ser Pro Arg
1               5                   10                  15

Glu Thr Ala Ser Ile Ser Cys Arg Ala Ser Glu Ser Val Asp Ser Tyr
            20                  25                  30

Gly Asn Ser Phe Met His Trp Tyr Leu Gln Lys Pro Gly Gln Ser Pro
        35                  40                  45

Gln Leu Leu Ile Tyr Leu Ala Ser Asn Leu Glu Ser Gly Val Ser Asp
    50                  55                  60

Arg Phe Ser Gly Ser Gly Ser Gly Thr Asp Phe Thr Leu Arg Ile Ser
65                  70                  75                  80

Arg Val Glu Ala Asn Asp Thr Gly Val Tyr Tyr Cys Gln Gln Asn Asn
                85                  90                  95

Glu Asp Pro Leu Thr Phe Gly Gln
            100
```

```
<210> SEQ ID NO 100
<211> LENGTH: 312
<212> TYPE: DNA
<213> ORGANISM: Artificial Sequence
<220> FEATURE:
<223> OTHER INFORMATION: Caninized Sequence - Variable Light Region
      Engineered to Have Sequences from Mus musculus and Canis

<400> SEQUENCE: 100
gatattgtga tgacacagac tccaccctcc ctttctgtca gccctcggga gaccgcctcc        60
attagctgtc gcgccagtga gtccgtcgat tcctacggaa atagcttcat gcactggtat       120
ctgcagaaac caggtcagtc tcctcaattg ctgatctacc tggcttctaa cctggaaagc       180
ggtgtgtcag ataggttttc cggaagtggt agcggaactg actttaccct gcgtatttcc       240
cgagtggaag ccaatgacac tggtgtttac tactgtcagc agaataacga agaccccctg       300
acctttggcc ag                                                          312
```

```
<210> SEQ ID NO 101
<211> LENGTH: 5
<212> TYPE: PRT
<213> ORGANISM: Homo sapiens

<400> SEQUENCE: 101

Ser Asn Val Ile Ser
1               5
```

```
<210> SEQ ID NO 102
<211> LENGTH: 17
<212> TYPE: PRT
<213> ORGANISM: Homo sapiens

<400> SEQUENCE: 102

Gly Val Ile Pro Ile Val Asp Ile Ala Asn Tyr Ala Gln Arg Phe Lys
1               5                   10                  15

Gly
```

```
<210> SEQ ID NO 103
<211> LENGTH: 13
<212> TYPE: PRT
<213> ORGANISM: Homo sapiens

<400> SEQUENCE: 103

Ala Ser Thr Leu Gly Leu Val Leu Asp Ala Met Asp Tyr
1               5                   10
```

```
<210> SEQ ID NO 104
<211> LENGTH: 12
<212> TYPE: PRT
<213> ORGANISM: Homo sapiens

<400> SEQUENCE: 104

Arg Ala Ser Gln Ser Leu Gly Ser Ser Tyr Leu Ala
1               5               10

<210> SEQ ID NO 105
<211> LENGTH: 7
<212> TYPE: PRT
<213> ORGANISM: Homo sapiens

<400> SEQUENCE: 105

Gly Ala Ser Ser Arg Ala Pro
1               5

<210> SEQ ID NO 106
<211> LENGTH: 9
<212> TYPE: PRT
<213> ORGANISM: Homo sapiens

<400> SEQUENCE: 106

Gln Gln Tyr Ala Asp Ser Pro Ile Thr
1               5

<210> SEQ ID NO 107
<211> LENGTH: 120
<212> TYPE: PRT
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 107

Glu Val Gln Leu Val Gln Ser Ala Ala Glu Val Lys Lys Pro Gly Ala
1               5               10              15

Ser Val Lys Val Ser Cys Lys Thr Ser Gly Tyr Ile Phe Ile Ser Asn
            20              25              30

Val Ile Ser Trp Val Gln Gln Ala Pro Gly Ala Gly Leu Glu Trp Met
        35              40              45

Gly Gly Val Ile Pro Ile Val Asp Ile Ala Asn Tyr Ala Gln Arg Phe
    50              55              60

Lys Gly Arg Val Thr Leu Thr Ala Asp Thr Ser Thr Asn Thr Val Tyr
65              70              75              80

Met Glu Leu Ser Asn Leu Arg Thr Glu Asp Thr Ala Val Tyr Tyr Cys
            85              90              95

Ala Ser Thr Leu Gly Leu Val Leu Asp Ala Met Asp Tyr Trp Gly Gln
            100             105             110

Gly Thr Leu Val Thr Val Ser Ser
        115                 120

<210> SEQ ID NO 108
<211> LENGTH: 359
<212> TYPE: DNA
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 108
```

-continued

```
gaggtgcagc tggtgcagag cgccgctgag gtgaagaagc caggcgcctc cgtgaaggtg        60
agctgcaaga catctggcta catcttcatc tccaacgtga tcagctgggt gcagcaggct       120
ccaggagctg gactggagtg gatgggcggc gtgatcccta tcgtggacat cgccaattac       180
gctcagaggt ttaagggccg ggtgaccctg acagccgata cctctacaaa caccgtgtat       240
atggagctgt ccaatctgag gacagaggac accgccgtgt actattgtgc ttctaccctg       300
ggcctggtgc tggacgctat ggattattgg ggccagggca cactggtgac cgtctcgag        359
```

```
<210> SEQ ID NO 109
<211> LENGTH: 108
<212> TYPE: PRT
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 109

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Lys Leu Glu Ile Lys
            100                 105
```

```
<210> SEQ ID NO 110
<211> LENGTH: 309
<212> TYPE: DNA
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 110
gagaccgtgc tgacacagag ccctggcacc ctgtccctga gcccaggaga gagggccaca        60
ctgtcttgcc gggcttctca gtccctgggc tccagctacc tggcctggta tcagcagaag       120
ccaggccagg ctcccaggct gctgatctac ggagcctctt ccagagctcc aggcgtgcct       180
gctcgcttca gcggatctgg ctccggcacc gactttaccc tgacaatcag ctctctggag       240
cccgaggact cgccgtgta ctattgtcag cagtatgctg attcccctat cacatttggc       300
cagggtacc                                                               309
```

```
<210> SEQ ID NO 111
<211> LENGTH: 8
<212> TYPE: PRT
<213> ORGANISM: Homo sapiens

<400> SEQUENCE: 111

Gly Tyr Thr Phe Ser Ser Asn Val
1               5
```

```
<210> SEQ ID NO 112
<211> LENGTH: 8
<212> TYPE: PRT
<213> ORGANISM: Homo sapiens

<400> SEQUENCE: 112

Val Ile Pro Ile Val Asp Ile Ala
1               5

<210> SEQ ID NO 113
<211> LENGTH: 10
<212> TYPE: PRT
<213> ORGANISM: Homo sapiens

<400> SEQUENCE: 113

Leu Gly Leu Val Leu Asp Ala Met Asp Tyr
1               5                   10

<210> SEQ ID NO 114
<211> LENGTH: 12
<212> TYPE: PRT
<213> ORGANISM: Homo sapiens

<400> SEQUENCE: 114

Arg Ala Ser Gln Ser Leu Gly Ser Ser Tyr Leu Ala
1               5                   10

<210> SEQ ID NO 115
<211> LENGTH: 7
<212> TYPE: PRT
<213> ORGANISM: Homo sapiens

<400> SEQUENCE: 115

Gly Ala Ser Ser Arg Ala Pro
1               5

<210> SEQ ID NO 116
<211> LENGTH: 9
<212> TYPE: PRT
<213> ORGANISM: Homo sapiens

<400> SEQUENCE: 116

Gln Gln Tyr Ala Asp Ser Pro Ile Thr
1               5

<210> SEQ ID NO 117
<211> LENGTH: 120
<212> TYPE: PRT
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 117

Glu Val Gln Leu Val Glu Ser Gly Gly Asp Leu Val Lys Pro Ala Gly
1               5                   10                  15

Ser Leu Arg Leu Ser Cys Val Ala Ser Gly Tyr Thr Phe Ser Ser Asn
            20                  25                  30

Val Met Ser Trp Val Arg Gln Ala Pro Gly Lys Gly Leu Gln Trp Val
            35                  40                  45

Gly Tyr Val Ile Pro Ile Val Asp Ile Ala Asn Tyr Ala Asp Ala Val
        50                  55                  60

Lys Gly Arg Phe Thr Ile Ser Arg Asp Asn Ala Lys Asn Thr Leu Tyr
```

-continued

```
65              70              75              80

Leu Gln Met Asn Ser Leu Arg Val Glu Asp Thr Ala Val Tyr Tyr Cys
                85                  90                  95

Thr Arg Thr Leu Gly Leu Val Leu Asp Ala Met Asp Tyr Trp Gly Gln
            100                 105                 110

Gly Thr Leu Val Thr Val Ser Ser
        115                 120
```

<210> SEQ ID NO 118
<211> LENGTH: 359
<212> TYPE: DNA
<213> ORGANISM: Artificial Sequence
<220> FEATURE:
<223> OTHER INFORMATION: Caninized Sequence - Variable Heavy Region
      Engineered to Have Sequences from Homo sapiens and Canis

<400> SEQUENCE: 118

```
gaggtgcagc tggtggagag cggaggcgac ctggtgaagc cagctggctc tctgaggctg      60
tcctgcgtgg ctagcggcta caccttctcc agcaacgtga tgtcttgggt gagacaggct     120
ccaggcaagg gactgcagtg ggtgggctac gtgatcccta tcgtggacat cgccaactat     180
gccgatgctg tgaagggcag gtttaccatc tctcgggaca cgctaagaa tacactgtac     240 ctgcagatga actccctgag agtggaggat acagccgtgt actattgtac ccgcacactg     300
ggcctggtgc tggacgctat ggattattgg ggccagggca ccctggtgac agtctcgag     359
```

<210> SEQ ID NO 119
<211> LENGTH: 108
<212> TYPE: PRT
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 119

```
Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Lys Leu Glu Ile Lys
            100                 105
```

<210> SEQ ID NO 120
<211> LENGTH: 309
<212> TYPE: DNA
<213> ORGANISM: Artificial Sequence
<220> FEATURE:
<223> OTHER INFORMATION: Caninized Sequence - Variable Light Region
      Engineered to Have Sequences from Homo sapiens and Canis

<400> SEQUENCE: 120

```
gagaccgtgc tgacacagag ccctggcacc ctgtccctga gcccaggaga gagggccaca      60
```

-continued

| | | | | | |
|---|---|---|---|---|---|
| ctgtcttgcc | gggcttctca | gtccctgggc | tccagctacc | tggcctggta | tcagcagaag | 120 |
| ccaggccagg | ctcccaggct | gctgatctac | ggagcctctt | ccagagctcc | aggcgtgcct | 180 |
| gctcgcttca | gcggatctgg | ctccggcacc | gactttaccc | tgacaatcag | ctctctggag | 240 |
| cccgaggact | tcgccgtgta | ctattgtcag | cagtatgctg | attcccctat | cacatttggc | 300 |
| cagggtacc | | | | | 309 |

CANINE ANTIBODY VARIANTS

CROSS-REFERENCE TO RELATED APPLICATIONS

This application is a national phase application of PCT international patent application PCT/US2021/052338, filed Sep. 28, 2021, which claims priority to and the benefit of U.S. Provisional Patent Application 63/084,241, filed Sep. 28, 2020, both of which are incorporated by reference herein in their entirety.

FIELD OF THE INVENTION

The invention relates generally to canine antibody variants and uses thereof. Specifically, the invention relates to a mutation in the Fc constant region of canine antibody for improving half-life.

BACKGROUND OF THE INVENTION

Canine IgG monoclonal antibodies (mAbs) are being developed as effective therapeutics in veterinary medicine. Several years ago, four canine IgG subclasses were identified and characterized (Bergeron et al., 2014, *Vet Immunol Immunopathol.*, vol. 157(1-2), pages 31-41). However, not much work has been done on extending the half-life of canine IgGs.

Through a recycling mechanism, the neonatal Fc receptor (FcRn) prolongs the half-life of an IgG in a pH-dependent interaction with its fragment crystallizable (Fc) region. Specifically, the Fc region spanning the interface of CH2 and CH3 domains interacts with the FcRn on the surface of cells to regulate IgG homeostasis. This interaction is favored by an acidic interaction after IgG pinocytosis and thus IgG is protected from degradation. The endocytosed IgG is then recycled back to the cell surface and released into the blood stream at an alkaline pH thereby maintaining sufficient serum IgG for proper function. Accordingly, the pharmacokinetic profile of IgGs depend on the structural and functional properties of their Fc regions.

Three canine IgG subclasses bind canine FcRn and have been compared to human IgG analogues. Half-life of canine IgG remains to be fully studied because, without any experimental support, one cannot expect or predict whether or not they will align closely with human IgGs.

Extended half-life of IgG could allow less frequent dosing and/or lower dose of the antibody drug, which in turn reduces veterinary visits, improves patient compliance, and lowers the concentration-dependent cytotoxicity/adverse events.

Accordingly, there exists a need to identify mutations in the Fc constant regions to improve half-life.

SUMMARY OF THE INVENTION

The invention relates to mutant canine IgGs that provide higher FcRn affinity and higher half-life, relative to wild-type canine IgGs. Specifically, the inventors of the instant application have found that substituting the amino acid residue asparagine (Asn or N) at position 434 with another amino acid surprisingly and unexpectedly enhanced the affinity to FcRn, and thereby increased the half-life of IgG.

In one aspect, the invention provides a modified IgG comprising: a canine IgG constant domain comprising at least one amino acid substitution relative to a wild-type canine IgG constant domain, wherein said substitution is at amino acid residue 434, numbered according to the EU index as in Kabat. In an exemplary embodiment, said substitution is a substitution of asparagine at position 434 with histidine.

In another aspect, the invention provides a polypeptide comprising: a canine IgG constant domain comprising at least one amino acid substitution relative to a wild-type canine IgG constant domain, wherein said substitution is at amino acid residue 434, numbered according to the EU index as in Kabat.

In yet another aspect, the invention provides an antibody or a molecule comprising: a canine IgG constant domain comprising at least one amino acid substitution relative to a wild-type canine IgG constant domain, wherein said substitution is at amino acid residue 434, numbered according to the EU index as in Kabat.

In a further aspect, the invention provides a method for producing or manufacturing an antibody or a molecule, the method comprising: providing a vector or a host cell having an antibody comprising a canine IgG constant domain, said canine IgG constant domain comprising at least one amino acid substitution relative to a wild-type canine IgG constant domain, wherein said substitution is at amino acid residue 434, numbered according to the EU index as in Kabat.

In another aspect, the invention provides a method for increasing an antibody serum half-life in a dog, the method comprising: administering said dog a therapeutically effective amount of an antibody comprising a canine IgG constant domain, said canine IgG constant domain comprising at least one amino acid substitution relative to a wild-type canine IgG constant domain, wherein said substitution is at amino acid residue 434, numbered according to the EU index as in Kabat. In an exemplary embodiment, the antibody increases the half-life for about 30 days.

In another aspect, the invention provides a method for maintaining a therapeutic serum level of an antibody in a dog, the method comprising: administering said dog a therapeutically effective amount of an antibody comprising a canine IgG constant domain, said canine IgG constant domain comprising at least one amino acid substitution relative to a wild-type canine IgG constant domain, wherein said substitution is at amino acid residue 434, numbered according to the EU index as in Kabat. In an exemplary embodiment, the antibody, maintains the therapeutic serum level of said antibody in said dog over a period ranging from about 1 month to about 7 months.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 2A shows the amino acid sequences of Canine IgGB having N434H and wild-type (WT) canine IgGB.

FIG. 2B shows the alignment of the amino acid sequences of wild-type (WT) human IgG1, WT canine 1gGA, WT canine IgGB, WT canine IgGC, and WT canine IgGD. The amino acid residues are numbered according to the Eu index as in Kabat. The CH1, hinge, CH2, and CH3 amino acid residues are in red, violet, blue, and green, respectively.

FIG. 2C shows Fc nucleotide sequences of WT IgGB 65.

Figure 3:
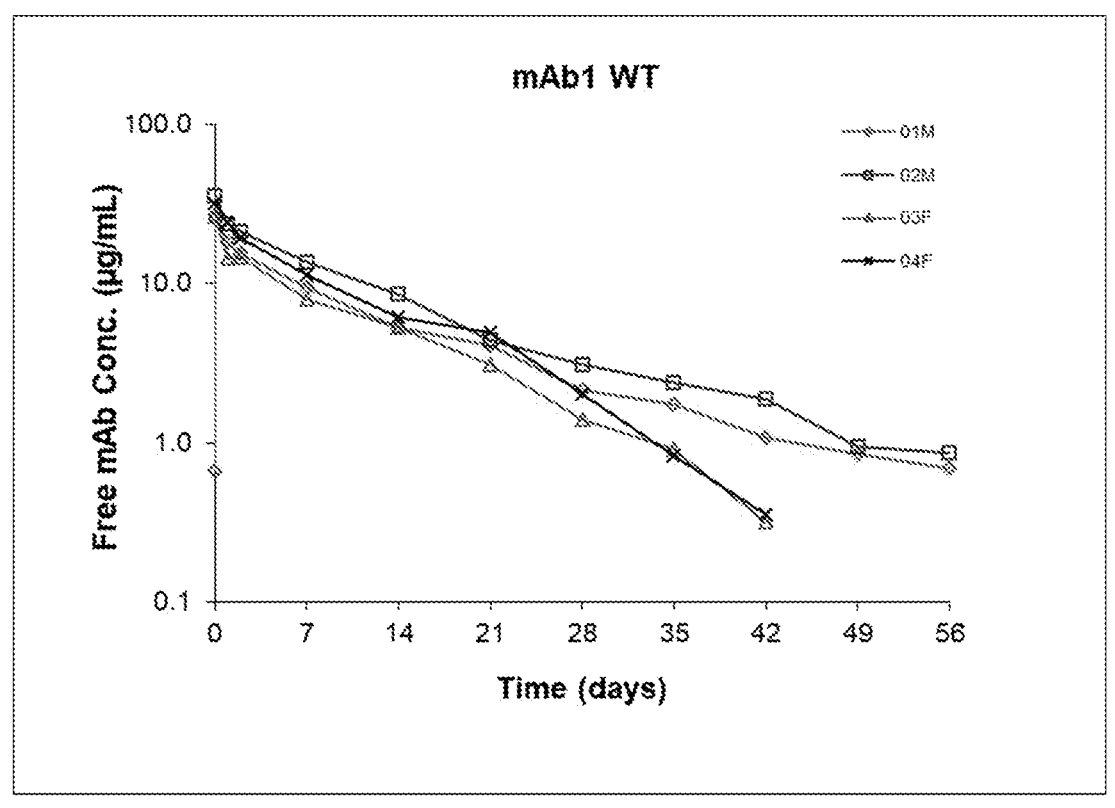

FIG. 3 shows individual serum concentrations for WT mAb1 IgG in 4 dogs, 2 male (01M, 02M) and 2 female (03F, 04F) after a single injection of 2 mg/kg measured over a 56 day period.

Figure 4:
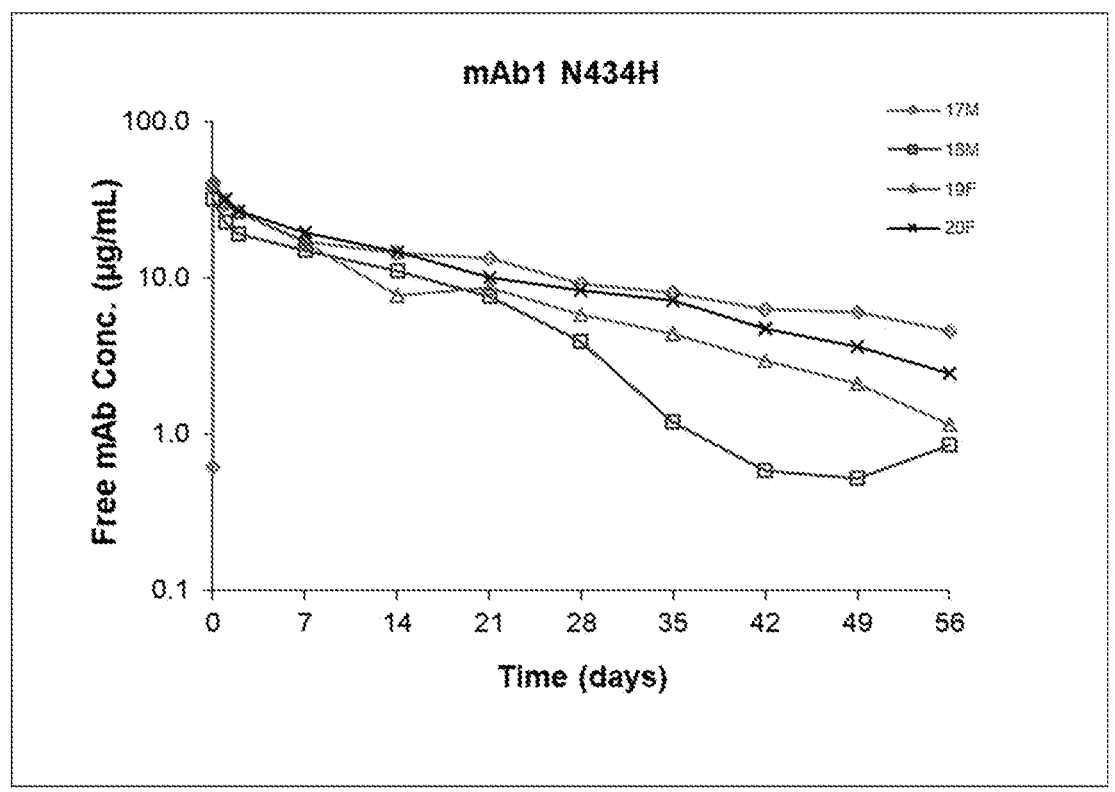

FIG. 4 shows individual serum concentrations for N434H mAb1 IgG in after a 4 dogs, 2 male (17M, 18M) and 2 female (19F, 20F) single injection of 2 mg/kg measured over a 56 day period.

Figure 5:
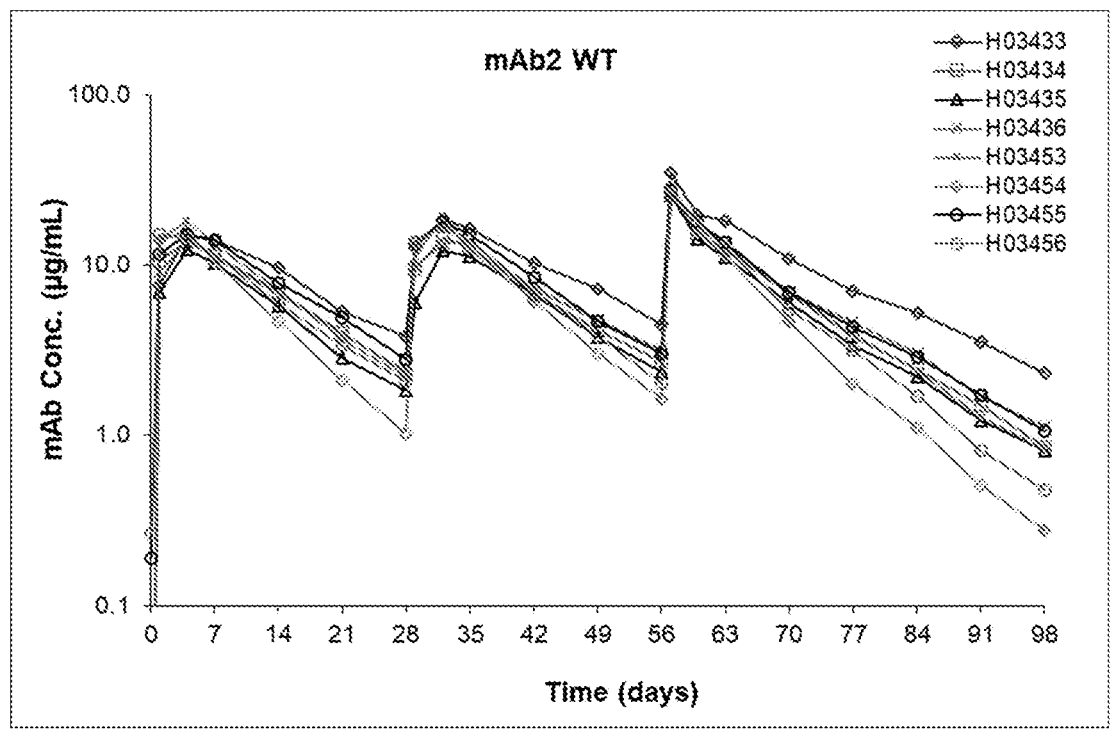

FIG. 5 shows individual serum concentrations for WT mAb2 IgG in 8 dogs, 4 male (H03433, H03434. H03435, H03436) and 4 female (H03453, H03454, H03455, H03456) after three injections of 2 mg/kg (SC/SC/IV) measured over a 98 day period.

Figure 6:
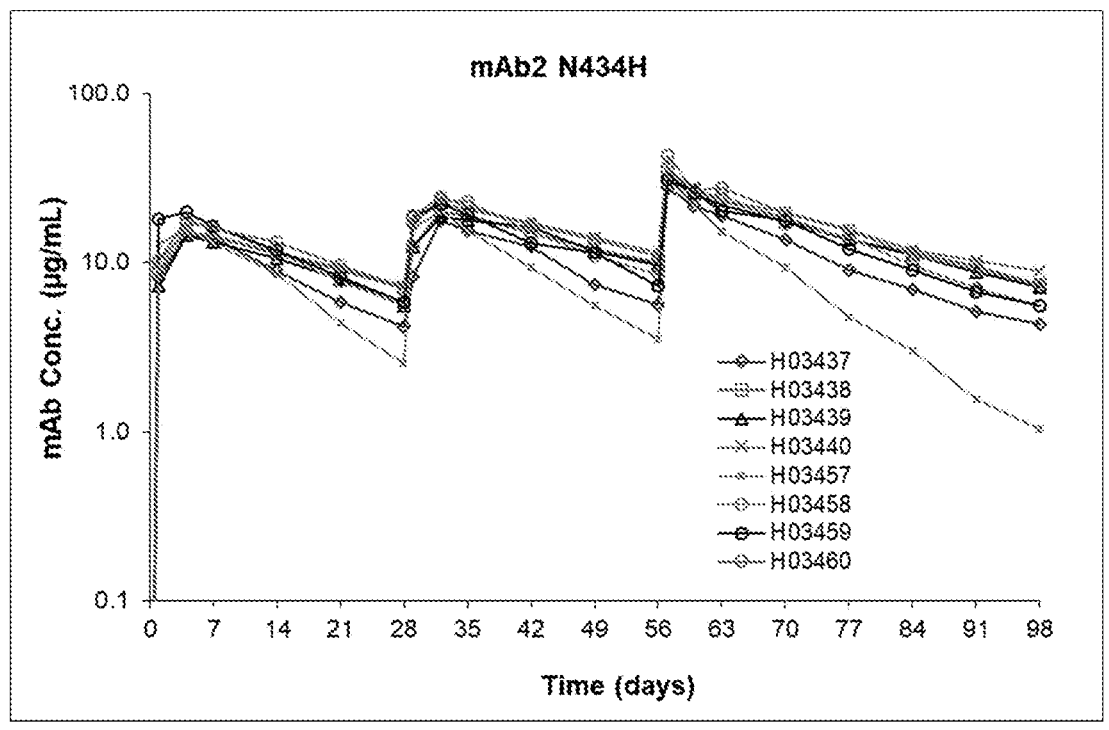

FIG. 6 shows individual serum concentrations for N434H mAb2 IgG in 8 dogs, 4 male (H03433, H03434. H03435, H03436) and 4 female (H03453, H03454, H03455, and H03456) after three injections of 2 mg/kg (SC/SC/IV) measured over a 98 day period.

Figure 7:
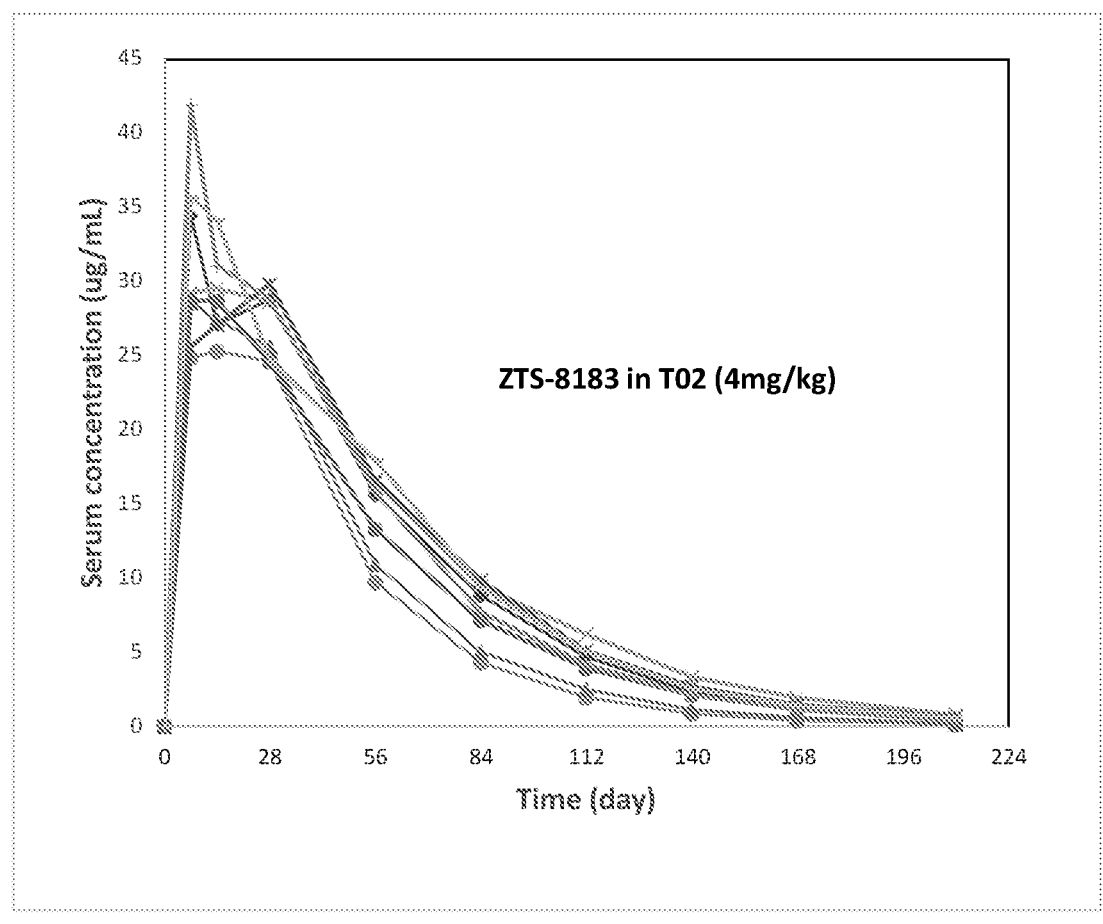

FIG. 7 shows serum profiles of ZTS-00008183 in dogs following a single 4 mg/kg subcutaneous administration. The colors represent different animal identification numbers.

Figure 8:
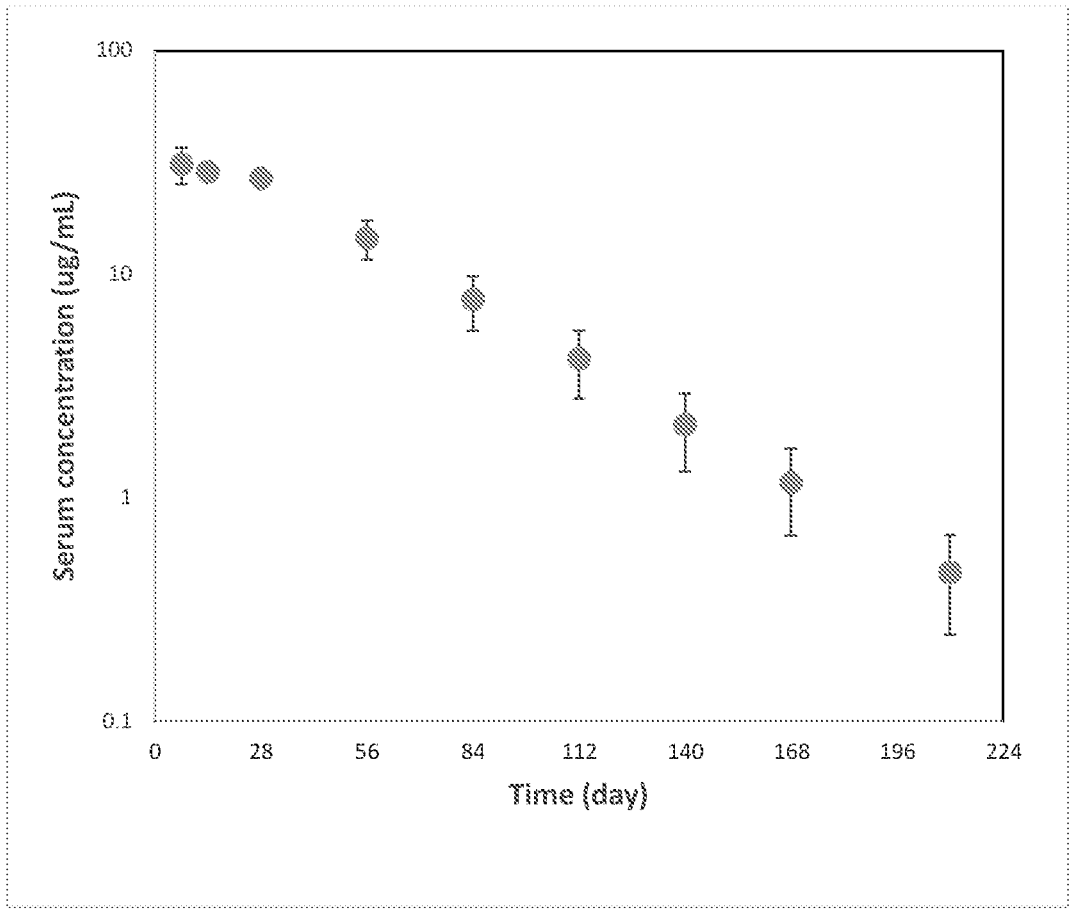

FIG. 8 shows mean serum profiles of ZTS-00008183 in dogs following a single 4 mg/kg subcutaneous administration.

Figure 9:
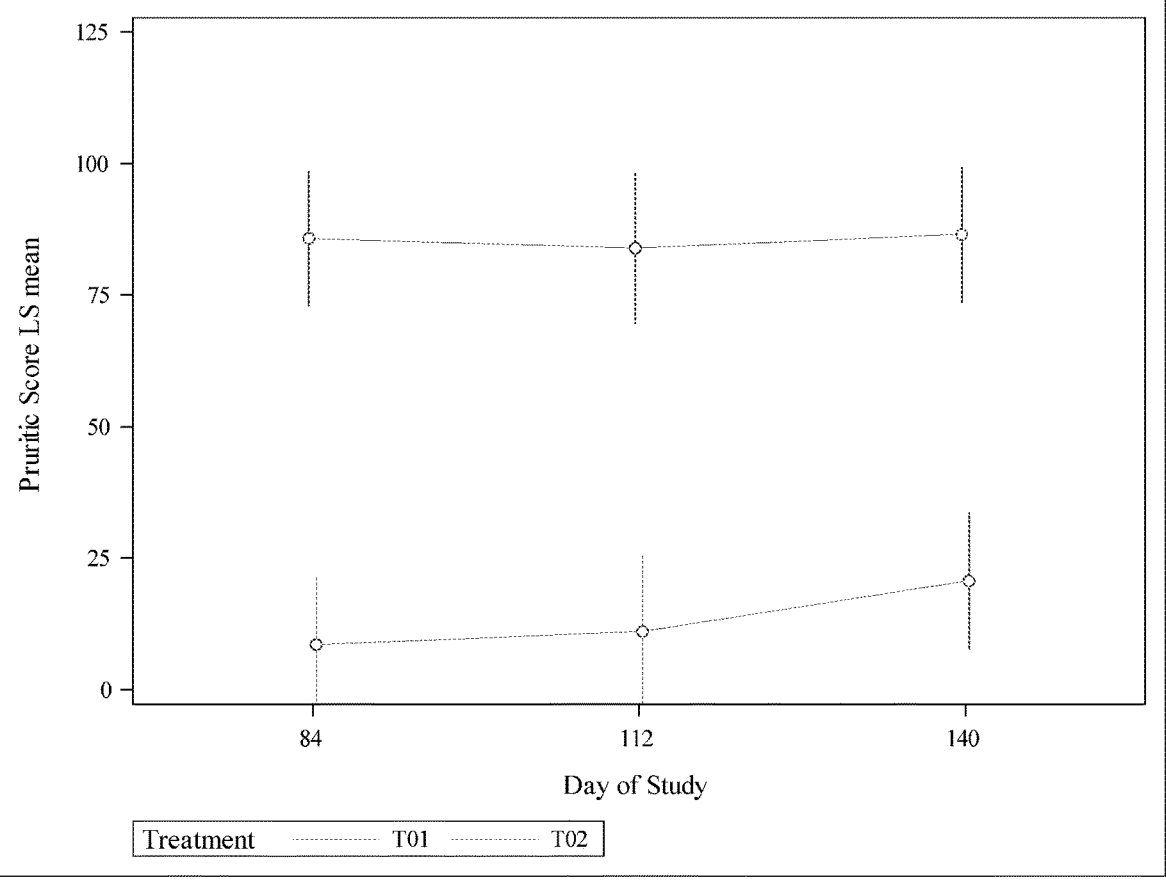

FIG. 9 shows plot of least squares means by treatment by time point (3-5 months). alpha levels: Day 84=0.07085, Day 112=0.04575, Day 140=0.04352.

Figure 10:
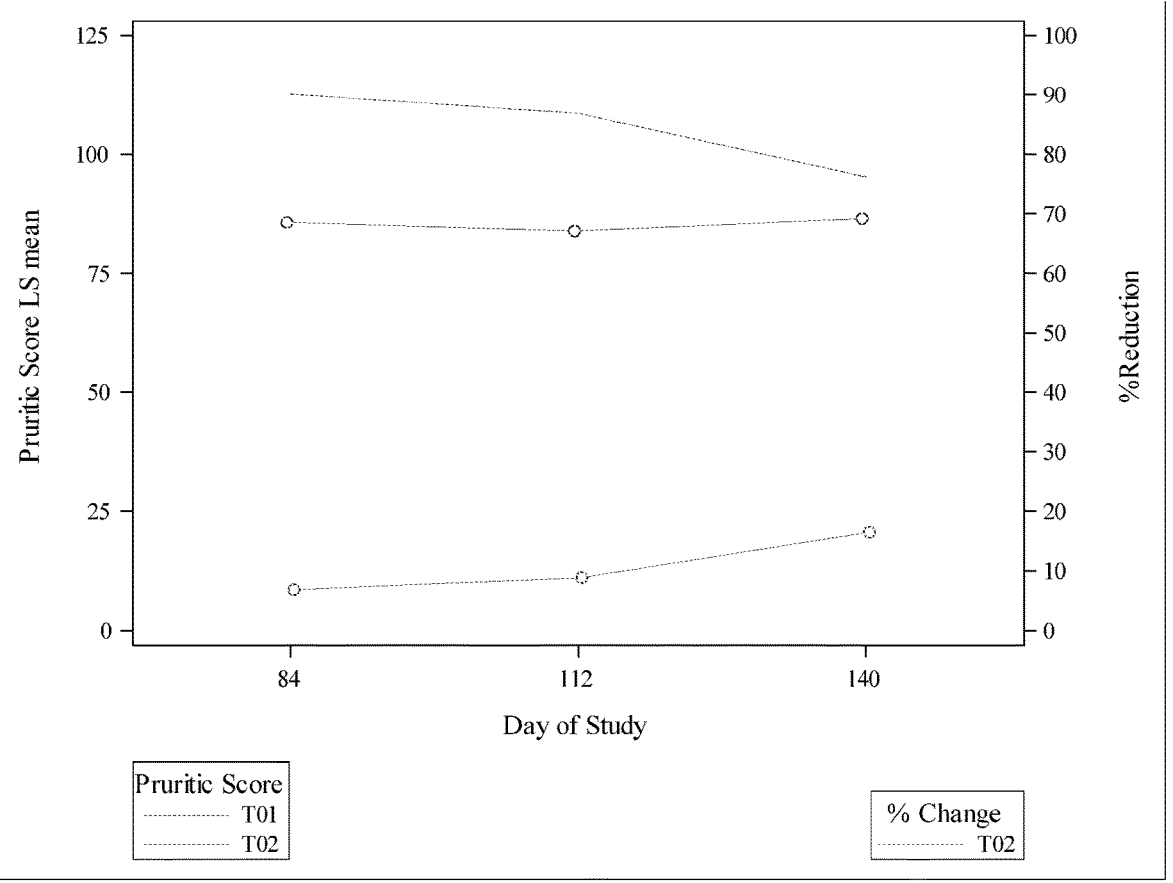

FIG. 10 shows plot of least squares means and percent change by treatment by time point (3-5 months). % change in means=100×[mean(T01)−mean(T02)/mean(T01)].

Figure 11:
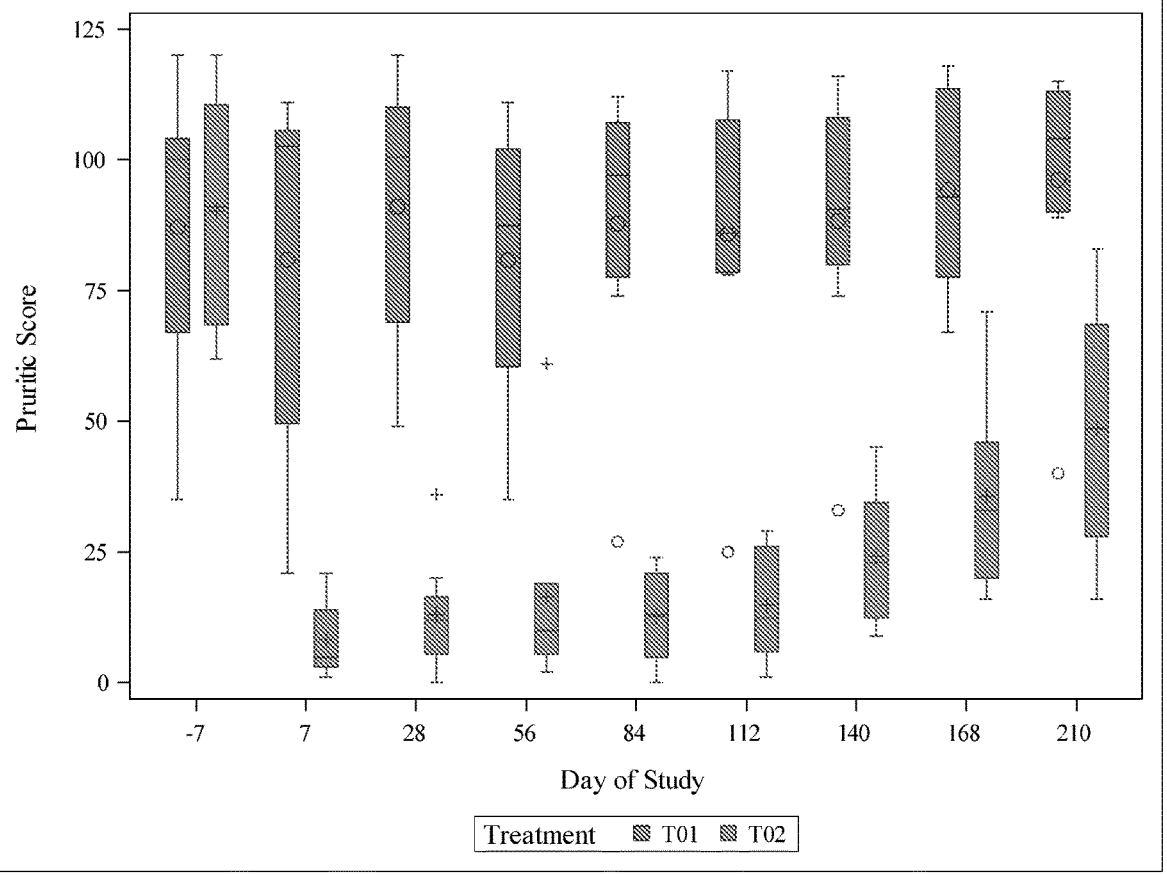

FIG. 11 shows pruritic score box plots for all time points. T01=Placebo 0 mg/kg, T02=ZTS-00008183 4 mg/kg.

Figure 12:
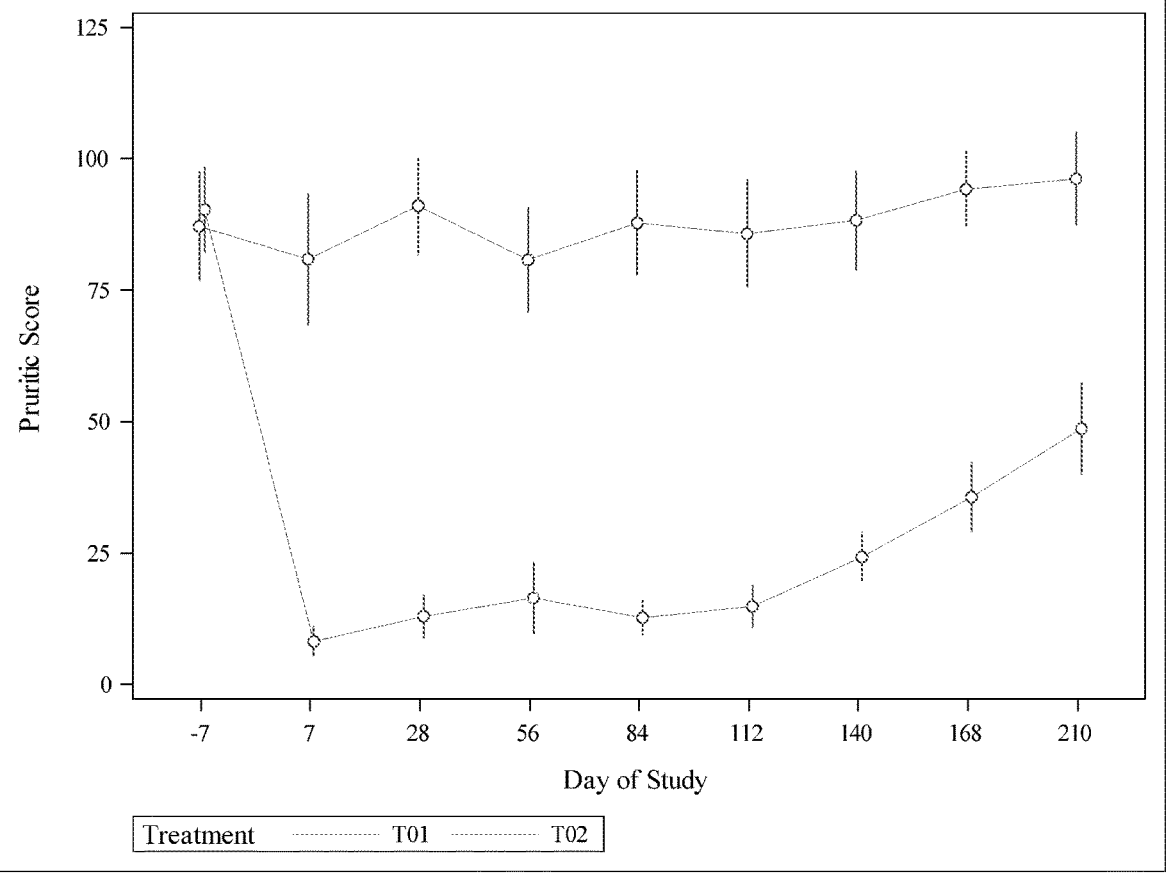

FIG. 12 shows pruritic score plot of arithmetic means by treatment for all time points. Error bars represent standard errors.

Figure 13:
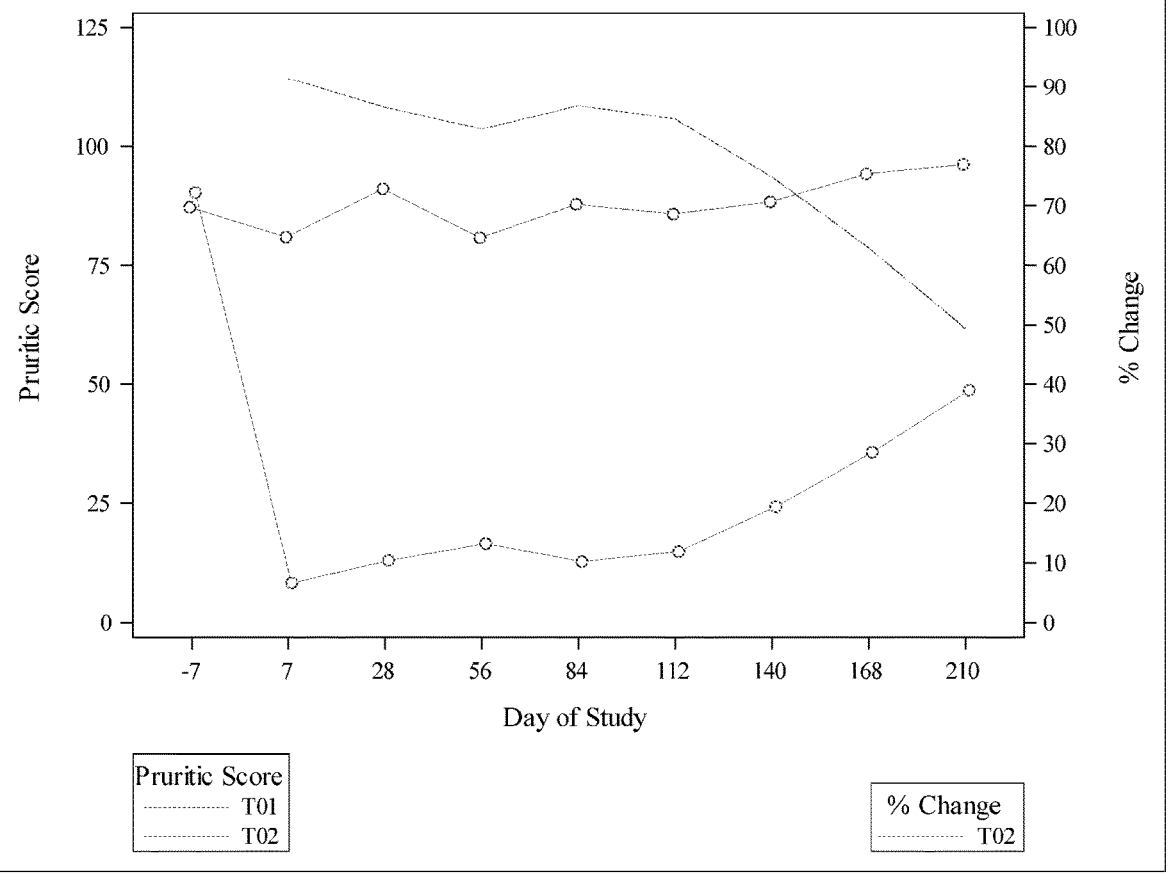

FIG. 13 shows pruritic score plot of arithmetic means and percent change by treatment for all time points. % change in means=100×[mean(T01)−mean(T0X)/mean(T01)], for X=2, 3.

BRIEF DESCRIPTION OF THE SEQUENCE LISTING

SEQ ID NO.: 1 is the amino acid sequence of the mutant canine IgGB constant domain having N434H mutation;

SEQ ID NO.: 2 is the amino acid sequence of the wildtype canine IgGB constant domain;

SEQ ID NO.: 3 is the nucleic acid sequence of the wildtype canine IgG constant domain codon optimized (IgGB_65_WT);

SEQ ID NO.: 4 is the nucleic acid sequence of the wildtype canine IgGB constant domain;

SEQ ID NO.: 5 is the amino acid sequence of IgGB CH1 domain positions 118-215;

SEQ ID NO.: 6 is the amino acid sequence of IgGB hinge Domain positions 217-230;

SEQ ID NO.: 7 is the amino acid sequence of wildtype IgGB CH2 domain positions 231-340;

SEQ ID NO.: 8 is the amino acid sequence of wildtype IgGB CH3 domain positions 341-447;

SEQ ID NO.: 9 is the nucleic acid sequence of IgGB CH1 domain;

SEQ ID NO.: 10 is the nucleic acid sequence of IgGB hinge Domain;

SEQ ID NO.: 11 is the nucleic acid sequence of wildtype IgGB CH2 domain;

SEQ ID NO.: 12 is the nucleic acid sequence of wildtype IgGB CH3 domain;

SEQ ID NO: 13 is a variable heavy chain CDR1 of anti-IL31 antibody referred to herein as 11E12-VH-CDR1;

SEQ ID NO: 14 is a variable heavy chain CDR1 of anti-IL31 antibody referred to herein as 34D03-VH-CDR1;

SEQ ID NO: 15 is a variable heavy chain CDR2 of anti-IL31 antibody referred to herein as 11E12-VH-CDR2;

SEQ ID NO: 16 is a variable heavy chain CDR2 of anti-IL31 antibody referred to herein as 34D03-VH-CDR2;

SEQ ID NO: 17 is a variable heavy chain CDR3 of anti-IL31 antibody referred to herein as 11E12-VH-CDR3;

SEQ ID NO: 18 is a variable heavy chain CDR3 of anti-IL31 antibody referred to herein as 34D03-VH-CDR3;

SEQ ID NO: 19 is a variable light chain CDR1 of anti-IL31 antibody referred to herein as 11E12-VL-CDR1;

SEQ ID NO: 20 is a variable light chain CDR1 of anti-IL31 antibody referred to herein as 34D03-VL-CDR1;

SEQ ID NO: 21 is a variable light chain CDR2 of anti-IL31 antibody referred to herein as 11E12-VL-CDR2;

SEQ ID NO: 22 is a variable light chain CDR2 of anti-IL31 antibody referred to herein as 34D03-VL-CDR2;

SEQ ID NO: 23 is a variable light chain CDR3 of anti-IL31 antibody referred to herein as 11E12-VL-CDR3;

SEQ ID NO: 24 is a variable light chain CDR3 of anti-IL31 antibody referred to herein as 34D03-VL-CDR3;

SEQ ID NO: 25 is a variable light chain sequence of anti-IL31 antibody referred to herein as MU-11E12-VL;

SEQ ID NO: 26 is a variable light chain sequence of anti-IL31 antibody referred to herein as CAN-11E12-VL-cUn-FW2;

SEQ ID NO: 27 is a variable light chain sequence of anti-IL31 antibody referred to herein as CAN-11E12-VL-cUn-13;

SEQ ID NO: 28 is a variable light chain sequence of anti-IL31 antibody referred to herein as MU-34D03-VL;

SEQ ID NO: 29 is a variable light chain sequence of anti-IL31 antibody referred to herein as CAN-34D03-VL-998-1;

SEQ ID NO: 30 is a variable heavy chain sequence of anti-IL31 antibody referred to herein as MU-11E12-VH;

SEQ ID NO: 31 is a variable heavy chain sequence of anti-IL31 antibody referred to herein as CAN-11E12-VH-415-1;

SEQ ID NO: 32 is a variable heavy chain sequence of anti-IL31 antibody referred to herein as MU-34D03-VH;

SEQ ID NO: 33 is a variable heavy chain sequence of anti-IL31 antibody referred to herein as CAN-34D03-VH-568-1;

SEQ ID NO: 34 is the amino acid sequence corresponding to GenBank Accession No. C7G0W1 and corresponds to Canine IL-31 full-length protein;

SEQ ID NO: 35 is the nucleotide sequence corresponding to GenBank Accession No. C7G0W1 and corresponds to the nucleotide sequence encoding Canine IL-31 full-length protein;

SEQ ID NO: 36 is the nucleotide sequence encoding the variable light chain sequence of anti-IL31 antibody referred to herein as MU-11E12-VL;

SEQ ID NO: 37 is the nucleotide sequence encoding the variable heavy chain sequence of anti-IL31 antibody referred to herein as MU-11E12-VH;

SEQ ID NO: 38 is the nucleotide sequence encoding the variable light chain sequence of anti-IL31 antibody referred to herein as MU-34D03-VL;

SEQ ID NO: 39 is the nucleotide sequence encoding the variable heavy chain sequence of anti-IL31 antibody referred to herein as MU-34D03-VH;

SEQ ID NO: 40 is the amino acid sequence for the canine wildtype heavy chain constant region referred to herein as HC-64 (GenBank accession no. AF354264);

SEQ ID NO: 41 is the nucleotide sequence encoding the canine wildtype heavy chain constant region referred to herein as HC-64 (GenBank accession no. AF354264);

SEQ ID NO: 42 is the amino acid sequence for the canine wildtype heavy chain constant region referred to herein as HC-65 (GenBank accession no. AF354265);

SEQ ID NO: 43 is the nucleotide sequence encoding the canine wildtype heavy chain constant region referred to herein as HC-65 (GenBank accession no. AF354265);

SEQ ID NO: 44 is the amino acid sequence for the canine light chain constant region referred to herein as kappa (GenBank Accession No. XP_532962);

SEQ ID NO: 45 is the nucleotide sequence encoding the canine light chain constant region referred to as kappa (GenBank Accession No. XP_532962);

SEQ ID NO: 46 is the nucleotide sequence encoding the variable light chain sequence of anti-IL31 antibody referred to herein as CAN-34D03-VL-998-1;

SEQ ID NO: 47 is the nucleotide sequence encoding the variable heavy chain sequence of anti-IL31 antibody referred to herein as CAN-34D03-VH-568-1;

SEQ ID NO: 48 is the nucleotide sequence encoding the variable light chain sequence of anti-IL31 antibody referred to herein as CAN-11E12-VL-cUn-FW2;

SEQ ID NO: 49 is the nucleotide sequence encoding the variable heavy chain sequence of anti-IL31 antibody referred to herein as CAN-11E12-VH-415-1;

SEQ ID NO: 50 is the nucleotide sequence encoding the variable light chain sequence of anti-IL31 antibody referred to herein as CAN-11E12-VL-cUn-13;

SEQ ID NO: 51 is a variable light chain sequence of anti-IL31 antibody referred to herein as CAN-11E12_VL_cUn_1;

SEQ ID NO: 52 is the nucleotide sequence encoding the variable light chain sequence of anti-IL31 antibody referred to herein as CAN-11E12-VL-cUn-1;

SEQ ID NO: 53 corresponds to the amino acid sequence of the canine IL-31 full-length construct for *E. coli* expression;

SEQ ID NO: 54 is the nucleotide sequence corresponding to the canine IL-31 full-length construct for *E. coli* expression;

SEQ ID NO: 55 is the nucleotide sequence encoding the variable heavy chain sequence of the anti-NGF antibody referred to herein as ZTS-841;

SEQ ID NO: 56 is the amino acid sequence encoding the variable heavy chain sequence of the anti-NGF antibody referred to herein as ZTS-841;

SEQ ID NO: 57 is a variable heavy chain CDR1 of anti-NGF antibody referred to herein as ZTS-841;

SEQ ID NO: 58 is a variable heavy chain CDR2 of anti-NGF antibody referred to herein as ZTS-841;

SEQ ID NO: 59 is a variable heavy chain CDR3 of anti-NGF antibody referred to herein as ZTS-841;

SEQ ID NO: 60 is the nucleotide sequence encoding the variable light chain sequence of the anti-NGF antibody referred to herein as ZTS-841;

SEQ ID NO: 61 is the amino acid sequence encoding the variable light chain sequence of the anti-NGF antibody referred to herein as ZTS-841;

SEQ ID NO: 62 is a variable light chain CDR1 of anti-NGF antibody referred to herein as ZTS-841;

SEQ ID NO: 63 is a variable light chain CDR2 of anti-NGF antibody referred to herein as ZTS-841;

SEQ ID NO: 64 is a variable light chain CDR3 of anti-NGF antibody referred to herein as ZTS-841;

SEQ ID NO: 65 is the amino acid sequence of mutant CH3 domain of IgGB positions 341-447;

SEQ ID NO: 66 is the amino acid sequence of a mutant region within CH3 domain of IgGB;

SEQ ID NO: 67 is the nucleic acid sequence of a light chain of anti-IL31 antibody referred to herein as ZTS-00008183;

SEQ ID NO: 68 is the amino acid sequence of a light chain of anti-IL31 antibody referred to herein as ZTS-00008183;

SEQ ID NO: 69 is the nucleic acid sequence of a heavy chain of anti-IL31 antibody referred to herein as ZTS-00008183;

SEQ ID NO: 70 is the amino acid sequence of a heavy chain of anti-IL31 antibody referred to herein as ZTS-00008183;

SEQ ID NO: 71 is a variable heavy chain CDR1 of anti-TGFβ1,3 antibody referred to herein as ZTS-426;

SEQ ID NO: 72 is a variable heavy chain CDR2 of anti-TGFβ1,3 antibody referred to herein as ZTS-426;

SEQ ID NO: 73 is a variable heavy chain CDR3 of anti-TGFβ1,3 antibody referred to herein as ZTS-426;

SEQ ID NO: 74 is a variable light chain CDR1 of anti-TGFβ1,3 antibody referred to herein as ZTS-426;

SEQ ID NO: 75 is a variable light chain CDR2 of anti-TGFβ1,3 antibody referred to herein as ZTS-426;

SEQ ID NO: 76 is a variable light chain CDR3 of anti-TGFβ1,3 antibody referred to herein as ZTS-426;

SEQ ID NO: 77 is the amino acid sequence of a heavy chain of anti-TGFβ1,3 antibody referred to herein as ZTS-426;

SEQ ID NO: 78 is the nucleic acid sequence of a heavy chain of anti-TGFβ1,3 antibody referred to herein as ZTS-426.

SEQ ID NO: 79 is the amino acid sequence of a light chain of anti-TGFβ1,3 antibody referred to herein as ZTS-426;

SEQ ID NO: 80 is the nucleic acid sequence of a light chain of anti-TGFβ1,3 antibody referred to herein as ZTS-426;

SEQ ID NO: 81 is a variable heavy chain CDR1 of anti-TGFβ1 antibody referred to herein as ZTS-501;

SEQ ID NO: 82 is a variable heavy chain CDR2 of anti-TGFβ1 antibody referred to herein as ZTS-501;

SEQ ID NO: 83 is a variable heavy chain CDR3 of anti-TGFβ1 antibody referred to herein as ZTS-501;

SEQ ID NO: 84 is a variable light chain CDR1 of anti-TGFβ1 antibody referred to herein as ZTS-501;

SEQ ID NO: 85 is a variable light chain CDR2 of anti-TGFβ1 antibody referred to herein as ZTS-501;

SEQ ID NO: 86 is a variable light chain CDR3 of anti-TGFβ1 antibody referred to herein as ZTS-501;

SEQ ID NO: 87 is the amino acid sequence of a heavy chain of anti-TGFβ1 antibody referred to herein as ZTS-501;

SEQ ID NO: 88 is the nucleic acid sequence of a heavy chain of anti-TGFβ1 antibody referred to herein as ZTS-501.

SEQ ID NO: 89 is the amino acid sequence of a light chain of anti-TGFβ1 antibody referred to herein as ZTS-501;

SEQ ID NO: 90 is the nucleic acid sequence of alight chain of anti-TGFβ1 antibody referred to herein as ZTS-501;

SEQ ID NO: 91 is a variable heavy chain CDR1 of anti-TGFβ1,2,3 antibody referred to herein as ZTS-4155;

SEQ ID NO: 92 is a variable heavy chain CDR2 of anti-TGFβ1,2,3 antibody referred to herein as ZTS-4155;

SEQ ID NO: 93 is a variable heavy chain CDR3 of anti-TGFβ1,2,3 antibody referred to herein as ZTS-4155;

SEQ ID NO: 94 is a variable light chain CDR1 of anti-TGFβ1,2,3 antibody referred to herein as ZTS-4155;

SEQ ID NO: 95 is a variable light chain CDR2 of anti-TGFβ1,2,3 antibody referred to herein as ZTS-4155;

SEQ ID NO: 96 is a variable light chain CDR3 of anti-TGFβ1,2,3 antibody referred to herein as ZTS-4155;

SEQ ID NO: 97 is the amino acid sequence of a heavy chain of anti-TGFβ1,2,3 antibody referred to herein as ZTS-4155;

SEQ ID NO: 98 is the nucleic acid sequence of a heavy chain of anti-TGFβ1,2,3 antibody referred to herein as ZTS-4155.

SEQ ID NO: 99 is the amino acid sequence of a light chain of anti-TGFβ1,2,3 antibody referred to herein as ZTS-4155;

SEQ ID NO: 100 is the nucleic acid sequence of a light chain of anti-TGFβ1,2,3 antibody referred to herein as ZTS-4155;

SEQ ID NO: 101 is a variable heavy chain CDR1 of anti-TGFβ1,2,3 antibody referred to herein as ZTS-122;

SEQ ID NO: 102 is a variable heavy chain CDR2 of anti-TGFβ1,2,3 antibody referred to herein as ZTS-122;

SEQ ID NO: 103 is a variable heavy chain CDR3 of anti-TGFβ1,2,3 antibody referred to herein as ZTS-122;

SEQ ID NO: 104 is a variable light chain CDR1 of anti-TGFβ1,2,3 antibody referred to herein as ZTS-122;

SEQ ID NO: 105 is a variable light chain CDR2 of anti-TGFβ1,2,3 antibody referred to herein as ZTS-122;

SEQ ID NO: 106 is a variable light chain CDR3 of anti-TGFβ1,2,3 antibody referred to herein as ZTS-122;

SEQ ID NO: 107 is the amino acid sequence of a heavy chain of anti-TGFβ1,2,3 antibody referred to herein as ZTS-122;

SEQ ID NO: 108 is the nucleic acid sequence of a heavy chain of anti-TGFβ1,2,3 antibody referred to herein as ZTS-122.

SEQ ID NO: 109 is the amino acid sequence of a light chain of anti-TGFβ1,2,3 antibody referred to herein as ZTS-122;

SEQ ID NO: 110 is the nucleic acid sequence of a light chain of anti-TGFβ1,2,3 antibody referred to herein as ZTS-122;

SEQ ID NO: 111 is a variable heavy chain CDR1 of anti-TGFβ1,2,3 antibody referred to herein as ZTS-207;

SEQ ID NO: 112 is a variable heavy chain CDR2 of anti-TGFβ1,2,3 antibody referred to herein as ZTS-207;

SEQ ID NO: 113 is a variable heavy chain CDR3 of anti-TGFβ1,2,3 antibody referred to herein as ZTS-207;

SEQ ID NO: 114 is a variable light chain CDR1 of anti-TGFβ1,2,3 antibody referred to herein as ZTS-207;

SEQ ID NO: 115 is a variable light chain CDR2 of anti-TGFβ1,2,3 antibody referred to herein as ZTS-207;

SEQ ID NO: 116 is a variable light chain CDR3 of anti-TGFβ1,2,3 antibody referred to herein as ZTS-207;

SEQ ID NO: 117 is the amino acid sequence of a heavy chain of anti-TGFβ1,2,3 antibody referred to herein as ZTS-207;

SEQ ID NO: 118 is the nucleic acid sequence of a heavy chain of anti-TGFβ1,2,3 antibody referred to herein as ZTS-207.

SEQ ID NO: 119 is the amino acid sequence of a light chain of anti-TGFβ1,2,3 antibody referred to herein as ZTS-207;

SEQ ID NO: 120 is the nucleic acid sequence of a light chain of anti-TGFβ1,2,3 antibody referred to herein as ZTS-207.

DETAILED DESCRIPTION OF THE INVENTION

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

Definitions

In the present disclosure the singular forms "a," "an," and "the" include the plural reference, and reference to a particular numerical value includes at least that particular value, unless the context clearly indicates otherwise. Thus, for example, a reference to "a molecule" or "a compound" is a reference to one or more of such molecules or compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

In the specification and claims, the numbering of the amino acid residues in an immunoglobulin heavy chain is that of the Eu index as in Kabat et al., Sequences of Proteins of Immunological Interest, 5th Ed. Public Health Service, National Institutes of Health, Bethesda, Md. (1991). The "Eu index as in Kabat" refers to the residue numbering of the IgG antibody and is reflected herein in FIG. 2.

The term "isolated" when used in relation to a nucleic acid is a nucleic acid that is identified and separated from at least one contaminant nucleic acid with which it is ordinarily associated in its natural source. Isolated nucleic acid is in a form or setting different from that in which it is found in nature. Isolated nucleic acid molecules therefore are distinguished from the nucleic acid molecule as it exists in natural cells. An isolated nucleic acid molecule includes a nucleic acid molecule contained in cells that ordinarily express the polypeptide encoded therein where, for example, the nucleic acid molecule is in a plasmid or a chromosomal location different from that of natural cells. The isolated nucleic acid may be present in single-stranded or double-stranded form. When an isolated nucleic acid molecule is to be utilized to express a protein, the oligonucleotide or polynucleotide will contain at a minimum the sense or coding strand, but may contain both the sense and anti-sense strands (i.e., may be double-stranded).

A nucleic acid molecule is "operably linked" or "operably attached" when it is placed into a functional relationship with another nucleic acid molecule. For example, a promoter or enhancer is operably linked to a coding sequence of nucleic acid if it affects the transcription of the sequence; or a ribosome binding site is operably linked to a coding sequence of nucleic acid if it is positioned so as to facilitate translation. A nucleic acid molecule encoding a variant Fc region is operably linked to a nucleic acid molecule encoding a heterologous protein (i.e., a protein or functional fragment thereof which does not, as it exists in nature, comprise an Fc region) if it is positioned such that the expressed fusion protein comprises the heterologous protein or functional fragment thereof adjoined either upstream or downstream to the variant Fc region polypeptide; the heterologous protein may by immediately adjacent to the variant Fc region polypeptide or may be separated therefrom by a linker sequence of any length and composition. Likewise, a polypeptide (used synonymously herein with "protein") molecule is "operably linked" or "operably attached" when it is placed into a functional relationship with another polypeptide.

As used herein the term "functional fragment" when in reference to a polypeptide or protein (e.g., a variant Fc region, or a monoclonal antibody) refers to fragments of that protein which retain at least one function of the full-length polypeptide. The fragments may range in size from six amino acids to the entire amino acid sequence of the full-length polypeptide minus one amino acid. A functional fragment of a variant Fc region polypeptide of the present invention retains at least one "amino acid substitution" as herein defined. A functional fragment of a variant Fc region polypeptide retains at least one function known in the art to be associated with the Fc region (e.g., ADCC, CDC, Fc receptor binding, Clq binding, down regulation of cell surface receptors or may, e.g., increase the in vivo or in vitro half-life of a polypeptide to which it is operably attached).

The term "purified" or "purify" refers to the substantial removal of at least one contaminant from a sample. For example, an antigen-specific antibody may be purified by complete or substantial removal (at least 90%, 91%, 92%, 93%, 94%, 95%, or more preferably at least 96%, 97%, 98% or 99%) of at least one contaminating non-immunoglobulin protein; it may also be purified by the removal of immunoglobulin protein that does not bind to the same antigen. The removal of non-immunoglobulin proteins and/or the removal of immunoglobulins that do not bind a particular antigen results in an increase in the percent of antigen-specific immunoglobulins in the sample. In another example, a polypeptide (e.g., an immunoglobulin) expressed in bacterial host cells is purified by the complete or substantial removal of host cell proteins; the percent of the polypeptide is thereby increased in the sample.

The term "native" as it refers to a polypeptide (e.g., Fc region) is used herein to indicate that the polypeptide has an amino acid sequence consisting of the amino acid sequence of the polypeptide as it commonly occurs in nature or a naturally occurring polymorphism thereof. A native polypeptide (e.g., native Fc region) may be produced by recombinant means or may be isolated from a naturally occurring source.

The term "expression vector" as used herein refers to a recombinant DNA molecule containing a desired coding sequence and appropriate nucleic acid sequences necessary for the expression of the operably linked coding sequence in a particular host organism.

As used herein, the term "host cell" refers to any eukaryotic or prokaryotic cell (e.g., bacterial cells such as *E. coli*, CHO cells, yeast cells, mammalian cells, avian cells, amphibian cells, plant cells, fish cells, and insect cells), whether located in vitro or in situ, or in vivo As used herein, the term "Fc region" refers to a C-terminal region of an immunoglobulin heavy chain. The "Fc region" may be a native sequence Fc region or a variant Fc region. Although the generally accepted boundaries of the Fc region of an immunoglobulin heavy chain might vary, the canine IgG heavy chain Fc region is usually defined to stretch, for example, from an amino acid residue at position 231 to the carboxyl-terminus thereof. In some embodiments, variants comprise only portions of the Fc region and can include or not include the carboxy-terminus. The Fc region of an immunoglobulin generally comprises two constant domains, CH2 and CH3. In some embodiments, variants having one or more of the constant domains are contemplated. In other embodiments, variants without such constant domains (or with only portions of such constant domains) are contemplated.

The "CH2 domain" of a canine IgG Fc region usually extends, for example, from about amino acid 231 to about amino acid 340 (see FIG. 2B). The CH2 domain is unique in that it is not closely paired with another domain. Two N-linked branched carbohydrate chains are interposed between the two CH2 domains of an intact native IgG molecule.

The "CH3 domain" of a canine IgG Fc region generally is the stretch of residues C-terminal to a CH2 domain in an Fc region extending, for example, from about amino acid residue 341 to about amino acid residue 447 (see FIG. 2B).

A "functional Fc region" possesses an "effector function" of a native sequence Fc region. At least one effector function of a polypeptide comprising a variant Fc region of the present invention may be enhanced or diminished with respect to a polypeptide comprising a native Fc region or the parent Fc region of the variant. Examples of effector functions include, but are not limited to: Clq binding; complement dependent cytotoxicity (CDC); Fc receptor binding; antibody-depended cell-mediated cytotoxicity (ADCC); phagocytosis; down regulation of cell surface receptors (e.g., B cell receptor; BCR), etc. Such effector functions may require the Fc region to be operably linked to a binding domain (e.g., an antibody variable domain) and can be assessed using various assays (e.g., Fc binding assay, ADCC assays, CDC assays, target cell depletion from whole or fractionated blood samples, etc.).

A "native sequence Fc region" or "wild type Fc region" refers to an amino acid sequence that is identical to the amino acid sequence of an Fc region commonly found in nature. Exemplary native sequence canine Fc regions are shown in FIG. 2 and include a native sequence of canine IgGB_65 Fc region.

A "variant Fc region" comprises an amino acid sequence that differs from that of a native sequence Fc region (or fragment thereof) by virtue of at least one "amino acid substitution" as defined herein. In preferred embodiments, the variant Fc region has at least one amino acid substitution compared to a native sequence Fc region or in the Fc region of a parent polypeptide, preferably 1, 2, 3, 4 or 5 amino acid substitutions in a native sequence Fc region or in the Fc region of the parent polypeptide. In an alternative embodiment, a variant Fc region may be generated according to the methods herein disclosed and this variant Fc region can be fused to a heterologous polypeptide of choice, such as an antibody variable domain or a non-antibody polypeptide, e.g., binding domain of a receptor or ligand.

As used herein, the term "derivative" in the context of polypeptides refers to a polypeptide that comprises and amino acid sequence which has been altered by introduction of an amino acid residue substitution. The term "derivative" as used herein also refers to a polypeptide which has been modified by the covalent attachment of any type of molecule to the polypeptide. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide possesses a similar or identical function as the polypeptide from which it was derived. It is understood that a polypeptide comprising a variant Fc region of the present invention may be a derivative as defined herein, preferably the derivatization occurs within the Fc region.

"Substantially of canine origin" as used herein in reference to a polypeptide (e.g., an Fc region or a monoclonal antibody), indicates the polypeptide has an amino acid sequence at least 80%, at least 85%, more preferably at least 90%, 91%, 92%, 93%, 94% or even more preferably at least 95%, 95%, 97%, 98% or 99% homologous to that of a native canine amino polypeptide.

The terms "Fc receptor" or "FcR" are used to describe a receptor that binds to an Fc region (e.g., the Fc region of an antibody). The preferred FcR is a native sequence FcR. Moreover, a preferred FcR is one which binds an IgG antibody (a gamma receptor) and includes receptors of the Fc gamma RI, Fc gamma RII, Fc gamma RIII subclasses, including allelic variants and alternatively spliced forms of these receptors. Another preferred FcR includes the neonatal receptor, FcRn, which is responsible for the transfer of maternal IgGs to the fetus (Guyer et al., J. Immunol. 117:587 (1976) and Kim et al., J. Immunol. 24:249 (1994)). Other FcRs, including those to be identified in the future, are encompassed by the term "FcR" herein.

The phrase "antibody-dependent cell-mediated cytotoxicity" and "ADCC" refer to a cell-mediated reaction in which nonspecific cytotoxic cells (e.g., nonspecific) that express FcRs (e.g., Natural Killer ("NK") cells, neutrophils, and macrophages) recognize bound antibody on a target cell and subsequently cause lysis of the target cells. The primary cells for mediating ADCC, NK cells, express Fc gamma RIII only, whereas monocytes express Fc gamma RI, Fc gamma RII and Fc gamma RIII.

As used herein, the phrase "effector cells" refers to leukocytes (preferably canine) which express one or more FcRs and perform effector functions. Preferably, the cells express at least Fc gamma RIII and perform ADCC effector function. Examples of leukocytes which mediate ADCC include PBMC, NK cells, monocytes, cytotoxic T cells and neutrophils. The effector cells may be isolated from a native source (e.g., from blood or PBMCs).

A variant polypeptide with "altered" FcRn binding affinity is one which has either enhanced (i.e., increased, greater or higher) or diminished (i.e., reduced, decreased or lesser) FcRn binding affinity compared to the variant's parent polypeptide or to a polypeptide comprising a native Fc region when measured at pH 6.0. A variant polypeptide which displays increased binding or increased binding affinity to an FcRn binds FcRn with greater affinity than the parent polypeptide. A variant polypeptide which displays decreased binding or decreased binding affinity to an FcRn, binds FcRn with lower affinity than its parent polypeptide. Such variants which display decreased binding to an FcRn may possess little or no appreciable binding to an FcRn, e.g., 0-20% binding to the FcRn compared to a parent polypeptide. A variant polypeptide which binds an FcRn with "enhanced affinity" as compared to its parent polypeptide, is one which binds FcRn with higher binding affinity than the parent polypeptide, when the amounts of variant polypeptide and parent polypeptide in a binding assay are essentially the same, and all other conditions are identical. For example, a variant polypeptide with enhanced FcRn binding affinity may display from about 1.10 fold to about 100 fold (more typically from about 1.2 fold to about 50 fold) increase in FcRn binding affinity compared to the parent polypeptide, where FcRn binding affinity is determined, for example, in an ELISA assay or other method available to one of ordinary skill in the art.

As used herein, an "amino acid substitution" refers to the replacement of at least one existing amino acid residue in a given amino acid sequence with another different "replacement" amino acid residue. The replacement residue or residues may be "naturally occurring amino acid residues" (i.e., encoded by the genetic code) and selected from: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues (s) in a polypeptide chain. Examples of non-naturally occurring amino acid residues include norleucine, ornithine, norvaline, homoserine and other amino acid residue analogues such as those described in Ellman et al. Meth. Enzym. 202: 301-336 (1991).

The term "assay signal" refers to the output from any method of detecting protein-protein interactions, including but not limited to, absorbance measurements from colorimetric assays, fluorescent intensity, or disintegrations per minute. Assay formats could include ELISA, facs, or other methods. A change in the "assay signal" may reflect a change in cell viability and/or a change in the kinetic off-rate, the kinetic on-rate, or both. A "higher assay signal" refers to the measured output number being larger than another number (e.g., a variant may have a higher (larger) measured number in an ELISA assay as compared to the parent polypeptide). A "lower" assay signal refers to the measured output number being smaller than another number (e.g., a variant may have a lower (smaller) measured number in an ELISA assay as compared to the parent polypeptide).

The term "binding affinity" refers to the equilibrium dissociation constant (expressed in units of concentration) associated with each Fc receptor-Fc binding interaction. The binding affinity is directly related to the ratio of the kinetic off-rate (generally reported in units of inverse time, e.g., seconds$^{-1}$) divided by the kinetic on-rate (generally reported in units of concentration per unit time, e.g., molar/second). In general it is not possible to unequivocally state whether changes in equilibrium dissociation constants are due to differences in on-rates, off-rates or both unless each of these parameters are experimentally determined (e.g., by BIA-CORE or SAPIDYNE measurements).

As used herein, the term "hinge region" refers to the stretch of amino acids in canine IgG stretching, for example, from position 216 to position 230 of canine IgG. Hinge regions of other IgG isotypes may be aligned with the IgG sequence by placing the cysteine residues forming inter-heavy chain disulfide (S—S) bonds in the same positions.

"Clq" is a polypeptide that includes a binding site for the Fc region of an immunoglobulin. Clq together with two serine proteases, Clr and Cls, forms the complex Cl, the first component of the CDC pathway.

As used herein, the term "antibody" is used interchangeably with "immunoglobulin" or "Ig," is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity or functional activity. Single chain antibodies, and chimeric, canine, or caninized antibodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. For example, nucleic acids encoding a chimeric or caninized chain can be expressed to produce a contiguous protein. See, e.g., U.S. Pat. Nos. 4,816,567; 4,816,397; WO 86/01533; U.S. Pat. Nos. 5,225,539; and 5,585,089 and 5,698,762. See also, Newman, R. et al. BioTechnology, 10: 1455-1460, 1993, regarding primatized antibody, and Ladner et al., U.S. Pat. No. 4,946,778 and Bird, R. E. et al., Science, 242:423-426, 1988, regarding single chain antibodies. It is understood that all forms of the antibodies comprising an Fc region (or portion thereof) are encompassed herein within the term "antibody." Furthermore, the antibody may be labeled with a detectable label, immobilized on a solid phase and/or conjugated with a heterologous compound (e.g., an enzyme or toxin) according to methods known in the art.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. The antibody fragments preferably retain at least part of the hinge and optionally the CH1 region of an IgG heavy chain. In other preferred embodiments, the antibody fragments comprise at least a portion of the CH2 region or the entire CH2 region.

As used herein, the term "functional fragment", when used in reference to a monoclonal antibody, is intended to refer to a portion of the monoclonal antibody that still retains a functional activity. A functional activity can be, for example, antigen binding activity or specificity, receptor binding activity or specificity, effector function activity and the like. Monoclonal antibody functional fragments include, for example, individual heavy or light chains and fragments thereof, such as VL, VH and Fd; monovalent fragments, such as Fv, Fab, and Fab'; bivalent fragments such as F(ab')2; single chain Fv (scFv); and Fc fragments. Such terms are described in, for example, Harlowe and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990). The term functional fragment is intended to include, for example, fragments produced by protease digestion or reduction of a monoclonal antibody and by recombinant DNA methods known to those skilled in the art.

As used herein, the term "fragment" refers to a polypeptide comprising an amino acid sequence of at least 5, 15, 20, 25, 40, 50, 70, 90, 100 or more contiguous amino acid residues of the amino acid sequence of another polypeptide. In a preferred embodiment, a fragment of a polypeptide retains at least one function of the full-length polypeptide.

As used herein, the term "chimeric antibody" includes monovalent, divalent or polyvalent immunoglobulins. A monovalent chimeric antibody is a dimer formed by a chimeric heavy chain associated through disulfide bridges with a chimeric light chain. A divalent chimeric antibody is a tetramer formed by two heavy chain-light chain dimers associated through at least one disulfide bridge. A chimeric heavy chain of an antibody for use in canine comprises an antigen-binding region derived from the heavy chain of a non-canine antibody, which is linked to at least a portion of a canine heavy chain constant region, such as CH1 or CH2. A chimeric light chain of an antibody for use in canine comprises an antigen binding region derived from the light chain of a non-canine antibody, linked to at least a portion of a canine light chain constant region (CL). Antibodies, fragments or derivatives having chimeric heavy chains and light chains of the same or different variable region binding specificity, can also be prepared by appropriate association of the individual polypeptide chains, according to known method steps. With this approach, hosts expressing chimeric heavy chains are separately cultured from hosts expressing chimeric light chains, and the immunoglobulin chains are separately recovered and then associated. Alternatively, the hosts can be co-cultured and the chains allowed to associate spontaneously in the culture medium, followed by recovery of the assembled immunoglobulin or fragment or both the heavy and light chains can be expressed in the same host cell. Methods for producing chimeric antibodies are well known in the art (see, e.g., U.S. Pat. Nos. 6,284,471; 5,807,715; 4,816,567; and 4,816,397).

As used herein, "caninized" forms of non-canine (e.g., murine) antibodies (i.e., caninized antibodies) are antibodies that contain minimal sequence, or no sequence, derived from non-canine immunoglobulin. For the most part, caninized antibodies are canine immunoglobulins (recipient antibody) in which residues from a hypervariable region of the recipient are replaced by residues from a hypervariable region of a non-canine species (donor antibody) such as mouse, rat, rabbit, human or nonhuman primate having the desired specificity, affinity, and capacity. In some instances, framework region (FR) residues of the canine immunoglobulin are replaced by corresponding non-canine residues. Furthermore, caninized antibodies may comprise residues that are not found in the recipient antibody or in the donor antibody. These modifications are generally made to further refine antibody performance. In general, the caninized antibody will comprise substantially all of at least one, and typically two, variable domains, in which all or substantially all of the hypervariable loops (CDRs) correspond to those of a non-canine immunoglobulin and all or substantially all of the FR residues are those of a canine immunoglobulin sequence. The caninized antibody may also comprise at least a portion of an immunoglobulin constant region (Fc), typically that of a canine immunoglobulin.

As used herein, the term "immunoadhesin" designates antibody-like molecules which combine the binding domain of a heterologous "adhesin" protein (e.g., a receptor, ligand or enzyme) with an immunoglobulin constant domain. Structurally, immunoadhesins comprise a fusion of the adhesin amino acid sequence with the desired binding specificity which is other than the antigen recognition and binding site (antigen combining site) of an antibody (i.e., is "heterologous") with an immunoglobulin constant domain sequence.

As used herein, the term "ligand binding domain" refers to any native receptor or any region or derivative thereof retaining at least a qualitative ligand binding ability of a corresponding native receptor. In certain embodiments, the receptor is from a cell-surface polypeptide having an extra-cellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules (e.g., E-, L-, and P-selectins).

As used herein, the term "receptor binding domain" refers to any native ligand for a receptor, including, e.g., cell adhesion molecules, or any region or derivative of such native ligand retaining at least a qualitative receptor binding ability of a corresponding native ligand.

As used herein, an "isolated" polypeptide is one that has been identified and separated and/or recovered from a com-ponent of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the iso-lated polypeptide is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or nonreducing conditions using Coomassie blue or silver stain. Isolated polypeptide includes the polypeptide in situ within recombinant cells since at least one component of the polypeptide's natural environment will not be present. Ordinarily, however, isolated polypeptide will be prepared by a least one purification step.

As used herein, the term "disorder" and "disease" are used interchangeably to refer to any condition that would benefit from treatment with a variant polypeptide (a polypeptide comprising a variant Fc region of the invention), including chronic and acute disorders or diseases (e.g., pathological conditions that predispose a patient to a particular disorder).

As used herein, the term "receptor" refers to a polypeptide capable of binding at least one ligand. The preferred receptor is a cell-surface or soluble receptor having an extracellular ligand-binding domain and, optionally, other domains (e.g., transmembrane domain, intracellular domain and/or mem-brane anchor). A receptor to be evaluated in an assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase or labeled directly and used as a probe.

Canine Wildtype IgG

Canine IgGs are well known in the art and fully described, for example, in Bergeron et al., 2014, Vet Immunol Immu-nopathol., vol. 157 (1-2), pages 31-41. In one embodiment, canine IgG is $IgG_A$. In another embodiment, canine IgG is $IgG_B$. In yet another embodiment, canine IgG is $IgG_C$. In further embodiment, canine IgG is $IgG_D$. In a particular embodiment, canine IgG is $IgG_B\_65$.

The amino acid and nucleic acid sequences of $IgG_A$, $IgG_B$, $IgG_C$, and $IgG_D$ are also well known in the art.

In one example, IgG of the invention comprises a constant domain, for example, CH1, CH2, or CH3 domains, or a combination thereof. In another example, the constant domain of the invention comprises Fc region, including, for example, CH2 or CH3 domains or a combination thereof.

In a particular example, the wild-type constant domain comprises the amino acid sequence set forth in SEQ ID NO.: 2. In some embodiments, the wild-type IgG constant domain is a homologue, a variant, an isomer, or a functional frag-ment of SEQ ID NO.: 2, but without any mutation at position 434. Each possibility represents a separate embodiment of the present invention.

IgGs constant domains also include polypeptides with amino acid sequences substantially similar to the amino acid sequence of the heavy and/or light chain. Substantially the same amino acid sequence is defined herein as a sequence with at least 70%, 75%, 80%, 85%, 90%, 95%, or 99% identity to a compared amino acid sequence, as determined by the FASTA search method in accordance with Pearson and Lipman, Proc. Natl. Acad. Sci. USA 85:2444-2448 (1988).

The present invention also includes nucleic acid mol-ecules that encode IgGs or portion thereof, described herein. In one embodiment, the nucleic acids may encode an anti-body heavy chain comprising, for example, CH1, CH2, CH3 regions, or a combination thereof. In another embodiment, the nucleic acids may encode an antibody heavy chain comprising, for example, any one of the VH regions or a portion thereof, or any one of the VH CDRs, including any variants thereof. The invention also includes nucleic acid molecules that encode an antibody light chain comprising, for example, any one of the CL regions or a portion thereof, any one of the VL regions or a portion thereof or any one of the VL CDRs, including any variants thereof. In certain embodiments, the nucleic acid encodes both a heavy and light chain, or portions thereof.

The amino acid sequence of the wild-type constant domain set forth in SEQ ID NO.: 2 is encoded by the nucleic acid sequence set forth in in SEQ ID NO.: 4.

Modified Canine IgG

The inventors of the instant application have found that substituting the amino acid residue asparagine (Asn or N) at position 434 with another amino acid surprisingly and unexpectedly enhanced the affinity to FcRn and increased the half-life of IgG. The terms, position 434, as used herein, refers to a position numbered according to the EU index as in Kabat (Kabat et al., Sequences of Proteins of Immuno-logical Interest, 5th Ed. Public Health Service, National Institutes of Health, Bethesda, Md. (1991)).

Accordingly, in one embodiment, the invention provides a modified IgG comprising: a canine IgG constant domain comprising at least one amino acid substitution relative to a wild-type canine IgG constant domain, wherein said substitution is at amino acid residue 434, numbered according to the EU index as in Kabat. The asparagine at position 434 can be substituted with any other amino acid. For example, the asparagine at position 434 can be substituted with histidine (i.e., N434H), serine (i.e., N434S), alanine (i.e., N434A), phenylalanine (i.e., N434F), glycine (i.e., N434G), isoleucine (i.e., N434I), lysine (i.e., N434K), leucine (i.e., N434L), methionine (i.e., N434M), glutamine (i.e., N434Q), arginine (i.e., N434R), threonine (i.e., N434T), valine (i.e., N434V), tryptophan (i.e., N434W), tyrosine (i.e., N434Y), cysteine (i.e., N434C), aspartic acid (i.e., N434D), glutamic acid (i.e., N434E), or proline (i.e., N434P). In a particular embodiment, the substitution is a substitution with histidine (i.e., N434H).

In a particular example, the mutant constant domain of the invention comprises the amino acid sequence set forth in SEQ ID NO.: 1. In some embodiments, the mutant IgG constant domain is a homologue, a variant, an isomer, or a functional fragment of SEQ ID NO.: 1, but with mutation at position 434. Each possibility represents a separate embodiment of the present invention.

The amino acid sequence of the mutant constant domain set forth in SEQ ID NO.: 1 is encoded by its corresponding mutant nucleic acid sequence, for example, a mutant form of the nucleic acid sequence set forth in in SEQ ID NO.: 4. In some embodiments, the nucleic acid codon corresponding to position 434 of a mutant form comprises CAC or CAT.

In some embodiments, the mutant constant domain of the invention comprises the amino acid sequence set forth in SEQ ID NO.: 65 or 66. In some embodiments, the mutant IgG constant domain is a homologue, a variant, an isomer, or a functional fragment of SEQ ID NO.: 65 or 66, but with mutation at position 434. Each possibility represents a separate embodiment of the present invention.

The amino acid sequence of the mutant constant domain set forth in SEQ ID NO.: 65 or 66 is encoded by its corresponding mutant nucleic acid sequence.

In one aspect, the modified IgG of the invention provides the half-life for a period ranging from about 10 days to about 35 days. In one embodiment, the modified IgG of the invention provides the half-life for about 10, 12, 15, 17, 19, 20, 23, 26, 28, 30, 33, or 35 days. In a particular embodiment, the modified IgG of the invention provides the half-life for more than 30 days.

In one aspect, the modified IgG of the invention maintains a therapeutic serum level for a period ranging from about 1 month to about 7 months. In one embodiment, the modified IgG of the invention maintains a therapeutic serum level for about 7, 14, 28, 56, 84, 112, 140, 168, or 210 days. In a particular embodiment, the modified IgG of the invention maintains a therapeutic serum level for more than 3 months.

Methods for Making Antibody Molecules of the Invention

Methods for making antibody molecules are well known in the art and fully described in U.S. Pat. Nos. 8,394,925; 8,088,376; 8,546,543; 10,336,818; and 9,803,023 and U.S. Patent Application Publication 20060067930, which are incorporated by reference herein in their entirety. Any suitable method, process, or technique, known to one of skilled in the art, can be used. An antibody molecule having a variant Fc region of the invention may be generated according to the methods well known in the art. In some embodiments, the variant Fc region can be fused to a heterologous polypeptide of choice, such as an antibody variable domain or binding domain of a receptor or ligand.

With the advent of methods of molecular biology and recombinant technology, a person of skilled in the art can produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as H2L2 and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or 'V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

The present invention further provides a vector including at least one of the nucleic acids described above. Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an antibody or portion. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding canine IgG sequences can be identified. It is also intended that the antibody coding regions for use in the present invention could also be provided by altering existing antibody genes using standard molecular biological techniques that result in variants of the antibodies and peptides described herein. Such variants include, but are not limited to deletions, additions and substitutions in the amino acid sequence of the antibodies or peptides.

For example, one class of substitutions is conservative amino acid substitutions. Such substitutions are those that substitute a given amino acid in a canine antibody peptide by another amino acid of like characteristics. Typically seen as conservative substitutions are the replacements, one for another, among the aliphatic amino acids Ala, Val, Leu, and lie; interchange of the hydroxyl residues Ser and Thr, exchange of the acidic residues Asp and Glu, substitution between the amide residues Asn and Gin, exchange of the basic residues Lys and Arg, replacements among the aromatic residues Phe, Tyr, and the like. Guidance concerning which amino acid changes are likely to be phenotypically silent is found in Bowie et al., 247 *Science* 1306-10 (1990).

Variant canine antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 *Science* 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 *J. Mol. Biol.* 899-904 (1992); de Vos et al., 255 *Science* 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W. H. Freeman & Co., N.Y., 1993). Many detailed reviews are available on this subject, such as by Wold, Posttranslational Covalent Modification of proteins, 1-12 (Johnson, ed., Academic Press, N.Y., 1983); Seifter et al. 182 *Meth. Enzymol.* 626-46 (1990); and Rattan et al. 663 *Ann. NY Acad. Sci.* 48-62 (1992).

In another aspect, the invention provides antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (251,1311), carbon (4C), sulfur (35S), indium, tritium ($H^3$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegylation), and are well-known in the art. See U.S. Patent. Appl. Pub. No. 20030031671.

In some embodiments, the nucleic acids encoding a subject antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing. Traditionally, monoclonal antibodies have been produced as native molecules in murine hybridoma lines. In addition to that technology, the present invention provides for recombinant DNA expression of the antibodies. This allows the production of antibodies, as well as a spectrum of antibody derivatives and fusion proteins in a host species of choice.

A nucleic acid sequence encoding at least one antibody, portion or polypeptide of the invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, N Y, 1982 and 1989), and Ausubel et al. 1993 supra, may be used to construct nucleic acid sequences which encode an antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin. Any other suitable mammalian cell, known in the art, may also be used.

In one embodiment, the nucleotide sequence of the invention will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli (such as, for example, pBR322, CoIE1, pSC101, pACYC 184, .pi.vX). Such plasmids are, for example, disclosed by Maniatis et al., 1989 supra; Ausubel et al, 1993 supra. Bacillus plasmids include pC194, pC221, pT127, etc. Such plasmids are disclosed by Gryczan, in THE MOLEC. BIO. OF THE BACILLI 307-329 (Academic Press, N Y, 1982). Suitable Streptomyces plasmids include p1J101 (Kendall et al., 169 J. Bacteriol. 4177-83 (1987), and Streptomyces bacteriophages such as phLC31 (Chater et al., in SIXTH INT'L SYMPOSIUM ON ACTINOMYCETALES BIO. 45-54 (Akademiai Kaido, Budapest, Hungary 1986). Pseudomonas plasmids are reviewed in John et al., 8 Rev. Infect. Dis. 693-704 (1986); lzaki, 33 Jpn. J. Bacteriol. 729-42 (1978); and Ausubel et al., 1993 supra.

Alternatively, gene expression elements useful for the expression of cDNA encoding antibodies or peptides include, but are not limited to, (a) viral transcription promoters and their enhancer elements, such as the SV40 early promoter (Okayama et al., 3 Mol. Cell. Biol. 280 (1983), Rous sarcoma virus LTR (Gorman et al., 79 Proc. Natl. Acad. Sci., USA 6777 (1982), and Moloney murine leukemia virus LTR (Grosschedl et al., 41 Cell 885 (1985); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements. For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the immunoglobulin chain gene product are then transfected singly with a peptide or H or L chain-encoding gene, or are co-transfected with H and L chain gene. The transfected recipient cells are cultured under conditions that permit expression of the incorporated genes and the expressed immunoglobulin chains or intact antibodies or fragments are recovered from the culture.

In one embodiment, the fused genes encoding the peptide or H and L chains, or portions thereof are assembled in separate expression vectors that are then used to cotransfect a recipient cell. Alternatively the fused genes encoding the H and L chains can be assembled on the same expression vector. For transfection of the expression vectors and production of the antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of canine or non-canine origin, hybridoma cells of canine or non-canine origin, or interspecies heterohybridoma cells.

The expression vector carrying an antibody construct or polypeptide of the invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 *Science* 1538 (1988).

Yeast may provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of peptides, antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.,) IRL Press, Oxford, UK 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, N.Y. (1994-2001); Colligan et al., eds. Current Protocols in Protein Science, John Wiley & Sons, NY, N.Y. (1997-2001).

Host mammalian cells may be grown in vitro or in vivo. Mammalian cells provide posttranslational modifications to immunoglobulin protein molecules including leader peptide removal, folding and assembly of H and L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Many vector systems are available for the expression of cloned peptides H and L chain genes in mammalian cells (see Glover, 1985 supra). Different approaches can be followed to obtain complete H2L2 antibodies. It is possible to co-express H and L chains in the same cells to achieve intracellular association and linkage of H and L chains into complete tetrameric H2L2 antibodies and/or peptides. The co-expression can occur by using either the same or different plasmids in the same host. Genes for both H and L chains and/or peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. cell lines producing peptides and/or H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

In another aspect, the invention provides an antibody comprising: a canine IgG constant domain comprising at least one amino acid substitution relative to a wild-type canine IgG constant domain, wherein said substitution is at amino acid residue 434. In one embodiment the substitution is a substitution of asparagine at position 434 with histidine (N434H).

The antibody having the substitution can be any suitable antibody known to one of skilled in the art. In one example, the antibody is an anti-IL31 antibody. In another example, the antibody is an anti-NGF antibody. In yet another example, the antibody is an anti-TGFβ antibody.

Anti-IL31 antibody, without the substitution described herein, is well known in the art and fully described in, for example, U.S. Pat. Nos. 10,526,405; 10,421,807; 9,206,253; and 8,790,651. Also, anti-NGF antibody, without the substitution described herein, is also well known in the art and fully described in, for example, U.S. Pat. Nos. 10,125,192; 10,093,725; 9,951,128; 9,617,334; and 9,505,829. Furthermore, anti-TGFβ antibody, without the substitution described herein, is also well known in the art and fully described in, for example, U.S. Patent Applications 63/036,092 and 63/248,679 and PCT International Patent Application PCT/US2021/036347.

In one embodiment, the anti-IL31 antibody of the invention (i.e., antibody having the substitution) reduces, inhibits, or neutralizes an IL-31-mediated pruritic or allergic condition. In another embodiment, the anti-IL31 antibody of the invention reduces, inhibits, or neutralizes IL-31 activity in a dog.

In one example, the anti-IL31 antibody of the invention binds to IL-31 at a region between about amino acid residues 95 and 125 of the canine IL-31 amino acid sequence of SEQ ID NO: 44, preferably at a region between about amino acid residues 102 and 122 of the canine IL-31 sequence of SEQ ID NO: 44.

VL, VH, and CDR sequences of the anti-IL31 antibodies are well known in the art and fully described in, for example, U.S. Pat. Nos. 10,526,405; 10,421,807; 9,206,253; and 8,790,651. In one example, the anti-IL31 antibody of the invention may include at least one of the following combinations of complementary determining region (CDR) sequences: (1) 11E12: variable heavy (VH)-CDR1 of SEQ ID NO: 13, VH-CDR2 of SEQ ID NO: 15, VH-CDR3 of SEQ ID NO: 17, variable light (VL)-CDR1 of SEQ ID NO: 19, VL-CDR2 of SEQ ID NO: 21, and VL-CDR3 of SEQ ID NO: 23; or (2) 34D03: VH-CDR1 of SEQ ID NO: 14, VH-CDR2 of SEQ ID NO: 16, VH-CDR3 of SEQ ID NO: 18, VL-CDR1 of SEQ ID NO: 20, VL-CDR2 of SEQ ID NO: 22, and VL-CDR3 of SEQ ID NO: 24. In some embodiments, the anti-IL31 antibody of the invention may include at least one CDR described herein.

In one embodiment, the anti-IL31 antibody of the invention may include a variable light chain comprising the amino acid sequence set forth in SEQ ID NO: 25 (MU-11E12-VL), SEQ ID NO: 26 (CAN-11E12-VL-cUn-FW2), SEQ ID NO; 27 (CAN-11E12-VL-cUn-13), SEQ ID NO: 28 (MU-34D03-VL) or SEQ ID NO: 29 (CAN-34D03-VL-998-1).

In another embodiment, the anti-IL31 antibody of the invention may include a variable heavy chain comprising the amino acid sequence set forth in SEQ ID NO: 30 (MU-11E12-VH), SEQ ID NO: 31 (CAN-11E12-VH-415-1), SEQ ID NO: 32 (MU-34D03-VH) or SEQ ID NO: 33 (CAN-34D03-VH-568-1).

In one embodiment, the mutant anti-NGF antibody of the invention (i.e., antibody having the substitution) reduces, inhibits, or neutralizes NGF activity in an animal, and/or enhanced ability to inhibit NGF binding to Trk A and p75, in order to treat an NGF-mediated pain or condition.

VL, VH, and CDR sequences of the anti-NGF antibodies are also well known in the art and fully described in, for example, U.S. Pat. Nos. 10,125,192; 10,093,725; 9,951,128; 9,617,334; and 9,505,829. In one example, the anti-NGF antibody of the invention may include at least one of the following complementary determining region (CDR) sequences: ZTS-841: variable heavy (VH)-CDR1 of SEQ ID NO: 57, VH-CDR2 of SEQ ID NO: 58, VH-CDR3 of SEQ ID NO: 59, variable light (VL)-CDR1 of SEQ ID NO: 62, VL-CDR2 of SEQ ID NO: 63, and VL-CDR3 of SEQ ID NO: 64. In some embodiments, VL-CDR2 has GNG residues of SEQ ID NO: 63.

In one embodiment, the anti-NGF antibody of the invention may include a variable light chain comprising the amino acid sequence set forth in SEQ ID NO: 61 (CAN-ZTS-841-VL).

In another embodiment, the anti-NGF antibody of the invention may include a variable heavy chain comprising the amino acid sequence set forth in SEQ ID NO: 56 (CAN-ZTS-841-VH).

In one embodiment, the anti-TGFβ antibody of the invention (i.e., antibody having the substitution) reduces, inhibits, or neutralizes an TGFβ-mediated disease or condition, for example, chronic kidney disease. In another embodiment, the anti-TGFβ antibody of the invention reduces, inhibits, or neutralizes TGFβ activity in a dog. The anti-TGFβ antibody of the invention can bind to TGFβ1, 2, 3, or a combination thereof. For instance, in one embodiment, the anti-TGFβ antibody of the invention binds to TGFβ1. In another embodiment, the anti-TGFβ antibody of the invention binds to TGFβ2. In another embodiment, the anti-TGFβ antibody of the invention binds to TGFβ3. In yet another embodiment, the anti-TGFβ antibody of the invention binds to TGFβ1, TGFβ2, TGFβ3, or a combination thereof.

VL, VH, and CDR sequences of the anti-TGFβ antibodies are well known in the art and fully described in, for example, U.S. Patent Applications 63/036,092 and 63/248,679 and PCT International Patent Application PCT/US2021/036347. In one example, the anti-TGFβ antibody of the invention may include at least one of the following combinations of complementary determining region (CDR) sequences: (1) ZTS-426: variable heavy (VH)-CDR1 of SEQ ID NO: 71, VH-CDR2 of SEQ ID NO: 72, VH-CDR3 of SEQ ID NO: 73, variable light (VL)-CDR1 of SEQ ID NO: 74, VL-CDR2 of SEQ ID NO: 75, and VL-CDR3 of SEQ ID NO: 76; or (2) ZTS-501: VH-CDR1 of SEQ ID NO: 81, VH-CDR2 of SEQ ID NO: 82, VH-CDR3 of SEQ ID NO: 83, VL-CDR1 of SEQ ID NO: 84, VL-CDR2 of SEQ ID NO: 85, and VL-CDR3 of SEQ ID NO: 86; or (3) ZTS-4155: VH-CDR1 of SEQ ID NO: 91, VH-CDR2 of SEQ ID NO: 92, VH-CDR3 of SEQ ID NO: 93, VL-CDR1 of SEQ ID NO: 94, VL-CDR2 of SEQ ID NO: 95, and VL-CDR3 of SEQ ID NO: 96; or (4) ZTS-122: VH-CDR1 of SEQ ID NO: 101, VH-CDR2 of SEQ ID NO: 102, VH-CDR3 of SEQ ID NO: 103, VL-CDR1 of SEQ ID NO: 104, VL-CDR2 of SEQ ID NO: 105, and VL-CDR3 of SEQ ID NO: 106; or (5) ZTS-207: VH-CDR1 of SEQ ID NO: 111, VH-CDR2 of SEQ ID NO: 112, VH-CDR3 of SEQ ID NO: 113, VL-CDR1 of SEQ ID NO: 114, VL-CDR2 of SEQ ID NO: 115, and VL-CDR3 of SEQ ID NO: 116.

In some embodiments, the anti-TGFβ antibody of the invention may include at least one CDR described herein.

In one embodiment, the anti-TGFβ antibody of the invention may include a variable heavy chain comprising the amino acid sequence set forth in SEQ ID NO: 77 (ZTS-426), SEQ ID NO: 87 (ZTS-501), SEQ ID NO: 97 (ZTS-4155), SEQ ID NO: 107 (ZTS-122) or SEQ ID NO: 117 (ZTS-207).

In another embodiment, the anti-TGFβ antibody of the invention may include a variable light chain comprising the amino acid sequence set forth in SEQ ID NO: 79 (ZTS-426), SEQ ID NO: 89 (ZTS-501), SEQ ID NO: 99 (ZTS-4155), SEQ ID NO: 109 (ZTS-122) or SEQ ID NO: 119 (ZTS-207).

Pharmaceutical and Veterinary Applications

The invention also provides a pharmaceutical composition comprising molecules of the invention and one or more pharmaceutically acceptable carriers. More specifically, the invention provides for a pharmaceutical composition comprising a pharmaceutically acceptable carrier or diluent and, as active ingredient, an antibody or peptide according to the invention.

"Pharmaceutically acceptable carriers" include any excipient which is nontoxic to the cell or animal being exposed thereto at the dosages and concentrations employed. The pharmaceutical composition may include one or additional therapeutic agents.

"Pharmaceutically acceptable" refers to those compounds, materials, compositions, and/or dosage forms which are, within the scope of sound medical judgment, suitable for contact with the tissues of animals without excessive toxicity, irritation, allergic response, or other problem complications commensurate with a reasonable benefit/risk ratio.

Pharmaceutically acceptable carriers include solvents, dispersion media, buffers, coatings, antibacterial and anti-fungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof.

The pharmaceutical compositions of the invention may be formulated in a variety of ways, including for example, liquid, semi-solid, or solid dosage forms, such as liquid solutions (e.g., injectable and infusible solutions), dispersions or suspensions, liposomes, suppositories, tablets, pills, or powders. In some embodiments, the compositions are in the form of injectable or infusible solutions. The composition can be in a form suitable for intravenous, intraarterial, intramuscular, subcutaneous, parenteral, transmucosal, oral, topical, or transdermal administration. The composition may be formulated as an immediate, controlled, extended or delayed release composition.

The compositions of the invention can be administered either as individual therapeutic agents or in combination with other therapeutic agents. They can be administered alone, but are generally administered with a pharmaceutical carrier selected on the basis of the chosen route of administration and standard pharmaceutical practice. Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed.

In some desired embodiments, the antibodies are administered by parenteral injection. For parenteral administration, antibodies or molecules can be formulated as a solution, suspension, emulsion or lyophilized powder in association with a pharmaceutically acceptable parenteral vehicle. For example, the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies or molecules of the invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate. The compositions containing the present antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art. In therapeutic application, compositions are administered to a subject already suffering from a disease, in an amount sufficient to cure or at least partially arrest or alleviate the disease and its complications.

Effective doses of the compositions of the present invention, for treatment of conditions or diseases as described herein vary depending upon many different factors, including, for example, but not limited to, the pharmacodynamic characteristics of the particular agent, and its mode and route of administration; target site; physiological state of the animal; other medications administered; whether treatment is prophylactic or therapeutic; age, health, and weight of the recipient; nature and extent of symptoms kind of concurrent treatment, frequency of treatment, and the effect desired.

Single or multiple administrations of the compositions can be carried out with dose levels and pattern being selected by the treating veterinarian. In any event, the pharmaceutical formulations should provide a quantity of the antibody(ies) of this invention sufficient to effectively treat the subject. In an exemplary embodiment, the composition of the invention is administered bimonthly, once-in-three months, once-in-four months, once-in-five months, once-in-six months, or once-in-seven months.

Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

In another aspect, the compositions of the invention can be used, for example, in the treatment of various diseases and disorders in dogs. As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

The mutant molecule of the invention can be used to treat any suitable disease or disorder. For example, the mutant anti-IL31 antibody of the invention can be used to treat an IL-31-mediated pruritic or allergic condition. The examples of IL-31-mediated pruritic condition include, for example, but not limited to, atopic dermatitis, eczema, psoriasis, scleroderma, and pruritis. The examples of IL-31-mediated allergic condition include, for example, but not limited to, allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity.

The mutant anti-NGF antibody of the invention can be used to treat an NGF-mediated pain or a condition. The examples of a pain include, for example, but not limited to, a chronic pain, an inflammatory pain, a post-operative incision pain, a neuropathic pain, a fracture pain, an osteoporotic fracture pain, a post-herpetic neuralgia, a cancer pain, a pain resulting from burns, a pain associated with wounds, a pain associated with trauma, a neuropathic pain, a pain associated with a musculoskeletal disorder, a rheumatoid arthritis, an osteoarthritis, an ankylosing spondylitis, a seronegative (non-rheumatoid) an arthropathies, a non-articular rheumatism, a periarticular disorder, or a peripheral neuropathy. In a particular embodiment, the pain is an osteoarthritis pain.

The mutant anti-TGFβ antibody of the invention can be used to treat a TGFβ-mediated disease or a condition. The examples of a TGFβ-mediated disease or a condition include, for example, but not limited to, a chronic kidney disease.

All patents and literature references cited in the present specification are hereby incorporated by reference in their entirety.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Example 1

Construction of Canine IgG Fc Mutants

Figure 1:
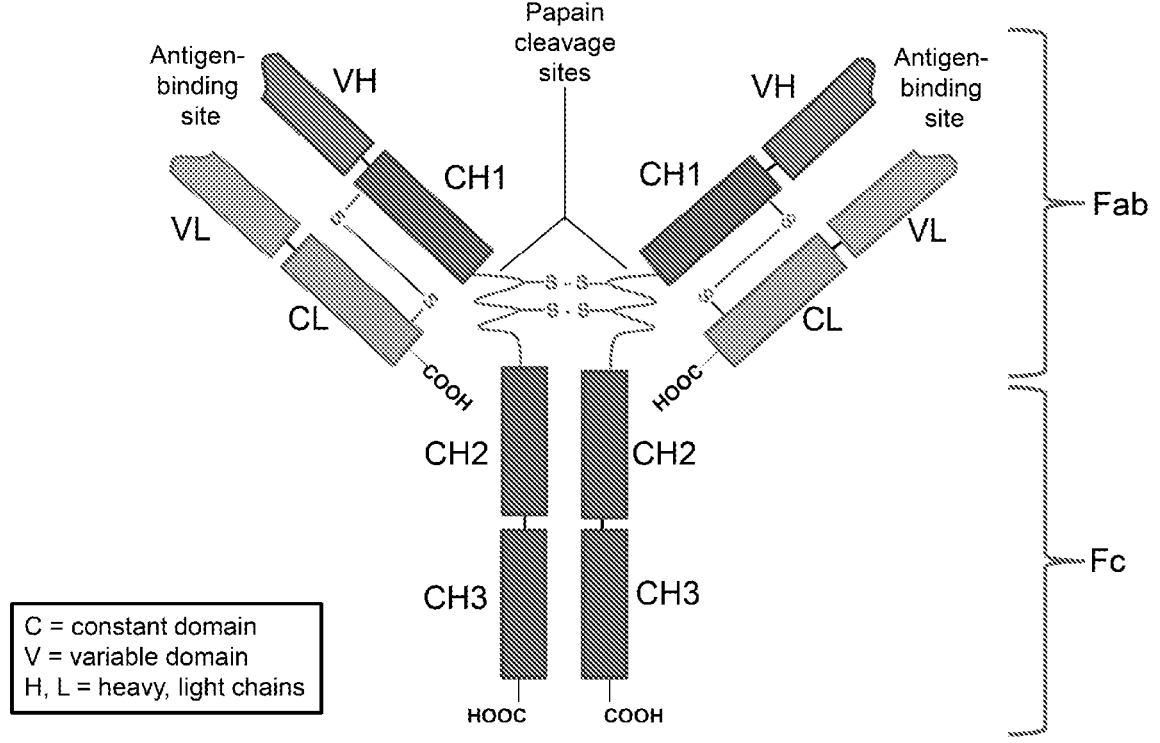
FIG. 1 illustrates domain structure of IgG. Fc mutation N434H was made in the CH3 domain to increase IgG half-life by increasing affinity to FcRn at pH6.

Construction of all canine IgGs (FIG. 1) was carried out as described by Bergeron et al. (Bergeron et al., 2014, *Vet Immunol Immunopathol.*, vol. 157(1-2), pages 31-41), in which plasmids containing sequence encoding for canine constant regions for the IgGB (65) sub-class were utilized and VH/VL sequences for each mAb investigated herein were inserted upstream and in frame with the nucleotides encoding for the constant domains. Mutations were incorporated into position N434 of the CH3 domain (FIG. 2) of each plasmid using Agilent's QuikChange II Mutagenesis and associated Agilent primer design tools for single-site directed mutagenesis (https://www.agilent.com/store/primerDesignProgram.jsp).

Antibody constructs were transiently expressed either in HEK 293 cells using a standard lipofectamine transfection protocol (Invitrogen Life Technologies, Carlsbad, CA, USA) or into CHO cells using the ExpiCHO transient system (ThermoFisher Scientific) kit protocols. ExpiCHO expression followed protocols outlined by ThermoFisher for a co-transfection of plasmid containing gene sequence encoding for an IgG light and an IgG heavy chain. For HEK293 expression, equal amounts by weight of heavy chain plasmid and light chain plasmid were co-transfected. Cells were allowed to grow for 7 days after which supernatants were collected for antibody purification. Antibodies were screened for binding to protein A or protein G sensors via Octet QKe quantitation (Pall ForteBio Corp, Menlo Park, CA, USA). Constructs which bound to protein A were purified and quantified as described in Bergeron et al. for protein quality.

Example 2

Target Binding Affinity and Potency Assay

Affinity for each mAb was assessed by Biacore and the IC50 was determined via a suitable cell based potency assay. Surface Plasmon Resonance was performed on a Biacore T200 (GE Healthcare, Pittsburgh, PA) to measure binding affinities of each antibody to its target, 2.5 μg/ml of each target protein was immobilized by amine coupling using EDC/NHS for a final density ~250 RU (resonance unit) on CM5 sensor flow cells 2-4, respectively.

Flow cell 1 was used as an internal reference to correct running buffer effects. Antibody binding was measured at 15° C. with a contact time of 250 s and flow rate of 30 μl/min. The dissociation period was 300 s. Regeneration was performed with regeneration buffers (10 mM Glycine pH1.5 and 10 mM NaOH) and flow rate at 20 μl/min for 60 s each. Running/dilution buffer (1×HBS-EP, GE Healthcare, BR-1006-69, 10× including 100 mM HEPES, 150 mM NaCl, 30 mM EDTA and 0.5% v/v surfactant P20, pH7.4, 1:10 in filtered MQ H2O) was used as negative control at the same assay format.

Data were analyzed with Biacore T200 Evaluation software by using the method of double referencing. The resulting curve was fitted with the 1:1 binding model. No differences in binding affinities or IC50 were observed between wild-type and N434H mutant IgGs (Table 1).

TABLE 1

Affinities and potencies of WT and N434H mutant IgGs. No differences were measured between the WT and mutant IgGs:

| mAb | Wild-Type Affinity | Wild-Type IC50 | N434H Mutant Affinity | N434H Mutant IC50 |
|---|---|---|---|---|
| mAb1 | 4.83E−10 | 1.1 nM | 3.73E−10 | 0.99 nM |
| mAb2 | 8.51E−11 | 23.7 nM | 5.55E−11 | 20.9 nM |
| mAb3 | 4.5E−10 | 0.13 µg/ml | 3.8E−10 | N/A | mAb1, mAb2, and mAB3 refer to caninized anti-IL31, anti-NGF, and anti-TGFβ antibodies, respectively. Anti-IL31 antibody is well known in the art. See e.g., U.S. Pat. Nos. 10,526,405; 10,421,807; 9,206,253; 8,790,651. Anti-NGF antibody is also well known in the art. See e.g., U.S. Pat. Nos. 10,125,192; 10,093,725; 9,951,128; 9,617,334; and 9,505,829. Anti-TGFβ antibody is also well known in the art. See e.g., U.S. patent applications 63/036,092 and 63/248,679 and PCT Patent Application PCT/US2021/036347. Anti-TGFβ antibody ZTS-4155 was used.

Example 3

In Vitro FcRn Binding Assay

Canine FcRn was isolated, prepared and mutant Fc IgGs were assayed against canine FcRn according to Bergeron et. al., discussed above. Standard PCR was used to amplify canine FcRn-α subunit and β-microglobulin using degenerate primers designed from sequence alignments from cynomolgus monkey, human, mouse and rat. Primers contained HindIII at 3 prime and BamH1 at the 5 prime ends to facilitate subcloning into pcDNA3.1(+) vectors, engineered with a c-terminal 6× His+BAP tag (AGLNDIFEAQK-IEWHE). FcRn-α subunit and β-microglobulin were co-transfected into HEK 293 cells and the FcRn complex was purified by IMAC affinity purification via the c-terminal His tag. KD's were measured by Biacore 3000 or Biacore T200 (GE Healthcare, Pittsburgh, PA, USA) using a CM5 sensor chip.

FcRn was immobilized on the surface of the sensor using the standard amine immobilization method to reach the desired surface density. HBS-EP was used as the immobilization running buffer and 10 mM MES; 150 mM NaCl; 0.005% Tween20; 0.5 mg/mL BSA; pH6 and pH7.2 and PBS; 0.005% Tween20; 0.5 mg/mL BSA; pH7.4 were used for method running buffers and titrations. Fc mutant IgGs were flowed over receptor surfaces and affinity was determined using Scrubber2 software analysis (BioLogic Software Pty, Ltd., Campbell, Australia) or T200 evaluation software (Table 2). Blank runs containing buffer only were subtracted out from all runs. Flow cells were regenerated using 50 mM Tris pH8. Runs were performed at 15° C.

Mutations made at position 434 for mAbs 1, 2, and 3 have a marked effect on the affinity of the IgG to FcRn at pH6. The mutation N434H has a significant increase in FcRn affinity at pH6, while maintaining weak affinity at pH 7.2 for all three mAbs. Extensive mutagenesis at position 434 reveals that several other mutations have increase affinity for FcRn at pH6. This study reveals that the increase in FcRn affinity for IgG is not dependent on the VHVL domains, and is universal for any canine IgGB (65).

TABLE 2

Binding of wild-type (WT) and N434 mutant IgGs to Canine FcRn measured by surface plasmon resonance (Biacore):

| Name | Mutation | FcRn pH 6 | FcRn pH 7.2 |
|---|---|---|---|
| mAb1 | WT | 15-24.4 nM | NBO |
| mAb1 | N434H | 0.7-1.3 nM | 5 µM |
| mAb2 | WT | 57.2 nM | NBO |
| mAb2 | N434H | 7.3 nM | 1.3 µM |
| mAb3 | WT | 523 nM | NBO |
| mAb3 | N434H | 4.8 nM | 38 nM |
| mAb3 | N434S | 17.3 nM | 66.7 nM |
| mAb3 | N434A | 21.4 nM | 95.8 nM |
| mAb3 | N434F | 1.67 nM | 40.1 nM |
| mAb3 | N434G | 26.6 nM | 0.31 nM |
| mAb3 | N434I | 16.7 nM | 5.91 nM |
| mAb3 | N434K | 15.8 nM | 14.3 nM |
| mAb3 | N434L | 28 nM | 15.5 nM |
| mAb3 | N434M | 18.8 nM | 11.0 nM |
| mAb3 | N434Q | 11.8 nM | 50.2 nM |
| mAb3 | N434R | 2.7 nM | 285 nM |
| mAb3 | N434T | 16.6 nM | 406 nM |
| mAb3 | N434V | 13.6 nM | 6.19 nM |
| mAb3 | N434W | 2.11 nM | 162 nM |
| mAb3 | N434Y | 1.56 nM | 38.6 nM |
| mAb3 | N434C | NBO | 270 nM |
| mAb3 | N434D | NBO | 10.3 nM |
| mAb3 | N434E | NBO | 5.67 nM |
| mAb3 | N434P | NBO | WB | mAb1, mAb2, and mAB3 refer to caninized anti-IL31, anti-NGF, and anti-TGFβ antibodies, respectively, as shown in Table 1 above.
NBO = No binding Observed.
WB = Weak binding; KD could not be calculated accurately.

Example 4

Fc Mutant IgG PK Studies in Dogs

The objective of the study was to determine the pharmacokinetics of 2 IgG monoclonal antibodies in dogs (mAb1 and mAb2), raised against two distinct and different targets with the Fc mutant N434H incorporated into each IgG.

For the mAb1 WT and N434H mutant IgGs, groups of 4 male beagle dogs were administered a single 2 mg/kg dose intravenously. For the mAb2 WT and mutant IgGs, groups of 4 male and 4 female beagle dogs were administered three 2 mg/kg doses of one of the IgGs at 28 day intervals. The first two doses were subcutaneously administered and the last dose was intravenously administered. 'Free' IgGs in canine serum were assayed using validated ligand binding assays specific to each IgG and automated on the Gyrolab xP™ platform (FIGS. 3-6). Pharmacokinetic calculations were performed using the noncompartmental approach (linear trapezoidal rule for AUC calculations) with the aid of Watson™ (Table 3). For the mAb2 IgGs, half-lives were estimated for the first and second doses using the time points from 7 to 28 days after dosing. Half-lives for the last dose were estimated using time points from 7 to 42 days after dosing. Additional calculations were performed with Excel™, including correction of the AUC for the overlap of the concentration-time profiles after the 2nd and 3rd injections of drug. Summaries of concentration-time data and pharmacokinetic data with simple statistics (mean, standard deviation, coefficient of variation) were calculated using Excel™ or Watson™. No other statistical analyses were conducted.

TABLE 3

Calculated Half-Life's for wild-
type and N434H mutant canine IgGs:

| IgG | Half-Life (days) |
|---|---|
| mAb1 WT | 9.7 +/− 2.6 |
| mAb1 N434H | 17.1 +/− 5.1 |
| mAb2 WT | 9.2 +/− 1.7 |
| mAb2 N434H | 19.3 +/− 3.1 | mAb1 and mAb2 refer to caninized anti-IL31 and anti-NGF antibodies, respectively.

The canine IgGB (65) point mutation N434H has been shown to increase the half-life of two different canine IgGs in beagle dogs. For mAb1 the half-life increased from 9.7+/−2.6 days to 17.1+/−5.1 days, and for Ma2b2 from 9.2+/−1.7 to 19.3+/−3.1. The mechanism of action is via enhancing affinity to canine FcRn at pH6 and it has been demonstrated with three canine IgGs, that bind very different and distinct soluble targets. Therefore, it has been demonstrated that the half-life extension of N434 mutations of IgGB (65) is independent of the VHVL domains.

Example 5

FcRn Binding Assay

Canine FcRn was isolated, prepared and mutant Fc IgGs were assayed against canine FcRn according to Bergeron et. al., discussed above. Standard PCR was used to amplify capture, method running buffer and titrations. 1×HBS-P, 0.5 mg/mL BSA; pH7.4 was also used for method running buffer and titrations. Fc mutant IgGs were flowed over receptor surfaces and affinity was determined using T200 evaluation software or Biacore Insight Evaluation software. Blank runs containing buffer only were subtracted out from all runs. Flow cells were regenerated using 50 mM Tris pH8 or pH9. Runs were performed at 15° C.

Mutations made at respective positions have a marked effect on the affinity of the IgG to FcRn at pH6. Binding of wild-type (WTs) and mutant IgGs to canine FcRn were measured by surface plasmon resonance (Biacore).

The marked effect on the affinity was observed in completely different and structurally different antibodies that bind different targets (i.e., anti-IL31 and anti-NGF antibodies) and also different versions of antibodies that bind the same target (i.e., different versions of anti-IL31 and anti-NGF antibodies) (Tables 1-4). Therefore, the increase in FcRn affinity for IgG is not dependent on the VHVL domains or CDR regions. In addition, the marked effect on the affinity was observed in multiple IgG subclasses although there is a slight variation. Generally, the results show that the increase in FcRn affinity for IgG is independent of canine IgG subclass.

TABLE 4A

Binding of wild-type (WT) and N434 mutant IgGs to Canine FcRn

| Mutation | canine IgG subclass | Target 1 + mAb1 | | | Target 2 + mAb2 | | |
|---|---|---|---|---|---|---|---|
| | | ID No. | KD pH 6 | KD pH 7.4 | ID No. | KD pH 6 | KD pH 7.4 |
| WT | IgGA | 1 | 7.99E−08 | NBO | 39 | 9.55E−08 | NBO |
| N434F | IgGA | 2 | 1.27E−08 | NBO | 40 | 9.81E−09 | NBO |
| N434H | IgGA | 3 | 1.23E−08 | NBO | 41 | 1.04E−08 | NBO |
| N434R | IgGA | 4 | 4.38E−08 | NBO | 42 | 1.51E−08 | NBO |
| N434S | IgGA | 5 | NBO | NBO | 43 | 1.47E−07 | NBO |
| N434W | IgGA | 6 | 1.99E−08 | NBO | 44 | 1.06E−08 | 1.52E−06 |
| N434Y | IgGA | 7 | 2.52E−08 | 5.73E−07 | 45 | 1.43E−08 | 9.53E−06 |
| WT | IgGB | 8 | 1.99E−08 | 1.87E−05 | 46 | 9.15E−08 | NBO |
| N434A | IgGB | 9 | 1.39E−07 | 1.75E−07 | 47 | 9.81E−09 | NBO |
| N434F | IgGB | 10 | 3.07E−08 | 3.37E−05 | 48 | 1.92E−09 | NBO |
| N434G | IgGB | 11 | 1.18E−07 | 2.60E−05 | 49 | 3.43E−08 | NBO |
| N434I | IgGB | 12 | 7.71E−08 | 1.96E−05 | 50 | 2.76E−09 | 2.28E−05 |
| N434K | IgGB | 13 | 9.11E−09 | 7.86E−09 | 51 | 1.93E−09 | 5.94E−07 |
| N434L | IgGB | 14 | 1.43E−08 | 9.97E−07 | 52 | 1.83E−09 | NBO |
| WT | IgGC | 35 | 1.00E−07 | NBO | 53 | 5.20E−08 | NBO |
| N434H | IgGC | 36 | 8.79E−08 | NBO | 54 | 2.04E−08 | NBO |
| WT | IgGD | 37 | 3.45E−08 | NBO | 55 | 7.10E−08 | NBO |
| N434H | IgGD | 38 | 3.21E−09 | NBO | 56 | 1.20E−08 | NBO | mAb1 and mAb2 refer to caninized anti-IL31 (34D03) and anti-NGF (ZTS-841) antibodies, respectively. mAb1 in this table and Tables 1-3 above are the same (i.e., 34D03). However, mAb2 in this table is ZTS-841 anti-NGF antibody which has different VL, VH, and CDR regions, relative to mAb2 antibody listed in Tables 1-3; NBO = No binding Observed.

canine FcRn-α subunit and β-microglobulin. FcRn-α subunit and β-microglobulin were co-transfected into HEK 293 cells and the FcRn complex was purified by IMAC affinity purification via the c-terminal His tag. FcRn complex was biotin labeled through BirA enzymatic biotinylatoin reaction. KD's were measured by Biacore T200 (GE Healthcare, Pittsburgh, PA, USA) or Biacore 8K (Cytiva, Marlborough, MA, USA) using a SA sensor chip.

FcRn was captured on the surface of the sensor using a modified SA capture method. 10 mM MES; 150 mM NaCl; 0.005% Tween20; 0.5 mg/mL BSA; pH6 was used as

TABLE 4B

Binding of wild-type (WT) and N434 mutant IgGs to Canine FcRn

| Mutations | canine IgG subclass | Target 1 + mAb1 | | |
|---|---|---|---|---|
| | | ID No. | KD pH 6 | KD pH 7.4 |
| N434M | IgGB | 15 | 1.42E−08 | 1.46E−04 |
| N434Q | IgGB | 16 | 5.91E−09 | 2.18E−08 |

TABLE 4B-continued

Binding of wild-type (WT) and N434 mutant IgGs to Canine FcRn

| | | | Target 1 + mAb1 | |
|---|---|---|---|---|
| Mutations | canine IgG subclass | ID No. | KD pH 6 | KD pH 7.4 |
| N434R | IgGB | 17 | 9.06E−10 | 3.11E−09 |
| N434S | IgGB | 18 | 2.02E−08 | 6.96E−06 |
| N434T | IgGB | 19 | 3.42E−08 | 5.54E−07 |
| N434V | IgGB | 20 | 6.16E−09 | 2.75E−06 |
| N434W | IgGB | 21 | 1.98E−09 | 2.53E−05 |
| N434Y | IgGB | 22 | 2.71E−09 | 1.90E−06 |
| N434H | IgGB | 31 | 6.45E−09 | NBO |
| WT 2 | IgGB | 33 | 4.00E−08 | NBO |
| N434H | IgGB | 34 | 1.00E−09 | 8.39E−05 | mAb1 refers to caninized anti-IL31 antibody. ID Numbers 15-21 and 31 correspond to 34D03 anti-IL31 antibody. ID numbers 33 and 34 correspond to 11E12 anti-IL31 antibody.

Example 6

Fc Mutant IgG PK Studies in Dogs

The objective of the study was to determine effectiveness of a dose of 4.0 mg/kg of ZTS-00008183 based on efficacy in a canine induced-pruritus model where efficacy was measured by assessing reduction in pruritus for up to 210 days following administration of Test Article on Day 0. The term "ZTS-00008183," as used herein refers an anti-IL31 antibody having N434H mutation in its constant region. ZTS-00008183 has the variable regions (i.e., VL and VH including CDRs) of 34D03, described herein.

ZTS-00008183 or placebo were administered by single SC injection to Beagle dogs (age at ~4 years old). The treatments are summarized below.

TABLE 5

Treatment Summary

| Treatment Group | Route | Dose (mg/kg) | Compound | Formulation Concentration (mg/mL) | N |
|---|---|---|---|---|---|
| T01 | SC | 0 | Placebo | 0 | 8 |
| T02 | SC | 4.0 | ZTS-00008183 | 40 | 8 |

Serum samples were collected at pre-dose (day −7) and on days 7, 14, 28, 56, 84, 112, 140, 168 and 210 following drug administration.

Specifically, beagle dogs (n=8, age about 4 years old at the dosing date) were treated with a single subcutaneous administration of 4 mg/kg ZTS-00008183 in IL-31 induced pruritus challenge study. Serum samples were collected at predose (day −7), and on days 7, 14, 28, 56, 84, 112, 140, 168 and 210 following drug administration.

The test mAbs were quantified using ligand bind assays. Anti-drug antibody (ADA) was evaluated with qualified ADA assay methods.

Bioanalytical data were received from BioAgilytix Labs as Excel™ spreadsheets. The data were imported into Watson™ v.7.4.1. Toxicokinetic and pharmacokinetic parameters ($C_{max}$, $t_{max}$, AUC, AUCextrap and $t_{1/2}$) were calculated using the non-compartmental approach with the aid of Watson™ v.7.4.1. ZTS-00008183 half-lives were estimated for groups T02 using the timepoints from 56 to 210 days post dose. Immunogenicity was evaluated.

Serum concentrations of ZTS-00008183 are listed in Table 6

TABLE 6

Pharmacokinetic parameters of ZTS-00008183 in dogs following a single 4 mg/kg subcutaneous administration (T02)

| Parameter | Units | Subject 1 | Subject 2 | Subject 3 | Subject 4 | Subject 5 | Subject 6 | Subject 7 | Subject 8 | Mean | S.D. | % CV |
|---|---|---|---|---|---|---|---|---|---|---|---|---|
| AUC | μg*Days/mL | 1440 | 2070 | 1600 | 2190 | 2110 | 1810 | 2110 | 2160 | 1940 | 285 | 14.7 |
| AUCextrap | μg*Days/mL | 1450 | 2090 | 1600 | 2230 | 2140 | 1830 | 2130 | 2190 | 1960 | 295 | 15.1 |
| $C_{max}$ | μg/mL | 25.3 | 34.5 | 28.6 | 29.5 | 29.8 | 28.7 | 41.9 | 35.7 | 31.8 | 5.29 | 16.7 |
| $t_{max}$ | Days | 14.0 | 7.00 | 7.00 | 14.0 | 28.0 | 7.00 | 7.00 | 7.00 | 11.4 | 7.42 | 65.3 |
| $t_{1/2}$ | Days | 24.9 | 31.6 | 26.3 | 35.2 | 32.0 | 31.6 | 29.2 | 30.8 | 30.2 | 3.31 | 11.0 |

The mean pharmacokinetic parameters of ZTS-00008183 are demonstrated in Table 7 below.

TABLE 7

Mean pharmacokinetic parameters of ZTS-00008183.

| Parameter | Units | ZTS-00008183 |
|---|---|---|
| AUC | μg*Days/mL | 1940 ± 285 |
| AUC Extrap | μg*Days/mL | 1960 ± 295 |
| $C_{max}$ | μg/mL | 31.8 ± 5.3 |
| $t_{max}$ | Days | 11.4 ± 7.4 |
| $t_{1/2}$ | Days | 30.2 ± 3.3 |

No treatment-induced immunogenicity has been detected.

The serum profiles of ZTS-00008183 are illustrated in FIG. 7. The mean serum profiles of ZTS-00008183 are illustrated in FIG. 8.

In sum, the results demonstrate that a canine IgG constant domain having N434H mutation provided the half-life for about 30 days. This is more than 2-fold increase (i.e., 200% increase) in half-life, relative to the half-life of 9.2 to 9.7 days for the wild-type (See Table 2).

Example 7

Long Term Therapeutic Effect of Fc Mutant IgG

A single subcutaneous dose of ZTS-00008183 at 4 mg/kg was evaluated in a canine model of IL-31 induced pruritus.

Twenty-four healthy beagle dogs were randomized to treatment using a randomized complete block design and received ZTS-00008183 at 4 mg/kg bodyweight or a placebo in a parallel-design efficacy study. Animals were blocked by historical pruritic score to form eight (8) complete blocks of size 3.

TABLE 8

| Treatment Group | Route | Dose (mg/kg) | Compound | Formulation Concentration (mg/mL) | N |
|---|---|---|---|---|---|
| T01 | SC | 0 | Placebo | 0 | 8 |
| T02 | SC | 4.0 | ZTS-00008183 | 40 | 8 |

SC refers to subcutaneous; N refers to number of animals.

Each animal was administered the IL-31 challenge (2.5 µg/kg) to induce pruritus on Study Day −7 to establish a baseline pruritic score. Additional IL-31 challenges were administered on Study Days 7, 28, 56, 84, 112, 140, 168 and 210.

Animals were observed for pruritic behavior for a 120-minute period after each challenge. Observations were made over a 1-minute window and any pruritic activity in that window resulted in a "yes" response. The cumulative number of yes responses determined the Pruritus Score.

There were no adverse events noted during this study and all test and control articles and challenge materials were administered according to protocol.

The results demonstrate that a single SC dose of ZTS-00008183 at 4.0 mg/kg showed a significantly lower least squares means pruritis score (Tables 9, 11 and 13) compared with control at 3, 4 and 5 months (P<0.0001) in our canine model of IL-31 induced pruritus.

As shown in FIGS. 9-13, ZTS-0008183 (T02), when dosed at 4 mg/kg, showed a significantly lower total pruritus score in our canine model of IL-31 induced pruritus compared with control on Study Days 84, 112, 140, 168, and 210.

Based on the pruritic scores, the results also demonstrate that ZTS-00008183 is therapeutically effective for 84, 112, 140, 168, and 210 days (i.e., about 7 months).

The results further demonstrate that ZTS-00008183 has a long term therapeutic effect and can be administered once every 3, 4, 5, 6, or 7 months.

TABLE 9

Least Squares Means Pruritic Scores with 92.9% Upper and Lower Confidence Limit at Day 84 Following Treatment with Placebo (T01) or ZTS-00008183 (T02).

| Treatment number | number of animals | least squares mean (lsm) | standard error | 92.9% lower confidence limit | 92.9% upper confidence limit | range | % change in means (1) |
|---|---|---|---|---|---|---|---|
| T01 | 8 | 86 | 6.0 | 73 | 98 | 27 to 112 | |
| T02 | 8 | 9 | 6.2 | −4 | 21 | 0 to 24 | 90.0 |

TABLE 10

Difference in Means Between Treatments Scores with 92.9% Upper and Lower Confidence Limit at Day 84 Following Treatment with Placebo (T01) or ZTS-00008183 (T02).

| Contrast | difference in means | standard error | 92.915% lower confidence limit | 92.915% upper confidence limit | df | p value | significant at 0.07085 level |
|---|---|---|---|---|---|---|---|
| T01 vs T02 | 77.1 | 8.77 | 59.9 | 94.3 | 13.6 | <.0001 | * |

TABLE 11

Least Squares Means Pruritic Scores with 95.4% Upper and Lower Confidence Limit at Day 112 Following Treatment with Placebo (T01) or ZTS-00008183 (T02).

| Treatment number | number of animals | least squares mean (lsm) | standard error | 95.425% lower confidence limit | 95.425% upper confidence limit | range | % change in means (1) |
|---|---|---|---|---|---|---|---|
| T01 | 8 | 84 | 6.5 | 70 | 98 | 25 to 117 | |
| T02 | 8 | 11 | 6.6 | −3 | 26 | 1 to 29 | 86.8 |

TABLE 12

Difference in Means Between Treatments Scores with 95.4%
Upper and Lower Confidence Limit at Day 112 Following
Treatment with Placebo (T01) or ZTS-00008183 (T02).

| Contrast | difference in means | standard error | 95.425% lower confidence limit | 95.425% upper confidence limit | df | p value | significant at 0.04575 level |
|---|---|---|---|---|---|---|---|
| T01 vs T02 | 72.8 | 10.63 | 49.5 | 96.1 | 13.8 | <.0001 | * |

TABLE 13

Least Squares Means Pruritic Scores with 95.4% Upper and Lower Confidence Limit
at Day 140 Following Treatment with Placebo (T01) or ZTS-00008183 (T02).

| Treatment number | number of animals | least squares mean (lsm) | standard error | 95.468% lower confidence limit | 95.468% upper confidence limit | range | % change in means (1) |
|---|---|---|---|---|---|---|---|
| T01 | 8 | 86 | 5.8 | 74 | 99 | 33 to 116 | |
| T02 | 8 | 21 | 5.9 | 8 | 34 | 9 to 45 | 76.1 |

TABLE 14

Difference in Means Between Treatments Scores with 95.4%
Upper and Lower Confidence Limit at Day 140 Following
Treatment with Placebo (T01) or ZTS-00008183 (T02).

| Contrast | difference in means | standard error | 95.468% lower confidence limit | 95.468% upper confidence limit | df | p value | significant at 0.04352 level |
|---|---|---|---|---|---|---|---|
| T01 vs T02 | 65.8 | 9.67 | 44.3 | 87.3 | 13.9 | <.0001 | * |

In sum, the results demonstrate that a canine IgG constant domain having N434H mutation maintains a therapeutic serum level for about 210 days (i.e., 7 months). This is several folds higher, relative to the days of therapeutic level of wild-type anti-IL31 antibody reported in earlier studies.

Example 8

FcRn Binding Assay

As discussed in Example 3, canine FcRn was isolated, prepared and mutant Fc IgGs were assayed against canine FcRn according to Bergeron et. al., discussed above. Standard PCR was used to amplify canine FcRn-α subunit and β-microglobulin using degenerate primers designed from sequence alignments from cynomolgus monkey, human, mouse and rat. Primers contained HindIII at 3 prime and BamH1 at the 5 prime ends to facilitate subcloning into pcDNA3.1(+) vectors, engineered with a c-terminal 6× His+BAP tag (AGLNDIFEAQKIEWHE). FcRn-α subunit and β-microglobulin were co-transfected into HEK 293 cells and the FcRn complex was purified by IMAC affinity purification via the c-terminal His tag. KD's were measured by Biacore T200 (GE Healthcare, Pittsburgh, PA, USA) using a CM5 or SA sensor chip.

FcRn was captured on the surface of the sensor using a modified SA capture method. 10 mM MES; 150 mM NaCl; 0.005% Tween20; 0.5 mg/mL BSA; pH6 was used as capture, method running buffer and titrations. 1×HBS-P, 0.5 mg/mL BSA; pH7.4 was also used for method running buffer and titrations. Fc mutant IgGs were flowed over receptor surfaces and affinity was determined using T200 evaluation software or Biacore Insight Evaluation software. Blank runs containing buffer only were subtracted out from all runs. Flow cells were regenerated using 50 mM Tris pH8 or pH9. Runs were performed at 15° C.

Mutations made at position 434 for mAb3 anti-TGFβ antibodies have a marked effect on the affinity of the IgG to FcRn at pH6. The mutation N434H has a significant increase in FcRn affinity at pH6, while maintaining weak affinity at pH 7.4. This study reveals that the increase in FcRn affinity for IgG is not dependent on the VHVL domains, and is universal for any canine anti-TGFβ antibody.

TABLE 15

| | | | | | | | | | | | |
|---|---|---|---|---|---|---|---|---|---|---|---|
| Binding of wild-type (WT) and N434 mutant IgGs to Canine FcRn measured by surface plasmon resonance (Biacore): | | | | | | | | | | | |
| IgG | ID No. | KD at pH 6 | KD at pH 7.4 | ID No. | KD at pH 6 | KD at pH 7.4 | ID No. | KD at pH 6 | KD at pH 7.4 | ID No. | KD at pH 6 | KD at pH 7.4 |
| WT | 1 | 2.44E−08 | NBO | 3 | 8.74E−08 | NBO | 5 | 3.74E−08 | NBO | 7 | 7.53E−08 | NBO |
| N434H | 2 | 7.06E−09 | NBO | 4 | 1.79E−09 | 2.34E−05 | 6 | 1.07E−09 | 2.88E−05 | 8 | 1.68E−09 | 3.67E−06 |

Canine IgG subclass B was used.
NBO = No binding Observed.
ID numbers 1, 3, 5, and 7 represent wildtype mAb3 anti-TGFβ antibodies ZTS-501, ZTS-426, ZTS-122, and ZTS-207, respectively. ID numbers 2, 4, 6, and 8 represent mutant mAb3 anti-TGFβ antibodies ZTS-501, ZTS-426, ZTS-122, and ZTS-207, respectively.

Having described preferred embodiments of the invention, it is to be understood that the invention is not limited to the precise embodiments, and that various changes and modifications may be effected therein by those skilled in the art without departing from the scope or spirit of the invention as defined in the appended claims.

What is claimed is:

1. A modified IgG comprising:

a canine IgG constant domain comprising at least one amino acid substitution relative to a wild-type canine IgG constant domain, wherein said substitution is at amino acid residue 434, numbered according to the EU index as in Kabat, wherein said substitution is a substitution of asparagine at position 434 with histidine (N434H), wherein said IgG is an anti-TGFβ molecule, and wherein the anti-TGFβ molecule comprises a variable heavy (VH) chain having the amino acid sequence set forth in SEQ ID NO.: 77, 87, 97, 107, or 117 and a variable light (VL) chain having the amino acid sequence set forth in SEQ ID NO.: 79, 89, 99, 109, or 119.

2. The modified IgG of claim 1, wherein the modified IgG has a higher affinity for FcRn than an IgG having the wild-type canine IgG constant domain.

3. The modified IgG of claim 1, wherein the modified IgG has a higher half-life than an IgG having the wild-type canine IgG constant domain.

4. The modified IgG of claim 1, wherein the modified IgG comprises an Fc constant region having CH2 or CH3 domain, or a combination thereof.

5. The modified IgG of claim 1, wherein the wild-type canine IgG constant domain comprises the amino acid sequence set forth in SEQ ID NO.: 2.

6. A pharmaceutical composition comprising the modified IgG of claim 1 and a pharmaceutically acceptable carrier.

7. A kit comprising the modified IgG of claim 1, in a container, and instructions for use.

8. A fusion molecule comprising the modified IgG of claim 1.

9. A method for increasing the serum half-life of a canine IgG molecule in a dog, the method comprising: administering to said dog a composition comprising a modified IgG, said modified IgG comprising a canine IgG constant domain comprising at least one amino acid substitution relative to a wild-type canine IgG constant domain, wherein said substitution is at amino acid residue 434, numbered according to the EU index as in Kabat, wherein said substitution is a substitution of asparagine at position 434 with histidine (N434H), wherein said IgG is an anti-TGFβ molecule, and wherein the anti-TGFβ molecule comprises a variable heavy (VH) chain having the amino acid sequence set forth in SEQ ID NO.: 77, 87, 97, 107, or 117 and a variable light (VL) chain having the amino acid sequence set forth in SEQ ID NO.: 79, 89, 99, 109, or 119.

10. The method of claim 9, wherein the modified IgG comprises an Fc constant region having CH2 or CH3 domain, or a combination thereof.

11. The method of claim 9, wherein the wild-type canine IgG constant domain comprises the amino acid sequence set forth in SEQ ID NO.: 2.

\* \* \* \* \*